US009242945B2

(12) United States Patent
Reddy et al.

(10) Patent No.: US 9,242,945 B2
(45) Date of Patent: Jan. 26, 2016

(54) SUBSTITUTED 2-BENZYLIDENE-2H-BENZO [B][1,4]THIAZIN-3(4H)-ONES, DERIVATIVES THEREOF, AND THERAPEUTIC USES THEREOF

(71) Applicants: E. Premkumar Reddy, Villanova, PA (US); M. V. Ramana Reddy, Upper Darby, PA (US)

(72) Inventors: E. Premkumar Reddy, Villanova, PA (US); M. V. Ramana Reddy, Upper Darby, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 14/090,350

(22) Filed: Nov. 26, 2013

(65) Prior Publication Data
US 2014/0086941 A1 Mar. 27, 2014

Related U.S. Application Data

(63) Continuation-in-part of application No. PCT/US2012/039544, filed on May 25, 2012.

(60) Provisional application No. 61/490,786, filed on May 27, 2011.

(51) Int. Cl.
| C07D 279/16 | (2006.01) |
| C07D 417/06 | (2006.01) |
| C07D 417/10 | (2006.01) |
| C07D 279/20 | (2006.01) |
| A61K 47/48 | (2006.01) |

(52) U.S. Cl.
CPC ........ *C07D 279/16* (2013.01); *A61K 47/48384* (2013.01); *C07D 279/20* (2013.01); *C07D 417/06* (2013.01); *C07D 417/10* (2013.01)

(58) Field of Classification Search
CPC .. C07D 279/16; C07D 279/20; C07D 417/06; C07D 417/10
USPC .......................................... 544/52; 514/224.2
See application file for complete search history.

(56) References Cited

U.S. PATENT DOCUMENTS

| 2,956,054 | A | 10/1960 | Laubach |
| 2,956,055 | A | 10/1960 | Laubach |
| 3,635,956 | A | 1/1972 | Krapcho |
| 3,746,706 | A | 7/1973 | Krapcho |
| 3,865,818 | A | 2/1975 | Krapcho et al. |
| 3,923,709 | A | 12/1975 | Worley |
| 4,078,062 | A | 3/1978 | Krapcho |
| 4,490,292 | A | 12/1984 | Maki et al. |
| 5,362,871 | A | 11/1994 | Giordano et al. |
| 5,496,815 | A | 3/1996 | Ozeki et al. |
| 5,496,817 | A | 3/1996 | Kawashima et al. |
| 6,498,163 | B1 | 12/2002 | Boschelli et al. |
| 6,951,855 | B2 | 10/2005 | Bird |
| 7,049,312 | B1 | 5/2006 | Rafferty et al. |
| 7,205,298 | B2 | 4/2007 | Kuo et al. |
| 7,208,489 | B2 | 4/2007 | Barvian et al. |
| 2002/0013493 | A1 | 1/2002 | Suzuki |

FOREIGN PATENT DOCUMENTS

| EP | 0441539 A2 | 8/1991 |
| JP | 60072875 A | 4/1985 |
| JP | 61229874 A | 10/1986 |
| WO | 9937641 A1 | 7/1999 |
| WO | WO 9937641 A1 * | 7/1999 |
| WO | 0063197 A1 | 10/2000 |
| WO | 0075139 A2 | 12/2000 |
| WO | 2008053863 A1 | 5/2008 |
| WO | 2010077680 A2 | 7/2010 |

OTHER PUBLICATIONS

Souza et al. Quimica Nova (2010), 33(3), 562-565.*
Souza et al., "Efficient Synthesis of Benzothiazine and Acrylamide Compounds", Quim. Nova, vol. 33, No. 3, pp. 562-565 (2010).
Chem Abstr. 148:517737, Accession No. 2008:552507, CAPLUS (2008), abstracting WO2008053863A1.
Chem Abstr. 131:129999, Accession No. 1999:487539, CAPLUS (1999), abstracting DE 1998-19802239.
Mackie, "The benzylidene derivative of 3-Keto-6: 7-dimethoxy-2: 3-dihydrobenzo-1:4-thiazine", Journal of the Chemical Society, 1315-1316 (1949).
Souza et al., "Efficient Synthesis of Benzothiazine and Acrylamide Compounds", Quim. Nova, vol. 33, No. 3, 562-565, (2010).
Guarda et al., "Synthesis and Structural Study of Arylidene Thiazolidine and Benzothiazine Compounds", Sulfur Letters, vol. 26, Feb. 2003, pp. 17-27.
CAS RN 453526-43-7, STN Entry Date Sep. 20, 2002.
CAS RN 452938-31-7, STN Entry Date Sep. 19, 2002.
CAS RN 454209-72-4, STN Entry Date Sep. 23, 2002.
CAS RN 457082-42-7, STN Entry Date Sep. 30, 2002.

(Continued)

*Primary Examiner* — Kahsay Habte
(74) *Attorney, Agent, or Firm* — Drinker Biddle & Reath LLP

(57) ABSTRACT

The present invention relates to compounds according to Formula I:

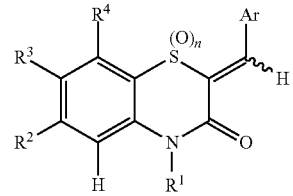

Formula I and salts thereof, wherein $R^1$, $R^2$, $R^3$, $R^4$, Ar, and n are as defined herein. Methods for preparing compounds of Formula I are also provided. The present invention further includes methods of treating cellular proliferative disorders, such as cancer, with the compounds of Formula I.

36 Claims, 1 Drawing Sheet

(56) References Cited

OTHER PUBLICATIONS

CAS RN 481692-14-2, STN Entry Date Jan. 27, 2003.
CAS RN 502864-42-8, STN Entry Date Apr. 14, 2003.
CAS RN 452952-12-4, STN Entry Date Sep. 19, 2002.
CAS RN 454191-59-4, STN Entry Date Sep. 23, 2002.
CAS RN 454237-01-5, STN Entry Date Sep. 23, 2002.
CAS RN 502746-44-3, STN Entry Date Apr. 11, 2003.
CAS RN 507248-06-8, STN Entry Date Apr. 29, 2003.
CAS RN 452970-76-2, STN Entry Date Sep. 19, 2002.
CAS RN 454206-60-1, STN Entry Date Sep. 23, 2002.
CAS RN 455315-93-2, STN Entry Date Sep. 26, 2002.
CAS RN 502744-72-1, STN Entry Date Apr. 11, 2003.
CAS RN 507245-59-2, STN Entry Date Apr. 29, 2003.
Bakthadoss et al., "Simple and New Protocol for the Synthesis of Novel (z)-3-Arylidenebenzothiazepin-4-ones Using Baylis-Hillman Derivatives", Synthetic Communications, (2008) 38:3406-3413.
Trifilenkov et al., "Liquid-Phase Parallel Synthesis of Combinatorial Libraries of Substituted 6-Carbamoyl-3,4-dihydro-2H-benzo [1,4] thiazines", J. Comb. Chem., (2006) 8:469-479.
Kamila et al., "Synthesis of (Z)-hetarylmethylene and (Z)-substituted benzylidene derivatives of 4H-benzo[1,4] thiazine-3-thiones and their subsequent conversion to benzothiopyrano-[3,2-b][1,4]benzothiazines", ARKIVOC, (2006) (ii) 1-14.
Guarda et al., "Synthesis and structural study of arylidene thiazolidine and benzothiazine compounds", Sulfur Letters, (2003) 26:17-27.
Zerzouf et al., "Synthèse et réactivité des dérivés de la 2,3-dihydro-3-hydroxy-2-phényl-1,5-benzothiazépin-4(5H)-one" C.R. Acad. Sci. Paris, (2001) 4:925-931.
Trapani et al., "Synthesis of 2-substituted-N-carboxymethyl-1,5-benzothiazepin-4-ones and -1,4-benzothiazin-3-ones and their evaluation as angiotensin converting enzyme inhibitors", L Farmaco, (1995) 50(2):107-112.
Trapani et al., "Reaction of N,N'-dialkyldithiodianilines with β-ketoesters. A new synthesis of N-alkyl-2-acyl-3-oxo-3,4- dihydro-1,4-benzothiazines", Journal of heterocyclic chemistry, (1992) 29(5):1155-1159.
Tawada et al., "Studies on antidiabetic agents. IX. A new aldose reductase inhibitor, AD-5467, and related 1,4-benzoxazine and 1,4-benzothiazine derivatives: synthesis and biological activity" Chem. Pharm. Bull., (1990) 38 (5):1238-1245.
McCarthy et al. "A New Synthesis of Pyrido [3,2-b] [1,4] benzothiazines" J. Chem. Research(s), (1988) 1332-1352.
Tyndall et al., "A novel synthetic route to phenyl-substituted pyridines synthesis of [1] benzopyrano[4,3-]pyridines, [1] benzothiopyrano[4,3-]bpyridines and pyrido[3,2-] [1,4]benzothiazines(1-azaphenothiazines)", Tetrahedron Letters, (1988) 29(22):2703-2706.
Kaupp et al., "Umlagerungen and Komplexe Eliminierungen mit 1,5-Benzothiazepin-4-onen", Chem. Ber., (1986) 119:3109-3120.
Turk et al., "Synthesis and Central Nervous System Activity of 2-Arylidene-4-aminoalkyl-2H-1,4-benzoxazin-3(4H)-ones and related compounds", Journal of Medicinal Chemistry, (1977) 20(5):729-732.
Worley et al., "2-Dialkylphosphonyl-and-2-Alkylidene-3,4-dihydro-3-oxo-2H-1,4-benzothiazines", J. Org. Chem., (1975) 40(12):1731-1734.
Krapcho et al., "4[3-(Dimethylamino)propyl]-3,4-dihydro-2-(1-hydroxyethyl)-3-phenyl-2H-1,4-benzothiazine and related compounds. New class of antiinflammatory agents", J. Med. Chem., (1973) 16 (7):776-779.
Kugita et al., "Synthesis of 1,5-Benzothiazepine Derivatives", Chem. Pharm. Bull., (1970) 18(10):2028-2037.
Borovik et al., "Amidoalkylation of sulfazone", khimiya geterotsiklicheskikh, (1967) (2): 277-280.
Mason, "Ionic Reactions of Fluorocarbon Iodides", J. Chem. Soc., (1960) 4695-4712.
Chem Abstr. 140162x, vol. 82, 1975, abstracting Japanese Patent Application 49-101389 (1974).
Preuss et al., "Discovery of a *Plasmodium falciparum* Glucose-6-phosphate Dehydrogenase 6-phosphogluconolactonase Inhibitor (R,Z)-N-((1-Ethylpyrrolidin-2-yl)methyl)-2-(2-fluorobenzylidene)-3-oxo-3,4-dihydro-2H-benzo[b][1,4]thiazine-6-carboxamide (ML276) That Reduces Parasite Growth in Vitro", J. Med Chem., 55:7262-7272 online cite (Jun. 13, 2012).
Martinez-Gil et al., "A small molecule multi-kinase inhibitor reduces influenza A virus replication by restricting viral RNA synthesis", Antiviral Research 100:29-37 (Jul. 24, 2013).
Pallela et al., "Design, synthesis, biological evaluation and co-crystal study of novel small molecule inhibitors of protein kinase CK2, 2-benzylidene-4H-benzo[1,4]thiazin-3-one compounds", 245th ACS National Meeting, Apr. 7-11, 2013, New Orleans, Louisiana.

\* cited by examiner

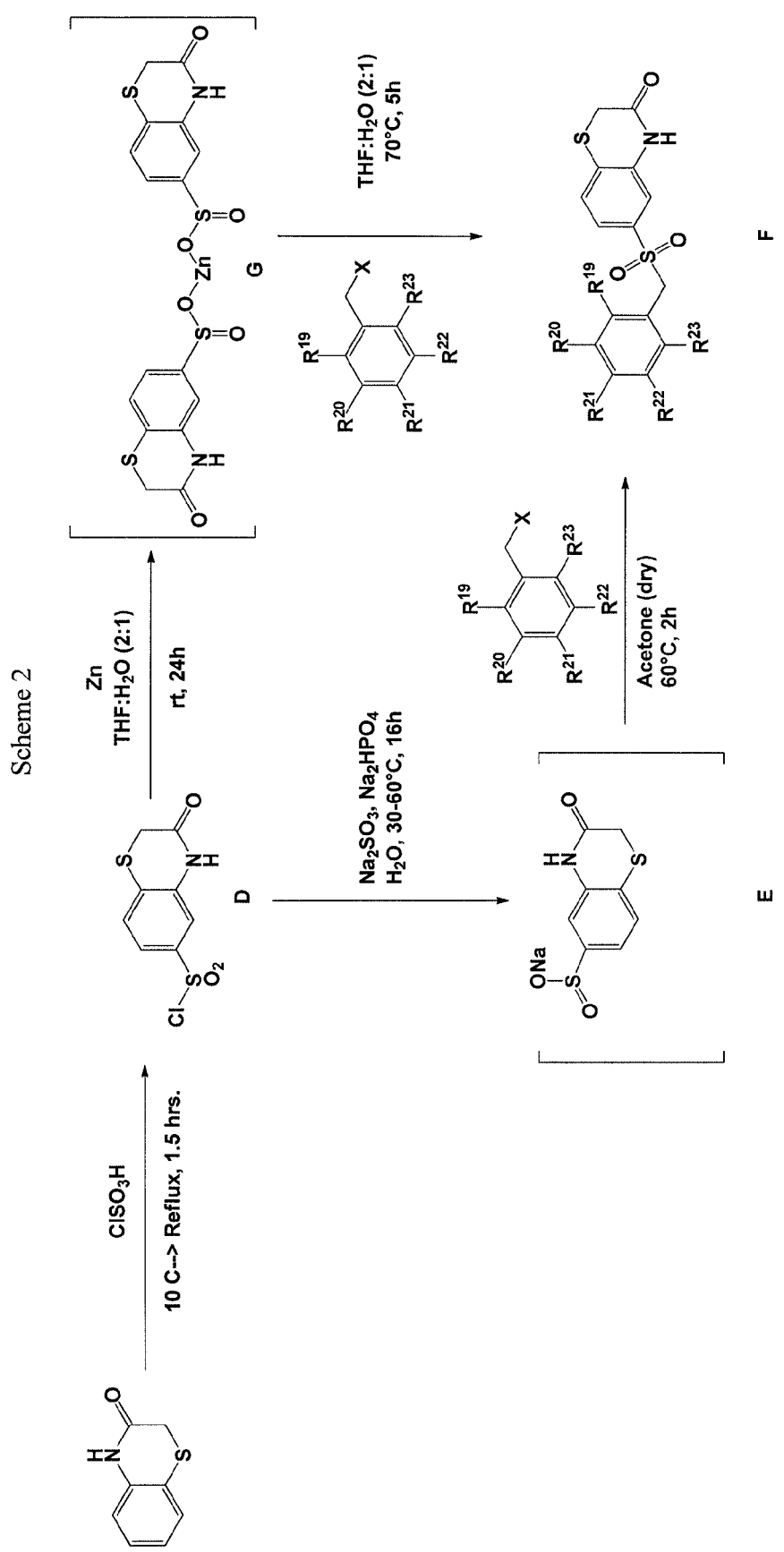
Scheme 2

SUBSTITUTED 2-BENZYLIDENE-2H-BENZO[B][1,4]THIAZIN-3(4H)-ONES, DERIVATIVES THEREOF, AND THERAPEUTIC USES THEREOF

CROSS REFERENCE TO RELATED APPLICATIONS

This application is a continuation-in-part of PCT/US2012/039544, filed May 25, 2012, which claims the benefit of U.S. Provisional Application No. 61/490,786, filed May 27, 2011. The entire disclosures of the aforesaid applications are incorporated herein by reference.

FIELD OF THE INVENTION

The invention relates to compounds, methods for their preparation, compositions including them. The invention further provides methods for the treatment of cellular proliferative disorders, including, but not limited to, cancer.

BACKGROUND OF THE INVENTION

Cellular proliferative disorders such as cancer are among the most common causes of death in developed countries. That said, many cellular proliferative disorders have no available cures or few, if any, treatment options to slow the progression of the disease. For cellular proliferative diseases for which treatments exist, undesirable side effects and limited efficacy often call into question the utility of a given treatment. This is particularly true when the available treatment option(s) may not appreciably prolong life, but have a definitive adverse effect on the quality of time remaining. Thus, identifying new effective drugs for cellular proliferative disorders, and in particular cancer, is a continuing focus of medical research.

Pim-1

Pim-1 is a proto-oncogene which encodes for a serine/threonine. Pim-1 over-expression has been implicated in multiple human cancers, including prostate cancer, acute myeloid leukemia and other hematopoietic malignancies. Pim-1 has also been found to be highly expressed in cell cultures isolated from human tumors and is mainly involved in cell cycle progression, apoptosis and transcriptional activation, as well as more general signal transduction pathways (Bachmann and Möröy, *Int. J. Biochem. Cell Biol.* 37(4):726-30 (2005)). Compounds that inhibit the activity of Pim-1 have potential as anticancer agents.

CK2 and CDK9

Casein Kinase 2 (CK2) is a ubiquitously expressed serine threonine protein kinase, whose activity and expression levels are elevated in a variety of tumor types (St-Denis and Litchfield, *Cell. Mol. Life Sci.*, 66:1817-1829 (2009); Trembley et al., *Cell. Mol. Life Sci.*, 66:1858-1867 (2009)). CK2 is unusual among protein kinases in that it can use both ATP and GTP as phosphate donors (St-Denis and Litchfield, supra). CK2 is also unique in that it is constitutively active and does not appear to require phosphorylation or other post-translational alterations to activate its kinase activity. As a result, the catalytic activity of CK2 is roughly proportional to its cellular concentration (Guerra and Issinger, *Curr. Med. Chemistry*, 15: 1870-1886 (2008)). CK2 is a tetrameric complexes consisting of two catalytic (α and/or α') subunits and two regulatory β subunits (Litchfield, *Biochem. J.* (2003) 369:1-15).

CK2 phosphorylates a large number of substrates, many of which regulate signal transduction pathways that in turn mediate cell growth, cell death, DNA replication and transcription (St-Denis and Litchfield, supra; Trembley et al., supra; Guerra and Issinger, supra). CK2 has also been shown to regulate the activity of tumor suppressors, cell cycle regulatory proteins, apoptotic proteins and oncogenes thus making it a key player in the development and maintenance of cancer progression (Ahmed et al., *Cellular and Molecular Life Sciences*, 66: 1858-1867 (2009)).

Elevated CK2 activity has been associated with the malignant transformation of several tissues and higher levels of CK2 are found to correlate with aggressive behavior of head and neck cancer and poor prognosis of prostate cancer (Gapany et al., *Mol. Med.* 1: 659-666 (1995); Laramas et al., *Eur. J. Cancer.* 43(5):928-34 (2007)). The ability of CK2 to phosphorylate (and activate) PTEN and AKT, two key components of tumor cell survival pathway, suggests an important role of CK2 in suppressing apoptosis in cancer cells (Di Maira et al., *Cell Death Differ.* 12: 668-677 (2005)). Downregulation of CK2 by various approaches results in induction of apoptosis in cultured cell and xenograft cancer models, further suggesting its potential as a therapeutic target (Guerra and Issinger, supra; Ruzzene and Pinna, *Biochim Biophys Acta*, 1804(3): 499-504 (2010)).

Normal cells, which express low levels of CK2, do not appear to have such undue reliance on the activity of this kinase and hence are unaffected by reduction in the levels of this kinase activity, suggesting that development of potent and selective CK2 inhibitors may not exhibit undesirable side effects seen with traditional chemotherapeutic agents.

CDK9 is a cyclin-dependent kinase, which forms a complex with and is regulated by two different regulatory cyclins known as cyclin T and cyclin K (Wang and Fischer, *Trends Pharmacol. Sci.* 29(6):302-13 (2008)). CDK9 accumulates on chromatin and limits the amount of single-stranded DNA in response to replication stress. CDK9/Cyclin K complex was found to play direct role in maintaining genome integrity (Yu and Cortez, *Cell Cycle* 10:1, 28-32 (2011)).

Depletion of CDK9 or its cyclin K (but not cyclin T) was found to impair cell cycle recovery in response to replication stress, resulting in spontaneous DNA damage in replicating cells (Wang et al., supra; Yu et al., *EMBO Rep.* 11(11):876-82 (2010)).

CDK9 is over-expressed in several cancers, including leukemias and lymphomas suggesting that inhibitors might be useful in cancers involving high levels of replication stress, or in combination with replication stress-inducing chemotherapies (Wang and Fischer, supra).

SUMMARY OF THE INVENTION

It has been found that certain compounds and compositions are useful for the treatment of cancer and other cellular proliferative disorders. The biologically active compounds of the invention are substituted 2-benzylidene-2H-benzo[b][1,4]thiazin-3(4H)-ones and related derivatives thereof.

In certain embodiments, the invention is a compound of Formula I or a salt thereof:

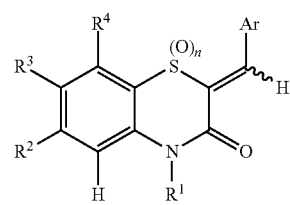

Formula I wherein
n is 0, 1, or 2;
$R^1$ is selected from the group consisting of —H, —($C_1$-$C_6$) alkyl, —($C_2$-$C_6$)alkenyl, —($C_2$-$C_6$)alkynyl, optionally substituted aryl, optionally substituted heteroaryl, optionally substituted aryl-$(C_1-C_6)$alkyl, optionally substituted heteroaryl-$(C_1-C_6)$alkyl, —C(=O)$(C_1-C_6)$alkyl, —C(=O)$(C_2-C_6)$alkenyl, —C(=O)-optionally substituted aryl, —C(=O)$(CH_2)_m$-optionally substituted aryl, and —C(=O)$(CH_2)_p$-optionally substituted heteroaryl;

$R^2$, $R^3$, and $R^4$ are independently selected from the group consisting of —H, halogen, —CN, —$NR^{10}R^{11}$, —OH, —$OR^{13}$, —$(C_1-C_6)$alkoxy, —$NO_2$, —$(C_1-C_6)$alkyl, —$(C_1-C_6)$perfluoroalkyl, —$(C_1-C_6)$perfluoroalkoxy, —C(=O)$R^{15}$, —C(=O)$OR^{15}$, —OC(=O)$R^{12}$, —OC(=O)$OR^{12}$, —C(=O)$NR^{17}R^{18}$, —SH, —S$(C_1-C_6)$alkyl, —$SR^{13}$, —S(=O)$R^{13}$, —S(=O)$_2R^{13}$, —OS(=O)$_2R^{13}$, —S(=O)$_qR^{15}$, —OS(=O)$_qR^{15}$, —S(=O)$_2NR^{17}R^{18}$, —S(=O)$_qNR^{17}R^{18}$, optionally substituted aryl, optionally substituted aryl-$(C_1-C_6)$alkyl, optionally substituted heteroaryl, optionally substituted heteroaryl-$(C_1-C_6)$alkyl, optionally substituted $(C_2-C_9)$heterocyclyl, optionally substituted $(C_2-C_9)$heterocyclyl-$(C_1-C_6)$alkyl, —NH$(CH_2)$, —C(=O)$OR^{14}$, —C(=$NR^{14}$)$NR^{14}_2$, —C(=N—$OR^{14}$)$NR^{14}_2$, —P(=O)$(OR^{14})_2$, and —OP(=O)$(OR^{14})_2$;

Ar is optionally substituted heteroaryl, optionally substituted $(C_{10}-C_{14})$aryl, or

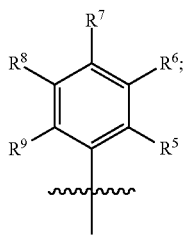

wherein
$R^5$, $R^6$, $R^7$, $R^8$, and $R^9$ are independently selected from the group consisting of —H, —OH, —$OR^{13}$, —$NO_2$, halogen, —CN, —$NR^{10}R^{11}$, —$(CH_2)_mNR^{10}R^{11}$, —O$(CH_2)_mNR^{10}R^{11}$, —$(C_1-C_6)$alkyl, —$(CH_2)_mO(C_1-C_6)$alkyl, —$(C_1-C_6)$alkoxy, —$(C_1-C_6)$perfluoroalkyl, —$(C_1-C_6)$perfluoroalkoxy, —SH, —S$(C_1-C_6)$alkyl, —$SR^{13}$, —S(=O)$R^{15}$, —S(=O)$_2R^{15}$, —C(=O)$R^{15}$, —C(=O)$OR^{15}$, —C(=O)$NR^{17}R^{18}$, —OC(=O)$R^{16}$, —OC(=O)$OR^{12}$, —OC(=O)$NR^{17}R^{18}$, heterocyclyl, optionally substituted heteroaryl, —NH$(CH_2)_mC(=O)OR^{14}$, —OS(=O)$_2R^{16}$, —C(=$NR^{14}$)$NR^{14}_2$, —C(=N—$OR^{14}$)$NR^{14}_2$, —P(=O)$(OR^{14})_2$, and —OP(=O)$(OR^{14})_2$;

each $R^{10}$ and $R^{11}$ is independently selected from the group consisting of —H, —$(C_1-C_6)$alkyl, —$(C_1-C_6)$alkoxy, —C(=O)$R^{12}$, —C(=O)$NR^{17}R^{18}$, —C(=O)$OR^{12}$, —C(=$NR^{14}$)$NR^{17}R^{18}$, $R^{13}$, optionally substituted aryl, optionally substituted heteroaryl, and —C(=$NR^{14}$)$R^{15}$; or $R^{10}$ and $R^{11}$, together with the nitrogen to which they are bound, form an optionally substituted $(C_2-C_5)$heterocycle;

each $R^{12}$ is independently selected from the group consisting of —$(C_1-C_6)$alkyl, and optionally substituted aryl;

each $R^{13}$ is independently selected from the group consisting of optionally substituted aryl and —$(CH_2)_mR^{16}$;

each $R^{14}$ is independently selected from the group consisting of —H and —$(C_1-C_6)$alkyl; or two occurrences of $R^{14}$ bound to the same nitrogen form a $(C_2-C_6)$heterocycle, together with the nitrogen atom to which they are bound;

each $R^{15}$ is independently selected from the group consisting of —H, —$(C_1-C_6)$alkyl, optionally substituted aryl, and $NR^{14}_2$;

each $R^{16}$ is independently selected from the group consisting of —$(C_1-C_6)$alkyl, —$NR^{14}_2$, and $Ar^1$;

each $R^{17}$ and $R^{18}$ is independently selected from the group consisting of —H, —$(C_1-C_6)$alkyl, —$(C_1-C_6)$alkoxy, $R^{13}$, optionally substituted aryl, and optionally substituted heteroaryl; or $R^{17}$ and $R^{18}$, together with the nitrogen to which they are bound, form an optionally substituted $(C_2-C_5)$heterocycle;

m is independently at each occurrence 1, 2, 3, 4, or 5;
p is independently at each occurrence 0, 1, 2, or 3;
q is independently at each occurrence 0, 1, or 2;

each optionally substituted aryl, optionally substituted $(C_{10}-C_{14})$aryl, optionally substituted heteroaryl, optionally substituted aryl-$(C_1-C_6)$alkyl, optionally substituted heteroaryl-$(C_1-C_6)$alkyl, optionally substituted $(C_2-C_9)$heterocyclyl, optionally substituted $(C_2-C_9)$heterocyclyl-$(C_1-C_6)$alkyl, and optionally substituted $(C_2-C_5)$heterocycle is optionally substituted with one or more substituents independently selected from the group consisting of halogen, —CN, —$NR^{14}_2$, —$(CH_2)_mNR^{14}_2$, —O$(CH_2)_mNR^{14}_2$, —$NR^{14}C(=O)(C_1-C_6)$alkyl, —$NR^{14}C(=O)O(C_1-C_6)$alkyl, —$NR^{14}C(=O)NR^{14}_2$, —$NR^{14}C(=NR^{14})NR^{14}_2$, —NH$(CH_2)_mC(=O)OR^{14}$, —OH, —$NO_2$, —$(C_1-C_6)$alkyl, —$(CH_2)_mO(C_1-C_6)$alkyl, —$(C_1-C_6)$alkoxy, —$(C_2-C_6)$alkenyl, —$(C_2-C_6)$alkynyl, —$SR^{14}$, —S(=O)$R^{15}$, —S(=O)$_2R^{15}$, —$NR^{14}S(=O)_2R^{15}$, —$(C_1-C_6)$perfluoroalkyl, —$(C_1-C_6)$perfluoroalkoxy, —C(=O)$R^{14}$, —C(=O)$OR^{14}$, —C(=O)$NR^{14}_2$, —OC(=O)$R^{14}$, —OC(=O)$NR^{14}_2$, —OC(=O)O$(C_1-C_6)$alkyl, —P(=O)$(OR^{14})_2$, —OP(=O)$(OR^{14})_2$, heterocyclyl, and heteroaryl;

$Ar^1$ is a radical according to Formula II:

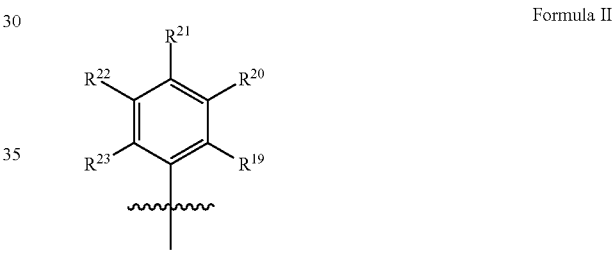

Formula II wherein $R^{19}$, $R^{20}$, $R^{21}$, $R^{22}$, and $R^{23}$ are independently selected from the group consisting of —H, —OH, —$NO_2$, halogen, —CN, —$NR^{10}R^{11}$, —$(CH_2)_mNR^{10}R^{11}$, —O$(CH_2)_mNR^{10}R^{11}$, —$(C_1-C_6)$alkyl, —$(CH_2)_mO(C_1-C_6)$alkyl, —$(C_1-C_6)$alkoxy, —$(C_1-C_6)$perfluoroalkyl, —$(C_1-C_6)$perfluoroalkoxy, —SH, —$SR^{12}$, —S(=O)$R^{15}$, —S(=O)$_2R^{15}$, —C(=O)$R^{15}$, —C(=O)$OR^{15}$, —C(=O)$NR^{17}R^{18}$, —OC(=O)$R^{16}$, —OC(=O)$OR^{12}$, —OC(=O)$NR^{17}R^{18}$, heterocyclyl, optionally substituted heteroaryl, —NH$(CH_2)_mC(=O)OR^{14}$, —OS(=O)$_2R^{16}$, —C(=$NR^{14}$)$NR^{14}_2$, —C(=N—$OR^{14}$)$NR^{14}_2$, —P(=O)$(OR^{14})_2$, and —OP(=O)$(OR^{14})_2$;

provided that:
i) at least one of $R^2$, $R^3$, or $R^4$ is other than hydrogen;
ii) when none of $R^2$, $R^3$, and $R^4$ are —$OR^{13}$, —$NHR^{13}$, —$SR^{13}$, —S(=O)$R^{13}$, or —S(=O)$_2R^{13}$, and Ar is

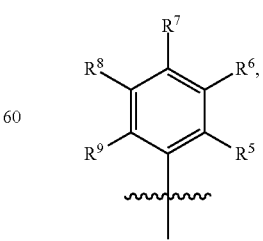

then at least one of $R^6$ and $R^8$ is —$NO_2$ and at least $R^7$ is other than hydrogen or halogen; and iii) when Ar is optionally substituted heteroaryl and none of $R^2$, $R^3$, or $R^4$ are $-OR^{13}$, $-NHR^{13}$, $-SR^{13}$, $-S(=O)R^{13}$, or $-S(=O)_2R^{13}$, then $R^1$ is other than hydrogen.

In certain embodiments of a compound of Formula I, or a salt thereof, n is 0.

In particular embodiments of a compound of Formula I, or a salt thereof, Ar is optionally substituted heteroaryl or

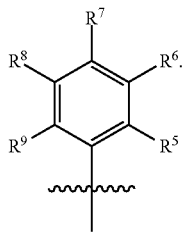

In other embodiments of a compound of Formula I, or a salt thereof, at least one of $R^2$, $R^3$, or $R^4$ is $-OR^{13}$, $-NHR^{13}$, $-SR^{13}$, $-S(=O)R^{13}$, or $-S(=O)_2R^{13}$.

In still other embodiments of a compound of Formula I, or a salt thereof, at least one of $R^2$, $R^3$, or $R^4$ is $-S(=O)_2R^{13}$.

In certain embodiments of a compound of Formula I, or a salt thereof, $R^{13}$ is $-(CH_2)_mR^{16}$.

In some embodiments of a compound of Formula I, or a salt thereof, $R^2$ is $-S(=O)_2R^{13}$ and $R^{13}$ is $-(CH_2)_mR^{16}$.

In a particular embodiment of a compound of Formula I, or a salt thereof, $R^{16}$ is $Ar^1$. In certain embodiments of a compound of Formula I, or a salt thereof, $Ar^1$ is 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-difluorophenyl, 2,4-difluorophenyl, 2,5-difluorophenyl, 2,6-difluorophenyl, 3,4-difluorophenyl, 3,5-difluorophenyl, 2,3-diiodophenyl, 2,4-diiodophenyl, 2,5-diiodophenyl, 2,6-diiodophenyl, 3,4-diiodophenyl, 3,5-diiodophenyl, 2-chloro-3-bromophenyl, 2-chloro-4-bromophenyl, 2-chloro-5-bromophenyl, 2-chloro-6-bromophenyl, 3-chloro-4-bromophenyl, 3-chloro-5-bromophenyl, 4-chloro-5-bromophenyl, 2-bromo-3-chlorophenyl, 2-bromo-4-chlorophenyl, 2-bromo-5-chlorophenyl, 3-bromo-4-chlorophenyl, 2-chloro-3-fluorophenyl, 2-chloro-4-fluorophenyl, 2-chloro-5-fluorophenyl, 2-chloro-6-fluorophenyl, 3-chloro-4-fluorophenyl, 3-chloro-5-fluorophenyl, 4-chloro-5-fluorophenyl, 2-fluoro-3-chlorophenyl, 2-fluoro-4-chlorophenyl, 2-fluoro-5-chlorophenyl, 3-fluoro-4-chlorophenyl, 2-chloro-3-iodophenyl, 2-chloro-4-iodophenyl, 2-chloro-5-iodophenyl, 2-chloro-6-iodophenyl, 3-chloro-4-iodophenyl, 3-chloro-5-iodophenyl, 4-chloro-5-iodophenyl, 2-iodo-3-chlorophenyl, 2-iodo-4-chlorophenyl, 2-iodo-5-chlorophenyl, 3-iodo-4-chlorophenyl, 2-bromo-3-fluorophenyl, 2-bromo-4-fluorophenyl, 2-bromo-5-fluorophenyl, 2-bromo-6-fluorophenyl, 3-bromo-4-fluorophenyl, 3-bromo-5-fluorophenyl, 4-bromo-5-fluorophenyl, 2-fluoro-3-bromophenyl, 2-fluoro-4-bromophenyl, 2-fluoro-5-bromophenyl, 3-fluoro-4-bromophenyl, 2-bromo-3-iodophenyl, 2-bromo-4-iodophenyl, 2-bromo-5-iodophenyl, 2-bromo-6-iodophenyl, 3-bromo-4-iodophenyl, 3-bromo-5-iodophenyl, 4-bromo-5-iodophenyl, 2-iodo-3-bromophenyl, 2-iodo-4-bromophenyl, 2-iodo-5-bromophenyl, 3-iodo-4-bromophenyl, 2-fluoro-3-iodophenyl, 2-fluoro-4-iodophenyl, 2-fluoro-5-iodophenyl, 2-fluoro-6-iodophenyl, 3-fluoro-4-iodophenyl, 3-fluoro-5-iodophenyl, 4-fluoro-5-iodophenyl, 2-iodo-3-fluorophenyl, 2-iodo-4-fluorophenyl, 2-iodo-5-fluorophenyl, or 3-iodo-4-fluorophenyl.

In particular embodiments, $Ar^1$ is 2,6-dichlorophenyl.

In certain embodiments of a compound of Formula I, or a salt thereof, Ar is

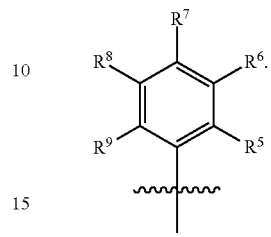

In other embodiments, a compound of Formula I, or a salt thereof, is selected from the group consisting of (Z)-4-((6-((2,6-dichlorobenzyl)sulfonyl)-3-oxo-3,4-dihydro-2H-benzo[b][1,4]thiazin-2-ylidene)methyl)-2-nitrophenyl acetate; (Z)-4-((6-((2,6-dichlorobenzyl)sulfonyl)-3-oxo-3,4-dihydro-2H-benzo[b][1,4]thiazin-2-ylidene)methyl)phenyl acetate; (Z)-2-benzylidene-6-((2,6-dichlorobenzyl)sulfonyl)-2H-benzo[b][1,4]thiazin-3(4H)-one; (Z)-6-((2,6-dichlorobenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dichlorobenzyl)sulfonyl)-2H-benzo[b][1,4]thiazin-3(4H)-one; (Z)-6-((2,6-dichlorobenzyl)sulfonyl)-2-(4-(4-methylpiperazin-1-yl)benzylidene)-2H-benzo[b][1,4]thiazin-3(4H)-one; (Z)-6-((2,6-dichlorobenzyl)sulfonyl)-2-(4-nitrobenzylidene)-2H-benzo[b][1,4]thiazin-3(4H)-one; (Z)-2-(4-aminobenzylidene)-6-((2,6-dichlorobenzyl)sulfonyl)-2H-benzo[b][1,4]thiazin-3(4H)-one; (Z)-6-((2,6-dichlorobenzyl)sulfonyl)-2-(4-fluorobenzylidene)-2H-benzo[b][1,4]thiazin-3(4H)-one; (Z)-2-(4-chlorobenzylidene)-6-((2,6-dichlorobenzyl)sulfonyl)-2H-benzo[b][1,4]thiazin-3(4H)-one; (Z)-2-(4-bromobenzylidene)-6-((2,6-dichlorobenzyl)sulfonyl)-2H-benzo[b][1,4]thiazin-3(4H)-one; (Z)-6-((2,6-dichlorobenzyl)sulfonyl)-2-(4-methoxybenzylidene)-2H-benzo[b][1,4]thiazin-3(4H)-one; (Z)-6-((2,6-dichlorobenzyl)sulfonyl)-2-(4-methylbenzylidene)-2H-benzo[b][1,4]thiazin-3(4H)-one; (Z)-6-((2,6-dichlorobenzyl)sulfonyl)-2-(2,4,6-trimethoxybenzylidene)-2H-benzo[b][1,4]thiazin-3(4H)-one; (Z)-6-((2,6-dichlorobenzyl)sulfonyl)-2-(2,4-dichlorobenzylidene)-2H-benzo[b][1,4]thiazin-3(4H)-one; (Z)-6-((2,6-dichlorobenzyl)sulfonyl)-2-(2,4,6-trifluorobenzylidene)-2H-benzo[b][1,4]thiazin-3(4H)-one; (Z)-methyl 2-((4-((6-((2,6-dichlorobenzyl)sulfonyl)-3-oxo-3,4-dihydro-2H-benzo[b][1,4]thiazin-2-ylidene)methyl)phenyl)amino)acetate; (Z)-2-((4-(((6-((2,6-dichlorobenzyl)sulfonyl)-3-oxo-3,4-dihydro-2H-benzo[b][1,4]thiazin-2-ylidene)methyl)phenyl)amino)acetic acid; (Z)-6-((2,6-dichlorobenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dichlorobenzyl)sulfonyl)-2H-benzo[b][1,4]thiazin-3(4H)-one; (Z)-6-((2,6-dichlorobenzyl)sulfonyl)-2-(2,4-difluorobenzylidene)-2H-benzo[b][1,4]thiazin-3(4H)-one; (Z)-6-((2,6-dichlorobenzyl)sulfonyl)-2-(2,4,6-trifluorobenzylidene)-2H-benzo[b][1,4]thiazin-3(4H)-one; (Z)-methyl 4-((6-((2,6-dichlorobenzyl)sulfonyl)-3-oxo-3,4-dihydro-2H-benzo[b][1,4]thiazin-2-ylidene)methyl)benzoate; (Z)- methyl 4-((6-((2,6-dichlorobenzyl)sulfonyl)-3-oxo-3,4-dihydro-2H-benzo[b][1,4]thiazin-2-ylidene)methyl)-3-nitrobenzoate; (Z)-4-((6-((2,6-dichlorobenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dichlorobenzyl)sulfonyl)-2H-benzo[b][1,4]thiazin-3(4H)-one; (Z)-2-(4-(benzyloxy)-3-nitrobenzylidene)-6-((2,6-dichlorobenzyl)sulfonyl)-2H-benzo[b][1,4]thiazin-3(4H)-one; and (Z)-6-((2,6-dichlorobenzyl)sulfonyl)-2-(4-hydroxy-3-nitrobenzylidene)-2H-benzo[b][1,4]thiazin-3(4H)-one.

In certain embodiments of a compound of Formula I, or a salt thereof, Ar is optionally substituted heteroaryl.

In a particular embodiment a compound of Formula I, or a salt thereof, is selected from the group consisting of (Z)-6-((2,6-dichlorobenzyl)sulfonyl)-2-((2-(methylthio)pyrimidin-4-yl)methylene)-2H-benzo[b][1,4]thiazin-3(4H)-one; (Z)-6-((2,6-dichlorobenzyl)sulfonyl)-2-((2-morpholinopyrimidin-4-yl)methylene)-2H-benzo[b][1,4]thiazin-3(4H)-one; (Z)-2-((1H-indol-3-yl)methylene)-6-((2,6-dichlorobenzyl)sulfonyl)-2H-benzo[b][1,4]thiazin-3(4H)-one; (Z)-6-((2,6-dichlorobenzyl)sulfonyl)-2-(thiophen-2-ylmethylene)-2H-benzo[b][1,4]thiazin-3(4H)-one; (Z)-2-((1H-pyrrol-3-yl)methylene)-6-((2,6-dichlorobenzyl)sulfonyl)-2H-benzo[b][1,4]thiazin-3(4H)-one; and (Z)-2-((1-acetyl-1H-indol-3-yl)methylene)-6-((2,6-dichlorobenzyl)sulfonyl)-2H-benzo[b][1,4]thiazin-3(4H)-one.

In certain embodiments of a compound of Formula I, at least one of $R^6$ and $R^8$ is —$NO_2$ and at least $R^7$ is other than hydrogen or halogen.

In some embodiments, a compound of Formula I, or a salt thereof, is selected from the group consisting of (Z)-4-((6-chloro-3-oxo-3,4-dihydro-2H-benzo[b][1,4]thiazin-2-ylidene)methyl)-2-nitrophenyl acetate; (Z)-4-((7-methoxy-3-oxo-3,4-dihydro-2H-benzo[b][1,4]thiazin-2-ylidene)methyl)-2-nitrophenyl acetate; (Z)-4-((7-bromo-3-oxo-3,4-dihydro-2H-benzo[b][1,4]thiazin-2-ylidene)methyl)-2-nitrophenyl acetate; (Z)-4-((7-methyl-3-oxo-3,4-dihydro-2H-benzo[b][1,4]thiazin-2-ylidene)methyl)-2-nitrophenyl acetate; (Z)-2-(4-acetoxy-3-nitrobenzylidene)-3-oxo-3,4-dihydro-2H-benzo[b][1,4]thiazine-7-carboxylic acid; (Z)-4-((7-fluoro-3-oxo-3,4-dihydro-2H-benzo[b][1,4]thiazin-2-ylidene)methyl)-2-nitrophenyl acetate; (Z)-4-((6-fluoro-3-oxo-3,4-dihydro-2H-benzo[b][1,4]thiazin-2-ylidene)methyl)-2-nitrophenyl acetate; (Z)-4-((4-acetyl-7-methoxy-3-oxo-3,4-dihydro-2H-benzo[b][1,4]thiazin-2-ylidene)methyl)-2-nitrophenyl acetate; (Z)-2-(4-(benzyloxy)-3-nitrobenzylidene)-7-fluoro-2H-benzo[b][1,4]thiazin-3(4H)-one; and (Z)-7-fluoro-2-(4-hydroxy-3-nitrobenzylidene)-2H-benzo[b][1,4]thiazin-3(4H)-one.

In other embodiments, a compound of Formula I, or a salt thereof, is selected from the group consisting of (Z)-4-((6-((2,6-dibromobenzyl)sulfonyl)-3-oxo-3,4-dihydro-2H-benzo[b][1,4]thiazin-2-ylidene)methyl)-2-nitrophenyl acetate; (Z)-4-((6-((2,6-dibromobenzyl)sulfonyl)-3-oxo-3,4-dihydro-2H-benzo[b][1,4]thiazin-2-ylidene)methyl)phenyl acetate; (Z)-2-benzylidene-6-((2,6-dibromobenzyl)sulfonyl)-2H-benzo[b][1,4]thiazin-3(4H)-one; (Z)-6-((2,6-dibromobenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-(4-methylpiperazin-1-yl)benzylidene)-2H-benzo[b][1,4]thiazin-3(4H)-one; (Z)-6-((2,6-dibromobenzyl)sulfonyl)-2-(4-nitrobenzylidene)-2H-benzo[b][1,4]thiazin-3(4H)-one; (Z)-2-(4-aminobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-fluorobenzylidene)-2H-benzo[b][1,4]thiazin-3(4H)-one; (Z)-2-(4-chlorobenzylidene)-6-((2,6-dibromobenzyl)sulfonyl)-2H-benzo[b][1,4]thiazin-3(4H)-one; (Z)-2-(4-bromobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-methoxybenzylidene)-2H-benzo[b][1,4]thiazin-3(4H)-one; (Z)-6-((2,6-dibromobenzyl)sulfonyl)-2-(4-methylbenzylidene)-2H-benzo[b][1,4]thiazin-3(4H)-one; (Z)-6-((2,6-dibromobenzyl)sulfonyl)-2-(2,4,6-trimethoxybenzylidene)-2H-benzo[b][1,4]thiazin-3(4H)-one; (Z)-6-((2,6-dibromobenzyl)sulfonyl)-2-(2,4-dibromobenzylidene)-2H-benzo[b][1,4]thiazin-3(4H)-one; (Z)-6-((2,6-dibromobenzyl)sulfonyl)-2-(2,4,6-trifluorobenzylidene)-2H-benzo[b][1,4]thiazin-3(4H)-one; (Z)-methyl 2-((4-((6-((2,6-dibromobenzyl)sulfonyl)-3-oxo-3,4-dihydro-2H-benzo[b][1,4]thiazin-2-ylidene)methyl)phenyl)amino)acetate; (Z)-2-((4-((6-((2,6-dibromobenzyl)sulfonyl)-3-oxo-3,4-dihydro-2H-benzo[b][1,4]thiazin-2-ylidene)methyl)phenyl)amino)acetic acid; (Z)-6-((2,6-dibromobenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(2,4-difluorobenzylidene)-2H-benzo[b][1,4]thiazin-3(4H)-one; (Z)-6-((2,6-dibromobenzyl)sulfonyl)-2-(2,4,6-trifluorobenzylidene)-2H-benzo[b][1,4]thiazin-3(4H)-one; (Z)-methyl 4-((6-((2,6-dibromobenzyl)sulfonyl)-3-oxo-3,4-dihydro-2H-benzo[b][1,4]thiazin-2-ylidene)methyl)benzoate; (Z)-methyl 4-((6-((2,6-dibromobenzyl)sulfonyl)-3-oxo-3,4-dihydro-2H-benzo[b][1,4]thiazin-2-ylidene)methyl)-3-nitrobenzoate; (Z)-4-((6-((2,6-dibromobenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dibromobenzyl)sulfonyl)-2H-benzo[b][1,4]thiazin-3(4H)-one; (Z)-2-(4-(benzyloxy)-3-nitrobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-hydroxy-3-nitrobenzylidene)-2H-benzo[b][1,4]thiazin-3(4H)-one; (Z)-4-((6-((2,6-difluorobenzyl)sulfonyl)-3-oxo-3,4-dihydro-2H-benzo[b][1,4]thiazin-2-ylidene)methyl)-2-nitrophenyl acetate; (Z)-4-((6-((2,6-difluorobenzyl)sulfonyl)-3-oxo-3,4-dihydro-2H-benzo[b][1,4]thiazin-2-ylidene)methyl)phenyl acetate; (Z)-2-benzylidene-6-((2,6-difluorobenzyl)sulfonyl)-2H-benzo[b][1,4]thiazin-3(4H)-one; (Z)-6-((2,6-difluorobenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-(4-methylpiperazin-1-yl)benzylidene)-2H-benzo[b][1,4]thiazin-3(4H)-one; (Z)-6-((2,6-difluorobenzyl)sulfonyl)-2-(4-nitrobenzylidene)-2H-benzo[b][1,4]thiazin-3(4H)-one; (Z)-2-(4-aminobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-fluorobenzylidene)-2H-benzo[b][1,4]thiazin-3(4H)-one; (Z)-2-(4-chlorobenzylidene)-6-((2,6-difluorobenzyl)sulfonyl)-2H-benzo[b][1,4]thiazin-3(4H)-one; (Z)-2-(4-bromobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-methoxybenzylidene)-2H-benzo[b][1,4]thiazin-3(4H)-one; (Z)-6-((2,6-difluorobenzyl)sulfonyl)-2-(4-methylbenzylidene)-2H-benzo[b][1,4]thiazin-3(4H)-one; (Z)-6-((2,6-difluorobenzyl)sulfonyl)-2-(2,4,6-trimethoxybenzylidene)-2H-benzo[b][1,4]thiazin-3(4H)-one; (Z)-6-((2,6-difluorobenzyl)sulfonyl)-2-(2,4-difluorobenzylidene)-2H- benzo[b][1,4]thiazin-3(4H)-one; (Z)-6-((2,6-difluorobenzyl)sulfonyl)-2-(2,4,6-trifluorobenzylidene)-2H-benzo[b][1,4]thiazin-3(4H)-one; (Z)-methyl 2-((4-((6-((2,6-difluorobenzyl)sulfonyl)-3-oxo-3,4-dihydro-2H-benzo[b][1,4]thiazin-2-ylidene)methyl)phenyl)amino)acetate; (Z)-2-((4-((6-((2,6-difluorobenzyl)sulfonyl)-3-oxo-3,4-dihydro-2H-benzo[b][1,4]thiazin-2-ylidene)methyl)phenyl)amino)acetic acid; (Z)-6-((2,6-difluorobenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(2,4-difluorobenzylidene)-2H-benzo[b][1,4]thiazin-3(4H)-one; (Z)-6-((2,6-difluorobenzyl)sulfonyl)-2-(2,4,6-trifluorobenzylidene)-2H-benzo[b][1,4]thiazin-3(4H)-one; (Z)-methyl 4-((6-((2,6-difluorobenzyl)sulfonyl)-3-oxo-3,4-dihydro-2H-benzo[b][1,4]thiazin-2-ylidene)methyl)benzoate; (Z)-methyl 4-((6-((2,6-difluorobenzyl)sulfonyl)-3-oxo-3,4-dihydro-2H-benzo[b][1,4]thiazin-2-ylidene)methyl)-3-nitrobenzoate; (Z)-4-((6-((2,6-difluorobenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-difluorobenzyl)sulfonyl)-2H-benzo[b][1,4]thiazin-3(4H)-one; (Z)-2-(4-(benzyloxy)-3-nitrobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-hydroxy-3-nitrobenzylidene)-2H-benzo[b][1,4]thiazin-3(4H)-one; (Z)-4-((6-((2,6-dimethylbenzyl)sulfonyl)-3-oxo-3,4-dihydro-2H-benzo[b][1,4]thiazin-2-ylidene)methyl)-2-nitrophenyl acetate; (Z)-4-((6-((2,6-dimethylbenzyl)sulfonyl)-3-oxo-3,4-dihydro-2H-benzo[b][1,4]thiazin-2-ylidene)methyl)phenyl acetate; (Z)-2-benzylidene-6-((2,6-dimethylbenzyl)sulfonyl)-2H-benzo[b][1,4]thiazin-3(4H)-one; (Z)-6-((2,6-dimethylbenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-(4-methylpiperazin-1-yl)benzylidene)-2H-benzo[b][1,4]thiazin-3(4H)-one; (Z)-6-((2,6-dimethylbenzyl)sulfonyl)-2-(4-nitrobenzylidene)-2H-benzo[b][1,4]thiazin-3(4H)-one; (Z)-2-(4-aminobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-fluorobenzylidene)-2H-benzo[b][1,4]thiazin-3(4H)-one; (Z)-2-(4-chlorobenzylidene)-6-((2,6-dimethylbenzyl)sulfonyl)-2H-benzo[b][1,4]thiazin-3(4H)-one; (Z)-2-(4-bromobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-methoxybenzylidene)-2H-benzo[b][1,4]thiazin-3(4H)-one; (Z)-6-((2,6-dimethylbenzyl)sulfonyl)-2-(4-methylbenzylidene)-2H-benzo[b][1,4]thiazin-3(4H)-one; (Z)-6-((2,6-dimethylbenzyl)sulfonyl)-2-(2,4,6-trimethoxybenzylidene)-2H-benzo[b][1,4]thiazin-3(4H)-one; (Z)-6-((2,6-dimethylbenzyl)sulfonyl)-2-(2,4-dimethylbenzylidene)-2H-benzo[b][1,4]thiazin-3(4H)-one; (Z)-6-((2,6-dimethylbenzyl)sulfonyl)-2-(2,4,6-trifluorobenzylidene)-2H-benzo[b][1,4]thiazin-3(4H)-one; (Z)-methyl 2-((4-((6-((2,6-dimethylbenzyl)sulfonyl)-3-oxo-3,4-dihydro-2H-benzo[b][1,4]thiazin-2-ylidene)methyl)phenyl)amino)acetate; (Z)-2-((4-((6-((2,6-dimethylbenzyl)sulfonyl)-3-oxo-3,4-dihydro-2H-benzo[b][1,4]thiazin-2-ylidene)methyl)phenyl)amino)acetic acid; (Z)-6-((2,6-dimethylbenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(2,4-difluorobenzylidene)-2H-benzo[b][1,4]thiazin-3(4H)-one;

(Z)-6-((2,6-dimethylbenzyl)sulfonyl)-2-(2,4,6-trifluorobenzylidene)-2H-benzo[b][1,4]thiazin-3(4H)-one; (Z)-methyl 4-((6-((2,6-dimethylbenzyl)sulfonyl)-3-oxo-3,4-dihydro-2H-benzo[b][1,4]thiazin-2-ylidene)methyl)benzoate; (Z)-methyl 4-((6-((2,6-dimethylbenzyl)sulfonyl)-3-oxo-3,4-dihydro-2H-benzo[b][1,4]thiazin-2-ylidene)methyl)-3-nitrobenzoate; (Z)-4-((6-((2,6-dimethylbenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dimethylbenzyl)sulfonyl)-2H-benzo[b][1,4]thiazin-3(4H)-one; (Z)-2-(4-(benzyloxy)-3-nitrobenzylidene)-6-((2,6-dimethylbenzyl)sulfonyl)-2H-benzo[b][1,4]thiazin-3(4H)-one; and (Z)-6-((2,6-dimethylbenzyl)sulfonyl)-2-(4-hydroxy-3-nitrobenzylidene)-2H-benzo[b][1,4]thiazin-3(4H)-one; (Z)-4-((6-((2,6-dimethoxybenzyl)sulfonyl)-3-oxo-3,4-dihydro-2H-benzo[b][1,4]thiazin-2-ylidene)methyl)-2-nitrophenyl acetate; (Z)-4-((6-((2,6-dimethoxybenzyl)sulfonyl)-3-oxo-3,4-dihydro-2H-benzo[b][1,4]thiazin-2-ylidene)methyl)phenyl acetate; (Z)-2-benzylidene-6-((2,6-dimethoxybenzyl)sulfonyl)-2H-benzo[b][1,4]thiazin-3(4H)-one; (Z)-6-((2,6-dimethoxybenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-(4-methylpiperazin-1-yl)benzylidene)-2H-benzo[b][1,4]thiazin-3(4H)-one; (Z)-6-((2,6-dimethoxybenzyl)sulfonyl)-2-(4-nitrobenzylidene)-2H-benzo[b][1,4]thiazin-3(4H)-one; (Z)-2-(4-aminobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-fluorobenzylidene)-2H-benzo[b][1,4]thiazin-3(4H)-one; (Z)-2-(4-chlorobenzylidene)-6-((2,6-dimethoxybenzyl)sulfonyl)-2H-benzo[b][1,4]thiazin-3(4H)-one; (Z)-2-(4-bromobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-methoxybenzylidene)-2H-benzo[b][1,4]thiazin-3(4H)-one; (Z)-6-((2,6-dimethoxybenzyl)sulfonyl)-2-(4-methylbenzylidene)-2H-benzo[b][1,4]thiazin-3(4H)-one; (Z)-6-((2,6-dimethoxybenzyl)sulfonyl)-2-(2,4,6-trimethoxybenzylidene)-2H-benzo[b][1,4]thiazin-3(4H)-one; (Z)-6-((2,6-dimethoxybenzyl)sulfonyl)-2-(2,4-dimethoxybenzylidene)-2H-benzo[b][1,4]thiazin-3(4H)-one; (Z)-6-((2,6-dimethoxybenzyl)sulfonyl)-2-(2,4,6-trifluorobenzylidene)-2H-benzo[b][1,4]thiazin-3(4H)-one; (Z)-methyl 2-((4-((6-((2,6-dimethoxybenzyl)sulfonyl)-3-oxo-3,4-dihydro-2H-benzo[b][1,4]thiazin-2-ylidene)methyl)phenyl)amino)acetate; (Z)-2-((4-((6-((2,6-dimethoxybenzyl)sulfonyl)-3-oxo-3,4-dihydro-2H-benzo[b][1,4]thiazin-2-ylidene)methyl)phenyl)amino)acetic acid; (Z)-6-((2,6-dimethoxybenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(2,4-difluorobenzylidene)-2H-benzo[b][1,4]thiazin-3(4H)-one; (Z)-6-((2,6-dimethoxybenzyl)sulfonyl)-2-(2,4,6-trifluorobenzylidene)-2H-benzo[b][1,4]thiazin-3(4H)-one; (Z)-methyl 4-((6-((2,6-dimethoxybenzyl)sulfonyl)-3-oxo-3,4-dihydro-2H-benzo[b][1,4]thiazin-2-ylidene)methyl)benzoate; (Z)-methyl 4-((6-((2,6-dimethoxybenzyl)sulfonyl)-3-oxo-3,4-dihydro-2H-benzo[b][1,4]thiazin-2-ylidene)methyl)-3-nitrobenzoate; (Z)-4-((6-((2,6-dimethoxybenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dimethoxybenzyl)sulfonyl)-2H-benzo[b][1,4]thiazin-3(4H)-one; (Z)-2-(4-(benzyloxy)-3-nitrobenzylidene)-6-((2,6-dimethoxybenzyl)sulfonyl)-2H-benzo[b][1,4]thiazin-3(4H)-one; and (Z)-6-((2,6-dimethoxybenzyl)sulfonyl)-2-(4-hydroxy-3-nitrobenzylidene)-2H-benzo[b][1,4]thiazin-3(4H)-one.

The present invention further provides a process for preparing a compound of Formula I. In certain embodiments, the process for preparing a compound of Formula I comprises condensing an aldehyde of Formula III

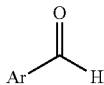

Formula III with a compound according to Formula IV:

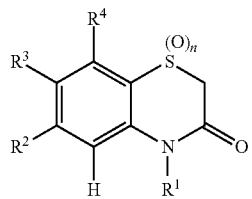

Formula IV in a reaction mixture, wherein Ar, $R^1$, $R^2$, $R^3$, $R^4$, and n, are as defined elsewhere herein. The method further provides for isolating from the reaction mixture the compound of Formula I, or a salt thereof.

In certain embodiments, the condensation takes place in the presence of one or more of an anhydride and a base. In particular embodiments, the anhydride is acetic anhydride and the base is triethylamine.

In other embodiments of the process described herein, a compound of Formula IV is prepared by functionalizing 2H-1,4-Benzothiazin-3(4H)-one, or a derivative thereof, with chlorosulfonic acid to give 3-oxo-3,4-dihydro-2H-benzo[b][1,4]thiazine-6-sulfonyl chloride; reacting said 3-oxo-3,4-dihydro-2H-benzo[b][1,4]thiazine-6-sulfonyl chloride with Zn to form a reactive Zn complex; and reacting said reactive Zn complex with a compound of Formula V:

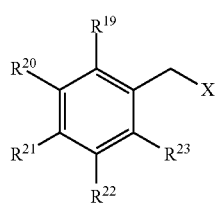

Formula V to give a compound of Formula IV, wherein $R^{19}$, $R^{20}$, $R^{21}$, $R^{22}$, and $R^{23}$ are as defined elsewhere herein, and X is a leaving group.

In still another embodiment of a process described herein, a compound according to Formula IV is prepared by reacting compound A:

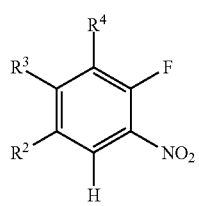

A with $HSCH_2CO_2R$, wherein R is H or $(C_1$-$C_6)$alkyl and $R^2$, $R^3$, and $R^4$ are as defined elsewhere herein, to form compound B:

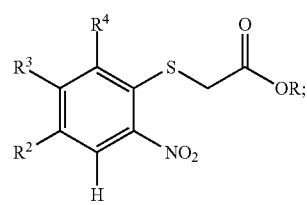

B and reducing the nitro group of compound B to give said compound according to Formula IV.

In certain embodiments, reducing the nitro group of compound B comprises treating compound B with Zn and acetic acid. In other embodiments, reducing the nitro group of compound B comprises treating compound B with $Na_2S_2O_4$.

The present disclosure further provides an antibody conjugate of the formula:

I-L-Ab or a salt thereof, wherein I is a compound according to Formula I as defined above; Ab is an antibody; and -L- is a single bond or a linking group covalently linking said compound of Formula I to said antibody.

In particular embodiments of the antibody conjugate described herein, the antibody is a monoclonal antibody or a monospecific polyclonal antibody. In certain embodiments, the antibody is a tumor specific antibody.

The present disclosure further provides a pharmaceutical composition comprising a pharmaceutically acceptable carrier and a compound of Formula I, or a pharmaceutically acceptable salt thereof.

In certain embodiments, the present disclosure provides a pharmaceutical composition comprising a pharmaceutically acceptable carrier and an antibody conjugate I-L-Ab, or a pharmaceutically acceptable salt thereof, as set forth previously herein.

The present disclosure further provides a method of treating an individual suffering from a cellular proliferative disorder, comprising administering to the individual an effective amount of at least one compound of Formula I, or a pharmaceutically acceptable salt thereof.

In particular embodiments, the cellular proliferative disorder is selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy, non cancerous lymphocellular proliferative disorders, and cancer.

In particular embodiments, the cellular proliferative disorder is cancer. In certain embodiments, the cancer is selected from the group consisting of ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

In certain embodiments, the cellular proliferative disorder is cancer, the compound is (Z)-6-((2,6-dichlorobenzyl)sulfonyl)-2-(4-hydroxy-3-nitrobenzylidene)-2H-benzo[b][1,4]thiazin-3(4H)-one or pharmaceutically acceptable salt thereof, and the activity of one or more kinases selected from the group consisting of casein kinase 2 (CK2), cyclin-dependent kinase 9 (CDK9) and PIM1 is inhibited in cancer cells of the individual.

The present disclosure further provides a method of inducing apoptosis of cancer cells in an individual afflicted with cancer, comprising administering to the individual an effective amount of at least one compound of Formula I, or a pharmaceutically acceptable salt thereof.

In certain embodiments of the method of inducing apoptosis of cancer cells in an individual afflicted with cancer, the compound is (2)-6-((2,6-dichlorobenzyl)sulfonyl)-2-(4-hydroxy-3-nitrobenzylidene)-2H-benzo[b][1,4]thiazin-3(4H)-one or pharmaceutically acceptable salt thereof, and the activity of one or more kinases selected from the group consisting of CK2, CDK9 and PIM1 is inhibited in cancer cells of the individual.

In certain embodiments, the cancer cells are tumor cells. In particular embodiments, the tumor cells are selected from the group consisting of ovarian, cervical, breast, prostate, testicular, lung, renal, colorectal, skin and brain tumor cells.

The present disclosure further provides a method of treating an individual suffering from a cellular proliferative disorder, comprising administering to the individual an effective amount of at least one antibody conjugate of the formula I-L-Ab, or pharmaceutically acceptable salt thereof, as defined elsewhere herein.

The present disclosure further includes a method of inducing apoptosis of cancer cells in an individual afflicted with cancer, comprising administering to the individual an effective amount of at least one antibody conjugate of the formula I-L-Ab, or a pharmaceutically acceptable salt thereof, as defined elsewhere herein.

In particular embodiments of the aforesaid methods and compositions, the compound is (Z)-6-((2,6-dichlorobenzyl)sulfonyl)-2-(4-hydroxy-3-nitrobenzylidene)-2H-benzo[b][1,4]thiazin-3(4H)-one, or pharmaceutically acceptable salt thereof.

In certain embodiments, the invention is a compound of Formula I, or salt thereof, for use in medicine. In other embodiments, the invention is a compound of Formula I, or a salt thereof, for treatment of a cellular proliferative disorder. In other embodiments, the invention provides a use of a compound according to Formula I, or a salt thereof, for preparation of a medicament for treatment of a cellular proliferative disorder. The present invention further provides a medicament for treatment of a cellular proliferative disorder, containing a compound of Formula I.

In some embodiments, the invention is an antibody conjugate of a compound of Formula I, or salt thereof, for use in medicine. In other embodiments, the invention is an antibody conjugate of a compound of Formula I, or a salt thereof, for treatment of a cellular proliferative disorder. In other embodiments, the invention provides a use of an antibody conjugate of a compound according to Formula I, or a salt thereof, for preparation of a medicament for treatment of a cellular proliferative disorder. The present invention further provides a medicament for treatment of a cellular proliferative disorder, containing an antibody conjugate of a compound of Formula I.

BRIEF DESCRIPTION OF THE DRAWINGS

The foregoing summary, as well as the following detailed description the embodiments, will be better understood when read in conjunction with the appended drawings. For the purpose of illustration, there are shown in the drawings some embodiments which may be preferable. It should be understood, however, that the embodiments depicted are not limited to the precise arrangements and instrumentalities shown.

FIG. 1 is a synthetic scheme for preparing an intermediate useful for the preparation of a compound according to Formula I.

DETAILED DESCRIPTION OF THE INVENTION

The compounds and compositions of the invention are believed to selectively inhibit proliferation of cancer cells, and kill various tumor cell types without killing (or with reduced killing of) normal cells. Cancer cells are killed at concentrations where normal cells may be temporarily growth-arrested but not killed.

The compounds of the invention are believed to inhibit the proliferation of tumor cells, and for some compounds, induce cell death. Cell death results from the induction of apoptosis. The compounds are believed effective against a broad range of tumor types, including but not limited to the following: ovarian cancer, breast cancer, prostate cancer, lung cancer, renal cancer, colorectal cancer, brain cancer and leukemia.

The compounds are also believed useful in the treatment of non-cancer cellular proliferative disorders, including but not limited to the following: hemangiomatosis in newborn, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis and cirrhosis.

At least one compound of the invention, (Z)-6-((2,6-dichlorobenzyl)sulfonyl)-2-(4-hydroxy-3-nitrobenzylidene)-2H-benzo[b][1,4]thiazin-3(4H)-one (Compound 42), inhibits the activity of at least three kinases—casein kinase 2 (CK2), cyclin-dependent kinase 9 (CDK9) and PIM1—that have been implicated in tumorigenesis and cancer progression. The aforesaid compound is to believed to possess particular utility in inhibiting the oncogenic activity of PIM1, in inhibiting the ability of CK2 to induce malignant transformation and in enhancing apoptosis of cancer cells otherwise suppressed by CK2, and inhibiting the pro-cancer growth activity of CDK9, particularly in cancers involving high levels of replication stress.

At least Compound 42 also induces cell cycle arrest in cancer cells. MDA.MB-231 breast cancer cells treated with increasing concentrations Compound 42

Without wishing to be bound by any mechanism of action, it is believed that Compound 42 competes with the ATP/GTP phosphate donor in the ATP pocket in the structure of CK2. The crystal structure of Compound 42 bound to CK2 demonstrates that the drug mimics not only the shape and electrostatics of GTP/ATP, but also the hydration patterns of GTP/ATP (data not shown).

I. Definitions

A. General

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The expression "effective amount", when used to describe therapy to an individual suffering from a cancer or other cellular proliferative disorder, refers to the amount of a compound according to Formula I that inhibits the abnormal growth or proliferation, or alternatively induces apoptosis of cancer cells, preferably tumor cells, resulting in a therapeutically useful and selective cytotoxic effect on proliferative cells.

The term "cellular proliferative disorder" means a disorder wherein unwanted cell proliferation of one or more subsets of cells in a multicellular organism occurs. In some such disorders, cells are made by the organism at an atypically accelerated rate.

B. Chemical

In the following paragraphs some of the definitions include examples. The examples are intended to be illustrative, and not limiting.

The term "alkyl", by itself or as part of another substituent means, unless otherwise stated, a straight, branched (chiral or achiral) or cyclic chain hydrocarbon having the number of carbon atoms designated (e.g. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Most preferred is ($C_1$-$C_3$)alkyl, particularly ethyl, methyl and isopropyl.

The term "alkenyl" employed alone or in combination with other terms, means, unless otherwise stated, a stable mono-unsaturated or di-unsaturated straight chain, branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl and the higher homologs and isomers. A functional group representing an alkene is exemplified by —CH=CH—CH$_2$—.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The terms "halo" or "halogen" by themselves or as part of another substituent mean, unless otherwise stated, a fluorine, chlorine, bromine, or iodine atom, preferably, fluorine, chlorine, or bromine, more preferably, fluorine or chlorine.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —CF$_3$.

The term "($C_x$-$C_y$)perfluoroalkoxy," wherein x<y, means an alkoxy group with a minimum of x carbon atoms and a maximum of y carbon atoms, wherein all hydrogen atoms are replaced by fluorine atoms. Preferred is —($C_1$-$C_6$)perfluoroalkoxy, more preferred is —($C_1$-$C_3$)perfluoroalkoxy, most preferred is —OCF$_3$.

The term "aromatic" refers to a carbocycle or heterocycle having one or more polyunsaturated rings having aromatic character (i.e. having (4n+2) delocalized π (pi) electrons where n is an integer).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

The term "optionally substituted aryl-($C_1$-$C_3$)alkyl" means a functional group wherein a one to three carbon alkylene chain is attached to an optionally substituted aryl group, e.g., —CH$_2$CH$_2$-phenyl. Similarly, the term "optionally substituted heteroaryl($C_1$-$C_3$)alkyl" means a functional group wherein a one to three carbon alkylene chain is attached to an optionally substituted heteroaryl group, e.g., —CH$_2$CH$_2$-pyridyl.

The term "heterocycle" or "heterocyclyl" or "heterocyclic" by itself or as part of another substituent means, unless otherwise stated, an unsubstituted or substituted, stable, non-aromatic mono- or multi-cyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to an unsubstituted or substituted, stable, mono- or multi-cyclic ring system having aromatic character which consists of carbon atoms and at least one heteroatom selected from the group consisting of N, O, and S, and wherein the nitrogen and sulfur heteroatoms may be optionally oxidized, and the nitrogen atom may be optionally quaternized. The heteroaryl or heteroaromatic system may be attached, unless otherwise stated, at any heteroatom or carbon atom which affords a stable structure.

A polycyclic heteroaryl may include one or more rings which are partially saturated. Examples include tetrahydroquinoline and 2,3-dihydrobenzofuryl.

Examples of heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: pyridyl, pyrazinyl, pyrimidinyl, particularly 2- and 4-pyrimidinyl, pyridazinyl, thienyl, furyl (furanyl), pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heteroaryls include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarinyl, dihydrocoumarinyl, benzofuryl, 1,5-naphthyridinyl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

For compounds of the present invention, when an aromatic or heteroaromatic ring is attached to a position and the ring comprises a polycyclic ring which is partially saturated, the attachment point on the aromatic or heteroaromatic ring is on a ring atom of an aromatic ring component of the polycyclic ring. For example on the partially saturated heteroaromatic ring, 1,2,3,4-tetrahydroisoquinoline, attachment points would be ring atoms at the 5-, 6-, 7- and 8-positions.

The phrase "optionally substituted" means that an atom or group of atoms has optionally replaced hydrogen as the substituent attached to another group. For aryl and heteroaryl groups, the term "optionally substituted" refers to any level of optional substitution, namely mono-, di-, tri-, tetra-, or penta-substitution, where such substitution(s) are permitted. When present, the substituents are independently selected, and each optional substitution may be at any chemically accessible position.

The term "antibody" is intended to encompass not only intact antigen-binding immunoglobulin molecules, but also to include antigen-binding fragments thereof such as Fab, Fab' and F(ab')$_2$ fragments, or any other fragment retaining the antigen-binding ability of an intact antibody.

The term "monospecific polyclonal antibody" means an antibody preparation comprising multiple antibody species having specificity for a single antigen.

The term "peptidyl group" refers to a peptide functional group. Such a functional group has a chemical structure that varies from the structure of the corresponding peptide in that the structural component of the peptide, i.e., an alpha amino group, a side chain amino group, an alpha carboxyl group or a side chain carboxyl group, will form a different functionality when bonded to the molecule of which it is to be a substituent. For example, for a peptide as shown below:

H$_2$N-Val-Pro-Ala-C(C=O)OH which is a substituent on a compound of Formula I, the peptide is coupled to the compound of Formula I such that a carboxyl moiety of said peptide is coupled to a free amine moiety on the Formula I compound. Elimination of water results in the formation of an amide bond. As a practical result, the corresponding monovalent peptidyl substituent is shown to the left of the dotted line in the depiction below of the aforementioned peptide bonded to a compound of Formula I:

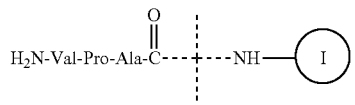

The monovalent peptide group may be attached via either an alpha- or a side chain amino group, or an alpha or side chain carboxyl group. The attachment point on the peptide group will depend on the functionality at the terminus of the group by which the peptide group is connected to the compound of Formula I or an antibody.

Specifically, the peptidyl group may be coupled to a connecting group via an alpha amino or a side chain amino group when a connecting group terminates in, for example:
—C(=O)—, —C(=S)—, —S(=O)—, or SO$_2$.

Likewise, the peptidyl group may be coupled to a connecting group via an alpha carboxy or a side chain carboxy group when the connecting group terminates in:
—C(=O)NR$^5$—, —SO$_2$NR$^5$—, —NR$^5$—, —S— or —O—.

II. Compounds of the Invention

In one aspect, the invention is a compound of Formula I, or a salt thereof:

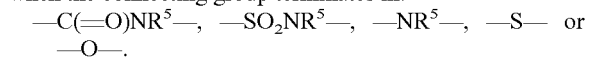

Formula I

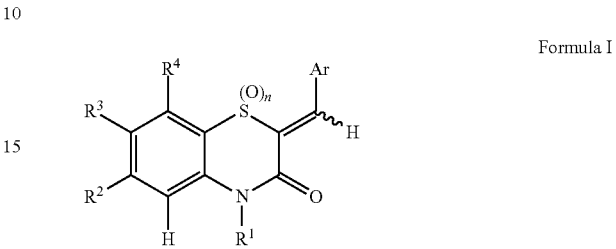

wherein n is 0, 1, or 2;

R$^1$ is selected from the group consisting of —H, —(C$_1$-C$_6$)alkyl, —(C$_2$-C$_6$)alkenyl, —(C$_2$-C$_6$)alkynyl, optionally substituted aryl, optionally substituted heteroaryl, optionally substituted aryl-(C$_1$-C$_6$)alkyl, optionally substituted heteroaryl-(C$_1$-C$_6$)alkyl, —C(=O)(C$_1$-C$_6$)alkyl, —C(=O)(C$_2$-C$_6$)alkenyl, —C(=O)-optionally substituted aryl, —C(=O)(CH$_2$)$_m$-optionally substituted aryl, and —C(=O)(CH$_2$)$_p$-optionally substituted heteroaryl;

R$^2$, R$^3$, and R$^4$ are independently selected from the group consisting of —H, halogen, —CN, —NR$^{10}$R$^{11}$, —OH, —OR$^{13}$, —(C$_1$-C$_6$)alkoxy, —NO$_2$, —(C$_1$-C$_6$)alkyl, —(C$_1$-C$_6$)perfluoroalkyl, —(C$_1$-C$_6$)perfluoroalkoxy, —C(=O)R$^{15}$, —C(=O)OR$^{15}$, —OC(=O)R$^{12}$, —OC(=O)OR$^{12}$, —C(=O)NR$^{17}$R$^{18}$, —SH, —S(C$_1$-C$_6$)alkyl, —SR$^{13}$, —S(=O)R$^{13}$, —S(=O)$_2$R$^{13}$, —OS(=O)$_2$R$^{13}$, —S(=O)$_q$R$^{15}$, —OS(=O)$_q$R$^{15}$, —S(=O)$_2$NR$^{17}$R$^{18}$, —S(=O)NR$^{17}$R$^{18}$, optionally substituted aryl, optionally substituted aryl-(C$_1$-C$_6$)alkyl, optionally substituted heteroaryl, optionally substituted heteroaryl-(C$_1$-C$_6$)alkyl, optionally substituted (C$_2$-C$_9$)heterocyclyl, optionally substituted (C$_2$-C$_9$)heterocyclyl-(C$_1$-C$_6$)alkyl, —NH(CH$_2$)$_m$C(=O)OR$^{14}$, —C(=NR$^{14}$)NR$^{14}$$_2$, —C(=N—OR$^{14}$)NR$^{14}$$_2$, —P(=O)(OR$^{14}$)$_2$, and —OP(=O)(OR$^{14}$)$_2$;

Ar is optionally substituted heteroaryl, optionally substituted (C$_{10}$-C$_{14}$)aryl, or

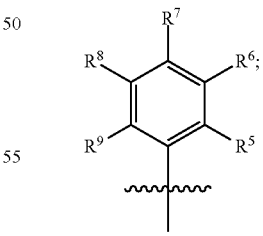

R$^5$, R$^6$, R$^7$, R$^8$, and R$^9$ are independently selected from the group consisting of —H, —OH, —OR$^{13}$, —NO$_2$, halogen, —CN, —NR$^{10}$R$^{11}$, —(CH$_2$)$_m$NR$^{10}$R$^{11}$, —O(CH$_2$)$_m$NR$^{10}$R$^{11}$, —(C$_1$-C$_6$)alkyl, —(CH$_2$)$_m$O(C$_1$-C$_6$)alkyl, —(C$_1$-C$_6$)alkoxy, —(C$_1$-C$_6$)perfluoroalkyl, —(C$_1$-C$_6$)perfluoroalkoxy, —SH, —S(C$_1$-C$_6$)alkyl, —SR$^{13}$, —S(=O)R$^{15}$, —S(=O)$_2$R$^{15}$, —C(=O)R$^{15}$, —C(=O)OR$^{15}$, —C(=O)NR$^{17}$R$^{18}$, —OC(=O)R$^{16}$, —OC(=O)OR$^{12}$, —OC(=O)

NR$^{17}$R$^{18}$, heterocyclyl, optionally substituted heteroaryl, —NH(CH$_2$)$_m$C(=O)OR$^{14}$, —OS(=O)$_2$R$^{16}$, —C(=NR$^{14}$)NR$^{14}_2$, —C(=N—OR$^{14}$)NR$^{14}_2$, —P(=O)(OR$^{14}$)$_2$, and —OP(=O)(OR$^{14}$)$_2$;

each R$^{10}$ and R$^{11}$ is independently selected from the group consisting of —H, —(C$_1$-C$_6$)alkyl, —(C$_1$-C$_6$)alkoxy, —C(=O)R$^{12}$, —C(C=O)NR$^{17}$R$^{18}$, —C(=O)OR$^{12}$, —C(=NR$^{14}$)NR$^{17}$R$^{18}$, R$^{13}$, optionally substituted aryl, optionally substituted heteroaryl, and —C(=NR$^{14}$)R$^{15}$; or R$^{10}$ and R$^{11}$, together with the nitrogen to which they are bound, form an optionally substituted (C$_2$-C$_5$)heterocycle;

each R$^{12}$ is independently selected from the group consisting of —(C$_1$-C$_6$)alkyl, and optionally substituted aryl;

each R$^{13}$ is independently selected from the group consisting of optionally substituted aryl and —(CH$_2$)$_m$R$^{16}$;

each R$^{14}$ is independently selected from the group consisting of —H and —(C$_1$-C$_6$)alkyl; or two occurrences of R$^{14}$ bound to the same nitrogen form a (C$_2$-C$_6$)heterocycle, together with the nitrogen atom to which they are bound;

each R$^{15}$ is independently selected from the group consisting of —H, —(C$_1$-C$_6$)alkyl, optionally substituted aryl, and NR$^{14}_2$;

each R$^{16}$ is independently selected from the group consisting of —(C$_1$-C$_6$)alkyl, —NR$^{14}_2$, and Ar$^1$;

each R$^{17}$ and R$^{18}$ is independently selected from the group consisting of —H, —(C$_1$-C$_6$)alkyl, —(C$_1$-C$_6$)alkoxy, R$^{13}$, optionally substituted aryl, and optionally substituted heteroaryl; or R$^{17}$ and R$^{18}$, together with the nitrogen to which they are bound, form an optionally substituted (C$_2$-C$_5$)heterocycle;

m is independently at each occurrence 1, 2, 3, 4, or 5;
p is independently at each occurrence 0, 1, 2, or 3;
q is independently at each occurrence 0, 1, or 2;

each optionally substituted aryl, optionally substituted (C$_{10}$-C$_{14}$)aryl, optionally substituted heteroaryl, optionally substituted aryl-(C$_1$-C$_6$)alkyl, optionally substituted heteroaryl-(C$_1$-C$_6$)alkyl, optionally substituted (C$_2$-C$_9$)heterocyclyl, optionally substituted (C$_2$-C$_9$)heterocyclyl-(C$_1$-C$_6$)alkyl, and optionally substituted (C$_2$-C$_5$)heterocycle is optionally substituted with one or more substituents independently selected from the group consisting of halogen, —CN, —NR$^{14}_2$, —(CH$_2$)$_m$NR$^{14}_2$, —O(CH$_2$)$_m$NR$^{14}_2$, —NR$^{14}$C(=O)(C$_1$-C$_6$)alkyl, —NR$^{14}$C(=O)O(C$_1$-C$_6$)alkyl, —NR$^{14}$C(=O)NR$^{14}_2$, —NR$^{14}$C(=NR$^{14}$)NR$^{14}_2$, —NH(CH$_2$)$_m$C(=O)OR$^{14}$, —OH, —NO$_2$, —(C$_1$-C$_6$)alkyl, —(CH$_2$)$_m$O(C$_1$-C$_6$)alkyl, —(C$_1$-C$_6$)alkoxy, —(C$_2$-C$_6$)alkenyl, —(C$_2$-C$_6$)alkynyl, —SR$^{14}$, —S(=O)R$^{15}$, —S(=O)$_2$R$^{15}$, —NR$^{14}$S(=O)$_2$R$^{15}$, —(C$_1$-C$_6$)perfluoroalkyl, —(C$_1$-C$_6$)perfluoroalkoxy, —C(=O)R$^{14}$, —C(=O)OR$^{14}$, —C(=O)NR$^{14}_2$, —OC(=O)R$^{14}$, —OC(=O)NR$^{14}_2$, —OC(=O)O(C$_1$-C$_6$)alkyl, —P(=O)(OR$^{14}$)$_2$, —OP(=O)(OR$^{14}$)$_2$, heterocyclyl, and heteroaryl;

Ar$^1$ is a radical according to Formula II

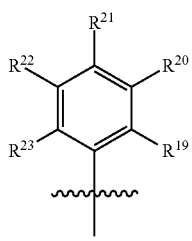

Formula II wherein R$^{19}$, R$^{20}$, R$^{21}$, R$^{22}$, and R$^{23}$ are independently selected from the group consisting of —H, —OH, —NO$_2$, halogen, —CN, —NR$^{10}$R$^{11}$, —(CH$_2$)$_m$NR$^{10}$R$^{11}$, —O(CH$_2$)$_m$NR$^{10}$R$^{11}$, —(C$_1$-C$_6$)alkyl, —(CH$_2$)$_m$O(C$_1$-C$_6$)alkyl, —(C$_1$-C$_6$)alkoxy, —(C$_1$-C$_6$)perfluoroalkyl, —(C$_1$-C$_6$)perfluoroalkoxy, —SH, —SR$^{12}$, —S(=O)R$^{15}$, —S(=O)$_2$R$^{15}$, —C(=O)R$^{15}$, —C(=O)OR$^{15}$, —C(=O)NR$^{17}$R$^{18}$, —OC(=O)R$^{16}$, —OC(=O)OR$^{12}$, —OC(=O)NR$^{17}$R$^{18}$, heterocyclyl, optionally substituted heteroaryl, —NH(CH$_2$)$_m$C(=O)OR$^{14}$, —OS(=O)$_2$R$^{16}$, —C(=NR$^{14}$)NR$^{14}_2$, —C(=N—OR$^{14}$)NR$^{14}_2$, —P(=O)(OR$^{14}$)$_2$, and —OP(=O)(OR$^{14}$)$_2$;

provided that:

i) at least one of R$^2$, R$^3$, or R$^4$ is other than hydrogen;

ii) when none of R$^2$, R$^3$, and R$^4$ are —OR$^{13}$, —NHR$^{13}$, —SR$^{13}$, —S(=O)R$^{13}$, or —S(=O)$_2$R$^{13}$, and Ar is

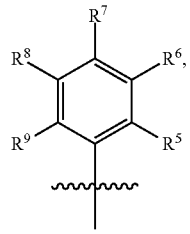

then at least one of R$^6$ and R$^8$ is —NO$_2$ and at least R$^7$ is other than hydrogen or halogen; and iii) when Ar is optionally substituted heteroaryl and none of R$^2$, R$^3$, or R$^4$ are —OR$^{13}$, —NHR$^{13}$, —SR$^{13}$, —S(=O)R$^{13}$, or —S(=O)$_2$R$^{13}$, then R$^1$ is other than hydrogen.

In preferred embodiments of a compound of Formula I, n is 0. In other embodiments, however, n is 1 or 2.

The wavy bond in the structure of Formula I indicates either (E), (Z), or a mixture of configurations of the double bond to the carbon atom to which Ar and ⌇H are attached.

In certain embodiments of the invention, the double bond in the compounds of Formula I can be in the E configuration. In preferred embodiments, the double bond is in the Z configuration:

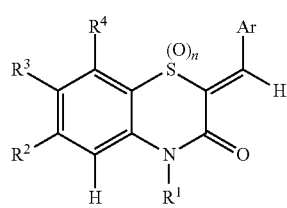

In certain instances, the double bond in the compound of Formula I is in the Z configuration, n is 0, and Ar is optionally substituted heteroaryl or

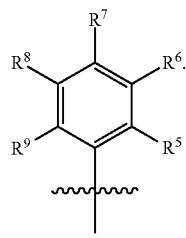

In certain embodiments, the optionally substituted heteroaryl group can be thiophene-2-yl (thiene-2-yl), thiophene-3-yl (thiene-3-yl), indol-2-yl, indol-3-yl, indol-4-yl, indol-5-yl, indol-6-yl, indol-7-yl, pyrrol-2-yl, pyrrol-3-yl, pyrimidin-4-yl, pyrimidin-5-yl, or pyrimidin-6-yl, any of which can be optionally substituted. In certain embodiments, the thiophene-2-yl (thiene-2-yl), thiophene-3-yl (thiene-3-yl), indol-2-yl, indol-3-yl, indol-4-yl, indol-5-yl, indol-6-yl, indol-7-yl, pyrrol-2-yl, pyrrol-3-yl, pyrimidin-4-yl, pyrimi din-5-yl, and pyrimidin-6-yl radicals can be optionally substituted with a halogen, an alkyl group, such as methyl or ethyl, or an acyl group such as an acetyl group. In particular embodiments, the acetyl group can be present on the nitrogen of any of the pyrrolyl or indolyl radicals. In other instances, the pyrimidinyl radicals can be substituted with a thioether, such as —SCH$_3$, or a morpholino group at any of the substitutable position, and in particular embodiments, at the 2 position of the pyriminidyl radical.

In certain embodiments of the invention, any of $R^2$, $R^3$, or $R^4$ can be —S(=O)$_2$R$^{13}$ wherein R$^{13}$ is —(CH$_2$)$_m$R$^{16}$, m is 1, and R$^{16}$ is

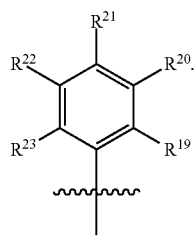

In particular embodiments, $R^2$ is —S(=O)$_2$R$^{13}$ wherein R$^{13}$ is —(CH$_2$)$_m$R$^{16}$, m is 1, and R$^{16}$ is

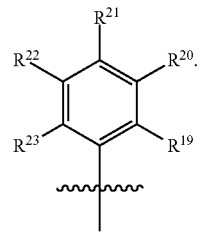

In certain embodiments, at least two of $R^{19}$, $R^{20}$, $R^{21}$, $R^{22}$, and $R^{23}$ are halogen atoms and can be the same or different halogen atoms. In particular embodiments, $R^{19}$ and $R^{23}$ are both halogen atoms (either the same or different), while $R^{20}$, $R^{21}$, and $R^{22}$ are other than halogen. In a further embodiment, $R^{19}$ and $R^{23}$ are the same halogen atom, while $R^{20}$, $R^{21}$, and $R^{22}$ are other than halogen. In certain embodiments, $R^{19}$ and $R^{23}$ are both chlorine atoms and $R^{20}$, $R^{21}$, and $R^{22}$ are each hydrogen.

Particular examples of compounds according to the invention, and salts thereof, are set forth in Table 1:

TABLE 1

| Cpd. # | Name | Structure |
|---|---|---|
| 1 | (Z)-4-((6-chloro-3-oxo-3,4-dihydro-2H-benzo[b][1,4]thiazin-2-ylidene)methyl)-2-nitrophenyl acetate | 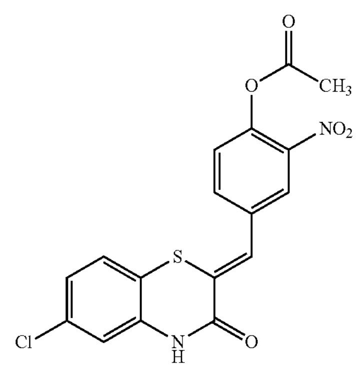 [SMILES: CC(=O)Oc1ccc(/C=C2\Sc3ccc(Cl)cc3NC2=O)cc1[N+](=O)[O-]] |
| 2 | (Z)-4-((7-methoxy-3-oxo-3,4-dihydro-2H-benzo[b][1,4]thiazin-2-ylidene)methyl)-2-nitrophenyl acetate | 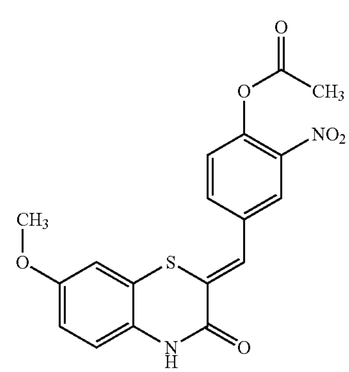 [SMILES: COc1ccc2c(c1)S/C(=C\c1ccc(OC(C)=O)c([N+](=O)[O-])c1)C(=O)N2] |

TABLE 1-continued

| Cpd. # | Name | Structure |
|---|---|---|
| 3 | (Z)-4-((7-bromo-3-oxo-3,4-dihydro-2H-benzo[b][1,4]thiazin-2-ylidene)methyl)-2-nitrophenyl acetate | 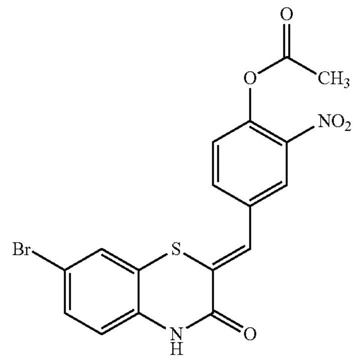 [SMILES: CC(=O)Oc1ccc(/C=C2\Sc3cc(Br)ccc3NC2=O)cc1[N+](=O)[O-]] |
| 4 | (Z)-4-((7-methyl-3-oxo-3,4-dihydro-2H-benzo[b][1,4]thiazin-2-ylidene)methyl)-2-nitrophenyl acetate | 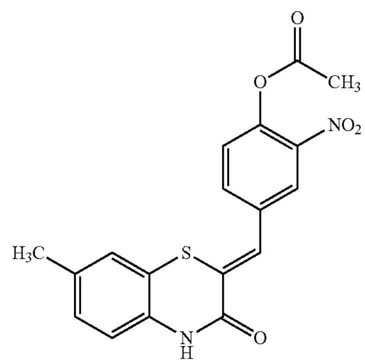 [SMILES: CC(=O)Oc1ccc(/C=C2\Sc3cc(C)ccc3NC2=O)cc1[N+](=O)[O-]] |
| 5 | (Z)-2-(4-acetoxy-3-nitrobenzylidene)-3-oxo-3,4-dihydro-2H-benzo[b][1,4]thiazine-7-carboxylic acid | 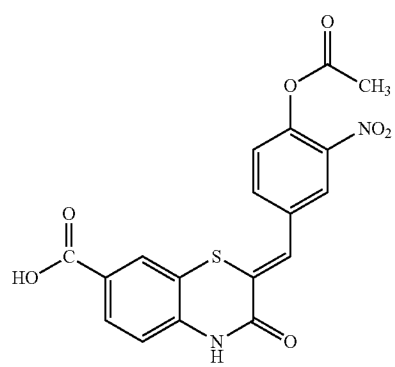 [SMILES: CC(=O)Oc1ccc(/C=C2\Sc3cc(C(=O)O)ccc3NC2=O)cc1[N+](=O)[O-]] |
| 6 | (Z)-4-((7-fluoro-3-oxo-3,4-dihydro-2H-benzo[b][1,4]thiazin-2-ylidene)methyl)-2-nitrophenyl acetate | 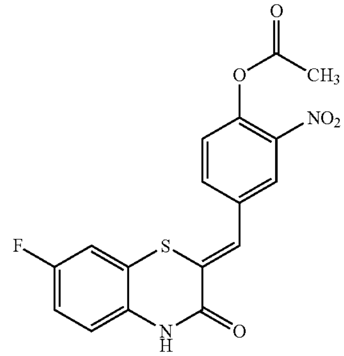 [SMILES: CC(=O)Oc1ccc(/C=C2\Sc3cc(F)ccc3NC2=O)cc1[N+](=O)[O-]] |

TABLE 1-continued

| Cpd. # | Name | Structure |
|---|---|---|
| 7 | (Z)-4-((6-fluoro-3-oxo-3,4-dihydro-2H-benzo[b][1,4]thiazin-2-ylidene)methyl)-2-nitrophenyl acetate | 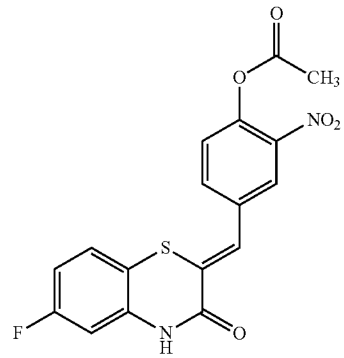 [SMILES: CC(=O)Oc1ccc(/C=C2\Sc3ccc(F)cc3NC2=O)cc1[N+](=O)[O-]] |
| 8 | (Z)-4-((6-((2,6-dichlorobenzyl)sulfonyl)-3-oxo-3,4-dihydro-2H-benzo[b][1,4]thiazin-2-ylidene)methyl)-2-nitrophenyl acetate | 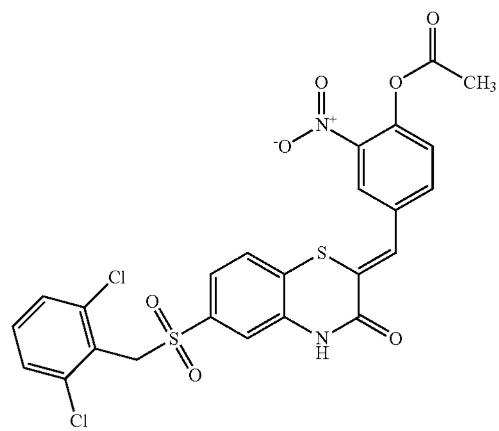 |
| 9 | (Z)-4-((6-((2,6-dichlorobenzyl)sulfonyl)-3-oxo-3,4-dihydro-2H-benzo[b][1,4]thiazin-2-ylidene)methyl)phenyl acetate | 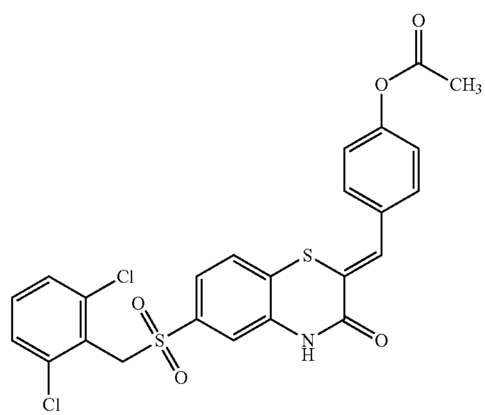 [SMILES: CC(=O)Oc1ccc(/C=C2\Sc3ccc(S(=O)(=O)Cc4c(Cl)cccc4Cl)cc3NC2=O)cc1] |
| 10 | (Z)-2-benzylidene-6-((2,6-dichlorobenzyl)sulfonyl)-2H-benzo[b][1,4]thiazin-3(4H)-one | 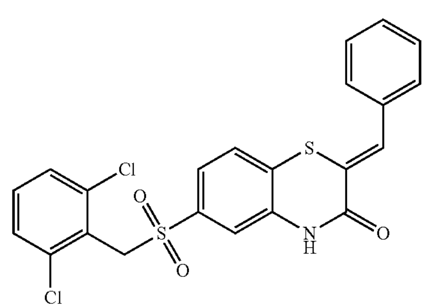 [SMILES: O=C1Nc2cc(S(=O)(=O)Cc3c(Cl)cccc3Cl)ccc2S/C1=C\c1ccccc1] |

TABLE 1-continued

| Cpd. # | Name | Structure |
|---|---|---|
| 11 | (Z)-6-((2,6-dichlorobenzyl)sulfonyl)-2-(4-methoxy-3-nitrobenzylidene)-2H-benzo[b][1,4]thiazin-3(4H)-one | 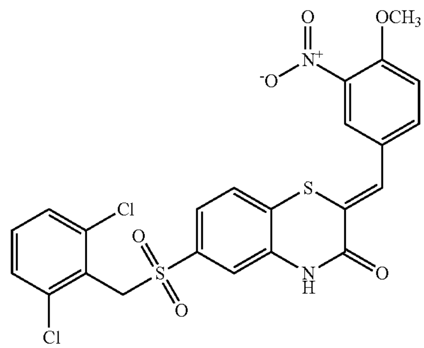 |
| 12 | (Z)-2-(3-amino-4-methoxybenzylidene)-6-((2,6-dichlorobenzyl)sulfonyl)-2H-benzo[b][1,4]thiazin-3(4H)-one | 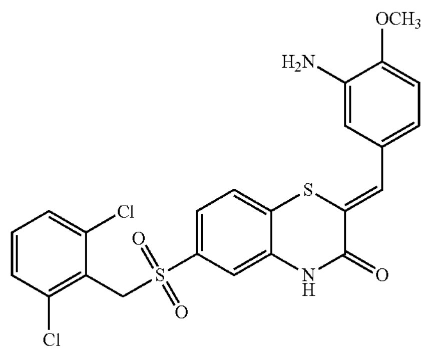 [SMILES: COc1ccc(/C=C2\Sc3ccc(S(=O)(=O)Cc4c(Cl)cccc4Cl)cc3NC2=O)cc1N] |
| 13 | (Z)-6-((2,6-dichlorobenzyl)sulfonyl)-2-(4-(4-methylpiperazin-1-yl)benzylidene)-2H-benzo[b][1,4]thiazin-3(4H)-one | 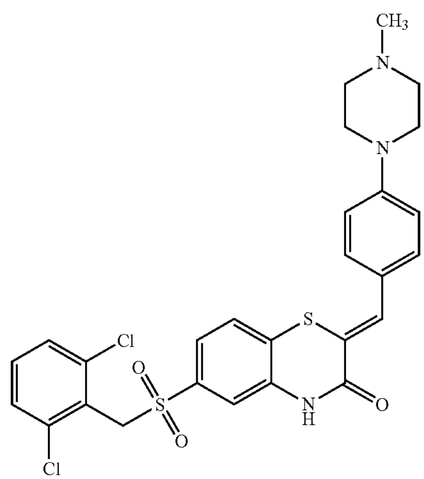 [SMILES: CN1CCN(c2ccc(/C=C3\Sc4ccc(S(=O)(=O)Cc5c(Cl)cccc5Cl)cc4NC3=O)cc2)CC1] |
| 14 | (Z)-6-((2,6-dichlorobenzyl)sulfonyl)-2-(4-nitrobenzylidene)-2H-benzo[b][1,4]thiazin-3(4H)-one | 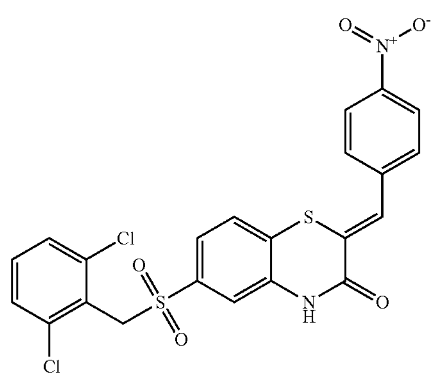 [SMILES: O=C1Nc2cc(S(=O)(=O)Cc3c(Cl)cccc3Cl)ccc2S/C1=C\c1ccc([N+](=O)[O-])cc1] |

TABLE 1-continued

| Cpd. # | Name | Structure |
|---|---|---|
| 15 | (Z)-2-(4-aminobenzylidene)-6-((2,6-dichlorobenzyl)sulfonyl)-2H-benzo[b][1,4]thiazin-3(4H)-one | 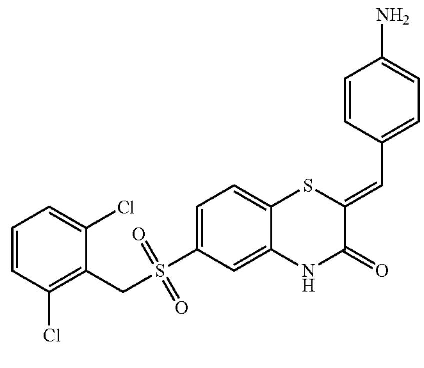 [SMILES: Nc1ccc(/C=C2\Sc3ccc(S(=O)(=O)Cc4c(Cl)cccc4Cl)cc3NC2=O)cc1] |
| 16 | (Z)-6-((2,6-dichlorobenzyl)sulfonyl)-2-(4-fluorobenzylidene)-2H-benzo[b][1,4]thiazin-3(4H)-one | 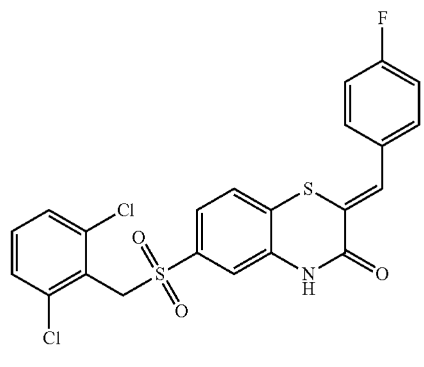 |
| 17 | (Z)-2-(4-chlorobenzylidene)-6-((2,6-dichlorobenzyl)sulfonyl)-2H-benzo[b][1,4]thiazin-3(4H)-one | 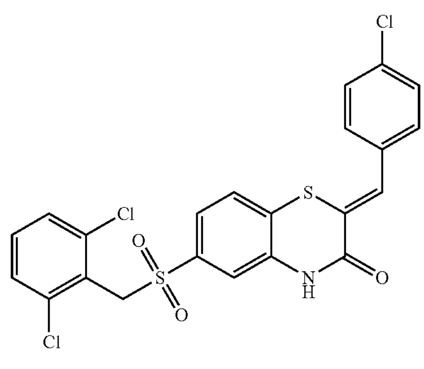 [SMILES: O=C1Nc2cc(S(=O)(=O)Cc3c(Cl)cccc3Cl)ccc2S/C1=C\c1ccc(Cl)cc1] |
| 18 | (Z)-2-(4-bromobenzylidene)-6-((2,6-dichlorobenzyl)sulfonyl)-2H-benzo[b][1,4]thiazin-3(4H)-one | 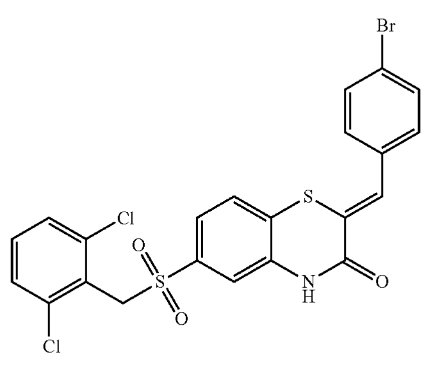 [SMILES: O=C1Nc2cc(S(=O)(=O)Cc3c(Cl)cccc3Cl)ccc2S/C1=C\c1ccc(Br)cc1] |

TABLE 1-continued

| Cpd. # | Name | Structure |
|---|---|---|
| 19 | (Z)-6-((2,6-dichlorobenzyl)sulfonyl)-2-(4-methoxybenzylidene)-2H-benzo[b][1,4]thiazin-3(4H)-one | 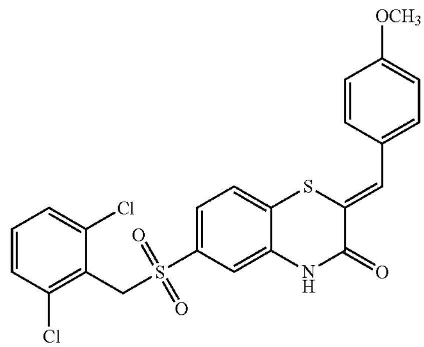 [SMILES: COc1ccc(/C=C2\Sc3ccc(S(=O)(=O)Cc4c(Cl)cccc4Cl)cc3NC2=O)cc1] |
| 20 | (Z)-6-((2,6-dichlorobenzyl)sulfonyl)-2-(4-methylbenzylidene)-2H-benzo[b][1,4]thiazin-3(4H)-one | 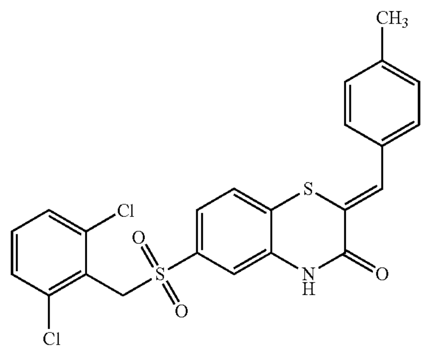 [SMILES: Cc1ccc(/C=C2\Sc3ccc(S(=O)(=O)Cc4c(Cl)cccc4Cl)cc3NC2=O)cc1] |
| 21 | (Z)-6-((2,6-dichlorobenzyl)sulfonyl)-2-(2,4,6-trimethoxybenzylidene)-2H-benzo[b][1,4]thiazin-3(4H)-one | 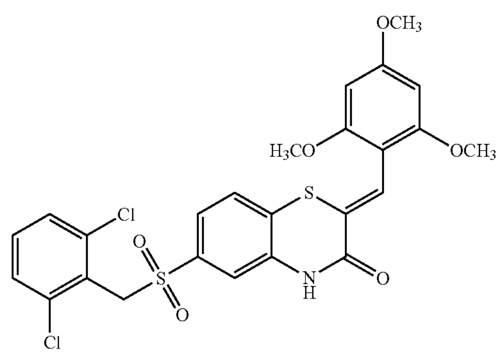 [SMILES: COc1cc(OC)c(/C=C2\Sc3ccc(S(=O)(=O)Cc4c(Cl)cccc4Cl)cc3NC2=O)c(OC)c1] |
| 22 | (Z)-6-((2,6-dichlorobenzyl)sulfonyl)-2-(2,4-dichlorobenzylidene)-2H-benzo[b][1,4]thiazin-3(4H)-one | 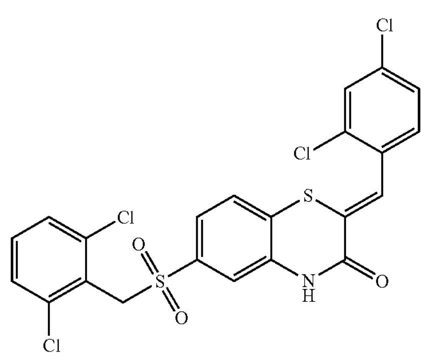 [SMILES: O=C1Nc2cc(S(=O)(=O)Cc3c(Cl)cccc3Cl)ccc2S/C1=C\c1ccc(Cl)cc1Cl] |
| 23 | (number intentionally skipped) | — |

TABLE 1-continued

| Cpd. # | Name | Structure |
|---|---|---|
| 24 | (Z)-methyl 2-((4-((6-((2,6-dichlorobenzyl)sulfonyl)-3-oxo-3,4-dihydro-2H-benzo[b][1,4]thiazin-2-ylidene)methyl)phenyl)amino)acetate | 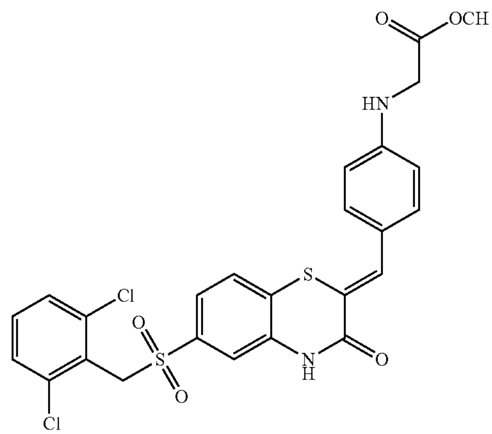 |
| 25 | (Z)-2-((4-((6-((2,6-dichlorobenzyl)sulfonyl)-3-oxo-3,4-dihydro-2H-benzo[b][1,4]thiazin-2-ylidene)methyl)phenyl)amino)acetic acid | 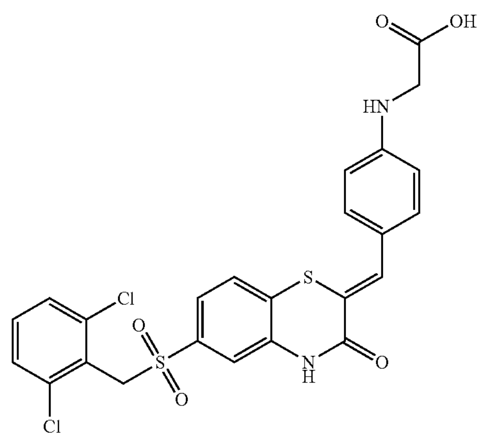 [SMILES: O=C(O)CNc1ccc(/C=C2\Sc3ccc(S(=O)(=O)Cc4c(Cl)cccc4Cl)cc3NC2=O)cc1] |
| 26 | (Z)-2-((1-acetyl-1H-indol-3-yl)methylene)-6-((2,6-dichlorobenzyl)sulfonyl)-2H-benzo[b][1,4]thiazin-3(4H)-one | 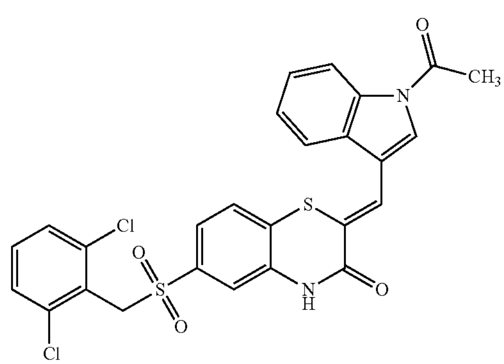 [SMILES: CC(=O)n1cc(/C=C2\Sc3ccc(S(=O)(=O)Cc4c(Cl)cccc4Cl)cc3NC2=O)c2ccccc21] |
| 27 | (Z)-2-((1H-pyrrol-3-yl)methylene)-6-((2,6-dichlorobenzyl)sulfonyl)-2H-benzo[b][1,4]thiazin-3(4H)-one | 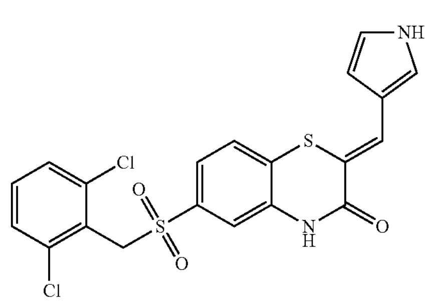 [SMILES: O=C1Nc2cc(S(=O)(=O)Cc3c(Cl)cccc3Cl)ccc2S/C1=C\c1cc[nH]c1] |

TABLE 1-continued

| Cpd. # | Name | Structure |
|---|---|---|
| 28 | (Z)-6-((2,6-dichlorobenzyl)sulfonyl)-2-(4-hydroxy-2,6-dimethoxybenzylidene)-2H-benzo[b][1,4]thiazin-3(4H)-one | 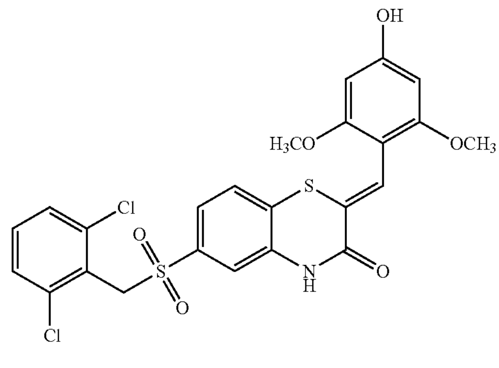 [SMILES: COc1cc(O)cc(OC)c1/C=C1\Sc2ccc(S(=O)(=O)Cc3c(Cl)cccc3Cl)cc2NC1=O] |
| 29 | (Z)-2-(4-chloro-3-nitrobenzylidene)-6-((2,6-dichlorobenzyl)sulfonyl)-2H-benzo[b][1,4]thiazin-3(4H)-one | 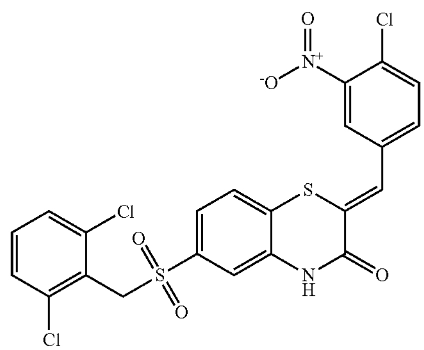 |
| 30 | (Z)-6-((2,6-dichlorobenzyl)sulfonyl)-2-(2,4-difluorobenzylidene)-2H-benzo[b][1,4]thiazin-3(4H)-one | 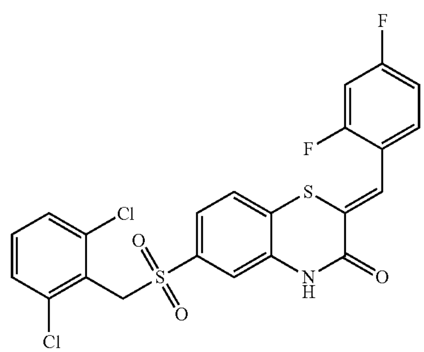 [SMILES: O=C1Nc2cc(S(=O)(=O)Cc3c(Cl)cccc3Cl)ccc2S/C1=C\c1ccc(F)cc1F] |
| 31 | (Z)-6-((2,6-dichlorobenzyl)sulfonyl)-2-(2,4,6-trifluorobenzylidene)-2H-benzo[b][1,4]thiazin-3(4H)-one | 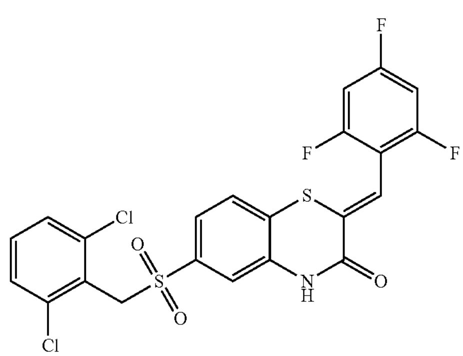 [SMILES: O=C1Nc2cc(S(=O)(=O)Cc3c(Cl)cccc3Cl)ccc2S/C1=C\c1c(F)cc(F)cc1F] |

TABLE 1-continued

| Cpd. # | Name | Structure |
|---|---|---|
| 32 | (Z)-methyl 4-((6-((2,6-dichlorobenzyl)sulfonyl)-3-oxo-3,4-dihydro-2H-benzo[b][1,4]thiazin-2-ylidene)methyl)benzoate | 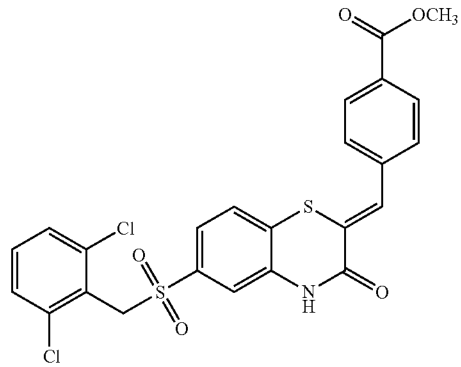 [SMILES: COC(=O)c1ccc(/C=C2\Sc3ccc(S(=O)(=O)Cc4c(Cl)cccc4Cl)cc3NC2=O)cc1] |
| 33 | (Z)-6-((2,6-dichlorobenzyl)sulfonyl)-2-(thiophen-2-ylmethylene)-2H-benzo[b][1,4]thiazin-3(4H)-one | 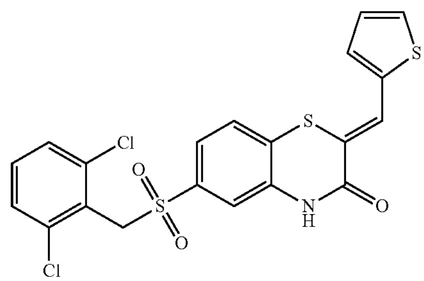 [SMILES: O=C1Nc2cc(S(=O)(=O)Cc3c(Cl)cccc3Cl)ccc2S/C1=C\c1cccs1] |
| 34 | (Z)-2-((1H-indol-3-yl)methylene)-6-((2,6-dichlorobenzyl)sulfonyl)-2H-benzo[b][1,4]thiazin-3(4H)-one | 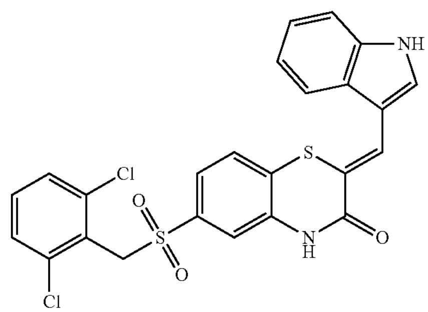 [SMILES: O=C1Nc2cc(S(=O)(=O)Cc3c(Cl)cccc3Cl)ccc2S/C1=C\c1c[nH]c2ccccc12] |
| 35 | (Z)-methyl 4-((6-((2,6-dichlorobenzyl)sulfonyl)-3-oxo-3,4-dihydro-2H-benzo[b][1,4]thiazin-2-ylidene)methyl)-3-nitrobenzoate | 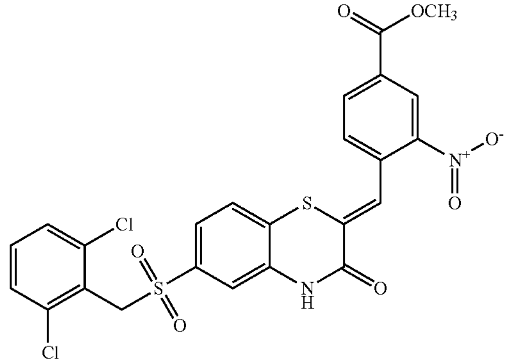 [SMILES: COC(=O)c1ccc(/C=C2\Sc3ccc(S(=O)(=O)Cc4c(Cl)cccc4Cl)cc3NC2=O)c([N+](=O)[O-])c1] |

TABLE 1-continued

| Cpd. # | Name | Structure |
|---|---|---|
| 36 | (Z)-6-((2,6-dichlorobenzyl)sulfonyl)-2-((2-(methylthio)pyrimidin-4-yl)methylene)-2H-benzo[b][1,4]thiazin-3(4H)-one | 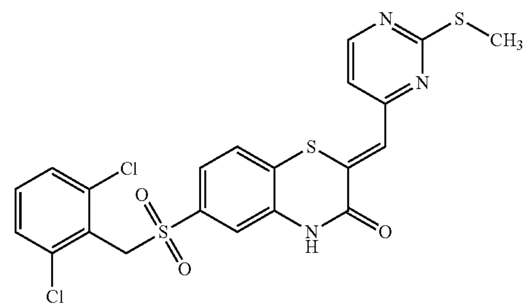 [SMILES: CSc1nccc(/C=C2\Sc3ccc(S(=O)(=O)Cc4c(Cl)cccc4Cl)cc3NC2=O)n1] |
| 37 | (Z)-6-((2,6-dichlorobenzyl)sulfonyl)-2-((2-morpholinopyrimidin-4-yl)methylene)-2H-benzo[b][1,4]thiazin-3(4H)-one | 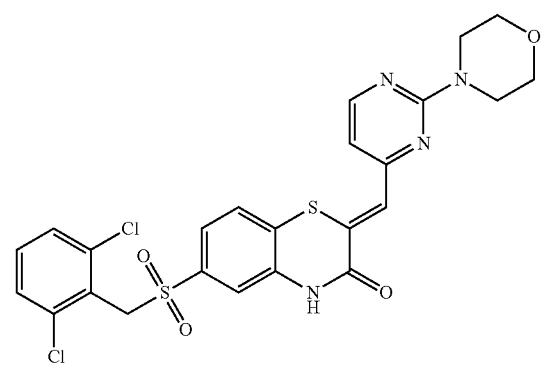 [SMILES: O=C1Nc2cc(S(=O)(=O)Cc3c(Cl)cccc3Cl)ccc2S/C1=C\c1ccnc(N2CCOCC2)n1] |
| 38 | (Z)-4-((6-((2,6-dichlorobenzyl)sulfonyl)-3-oxo-3,4-dihydro-2H-benzo[b][1,4]thiazin-2-ylidene)methyl)-2-nitrophenyl 4-methylbenzenesulfonate | 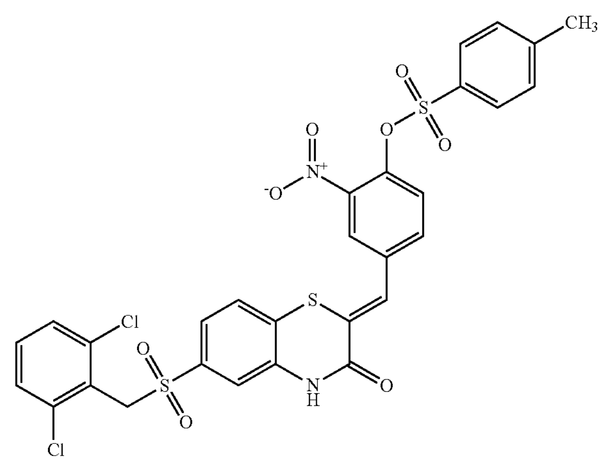 |
| 39 | (Z)-2-(4-(2H-tetrazol-5-yl)benzylidene)-6-((2,6-dichlorobenzyl)sulfonyl)-2H-benzo[b][1,4]thiazin-3(4H)-one | 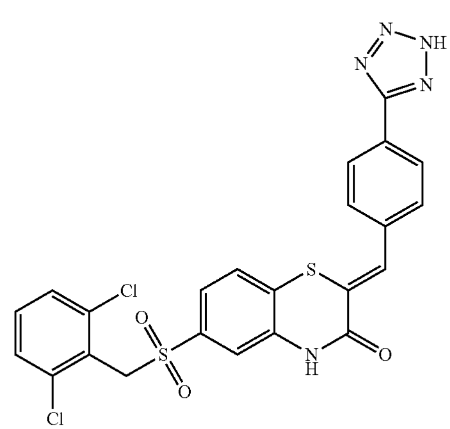 [SMILES: O=C1Nc2cc(S(=O)(=O)Cc3c(Cl)cccc3Cl)ccc2S/C1=C\c1ccc(-c2nn[nH]n2)cc1] |

TABLE 1-continued

| Cpd. # | Name | Structure |
|---|---|---|
| 40 | (Z)-4-((4-acetyl-7-methoxy-3-oxo-3,4-dihydro-2H-benzo[b][1,4]thiazin-2-ylidene)methyl)-2-nitrophenyl acetate | 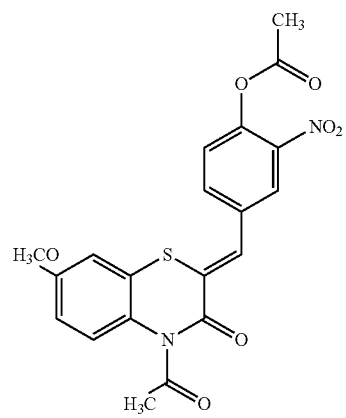 [SMILES: COc1ccc2c(c1)S/C(=C\c1ccc(OC(C)=O)c([N+](=O)[O-])c1)C(=O)N2C(C)=O] |
| 41 | (Z)-2-(4-(benzyloxy)-3-nitrobenzylidene)-6-((2,6-dichlorobenzyl)sulfonyl)-2H-benzo[b][1,4]thiazin-3(4H)-one | 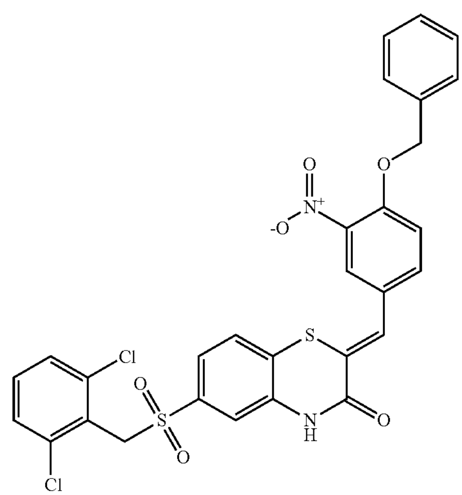 |
| 42 | (Z)-6-((2,6-dichlorobenzyl)sulfonyl)-2-(4-hydroxy-3-nitrobenzylidene)-2H-benzo[b][1,4]thiazin-3(4H)-one | 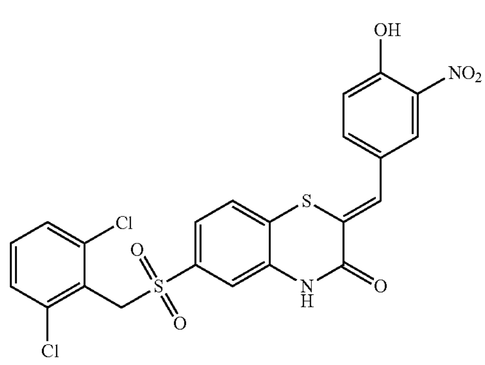 [SMILES: O=C1Nc2cc(S(=O)(=O)Cc3c(Cl)cccc3Cl)ccc2S/C1=C\c1ccc(O)c([N+](=O)[O-])c1] |

TABLE 1-continued

| Cpd. # | Name | Structure |
|---|---|---|
| 43 | (Z)-2-(4-(benzyloxy)-3-nitrobenzylidene)-7-fluoro-2H-benzo[b][1,4]thiazin-3(4H)-one | 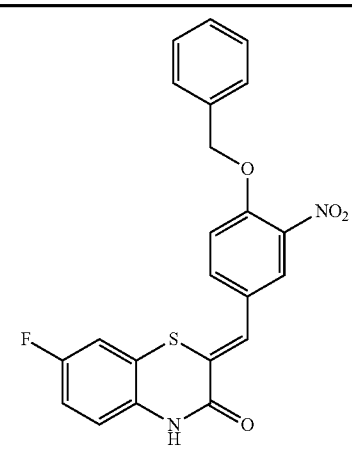 |
| 44 | (Z)-7-fluoro-2-(4-hydroxy-3-nitrobenzylidene)-2H-benzo[b][1,4]thiazin-3(4H)-one | 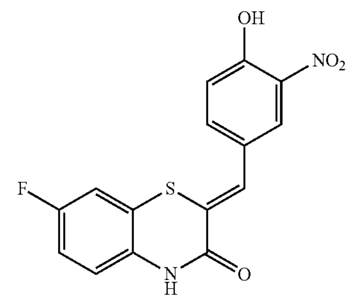 [SMILES: O=C1Nc2ccc(F)cc2S/C1=C\c1ccc(O)c([N+](=O)[O-])c1] |

Other exemplary compounds include, but are not limited to the following, and salts thereof: (Z)-4-((6-((2,6-dibromobenzyl)sulfonyl)-3-oxo-3,4-dihydro-2H-benzo[b][1,4]thiazin-2-ylidene)methyl)-2-nitrophenyl acetate; (Z)-4-((6-((2,6-dibromobenzyl)sulfonyl)-3-oxo-3,4-dihydro-2H-benzo[b][1,4]thiazin-2-ylidene)methyl)phenyl acetate; (Z)-2-benzylidene-6-((2,6-dibromobenzyl)sulfonyl)-2H-benzo[b][1,4]thiazin-3(4H)-one; (Z)-6-((2,6-dibromobenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-(4-methylpiperazin-1-yl)benzylidene)-2H-benzo[b][1,4]thiazin-3(4H)-one; (Z)-6-((2,6-dibromobenzyl)sulfonyl)-2-(4-nitrobenzylidene)-2H-benzo[b][1,4]thiazin-3(4H)-one; (Z)-2-(4-aminobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-fluorobenzylidene)-2H-benzo[b][1,4]thiazin-3(4H)-one; (Z)-2-(4-chlorobenzylidene)-6-((2,6-dibromobenzyl)sulfonyl)-2H-benzo[b][1,4]thiazin-3(4H)-one; (Z)-2-(4-bromobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-methoxybenzylidene)-2H-benzo[b][1,4]thiazin-3(4H)-one; (Z)-6-((2,6-dibromobenzyl)sulfonyl)-2-(4-methylbenzylidene)-2H-benzo[b][1,4]thiazin-3(4H)-one; (Z)-6-((2,6-dibromobenzyl)sulfonyl)-2-(2,4,6-trimethoxybenzylidene)-2H-benzo[b][1,4]thiazin-3(4H)-one; (Z)-6-((2,6-dibromobenzyl)sulfonyl)-2-(2,4-dibromobenzylidene)-2H-benzo[b][1,4]thiazin-3(4H)-one; (Z)-6-((2,6-dibromobenzyl)sulfonyl)-2-(2,4,6-trifluorobenzylidene)-2H-benzo[b][1,4]thiazin-3(4H)-one; (Z)-methyl 2-((4-((6-((2,6-dibromobenzyl)sulfonyl)-3-oxo-3,4-dihydro-2H-benzo[b][1,4]thiazin-2-ylidene)methyl)phenyl)amino)acetate; (Z)-2-((4-((6-((2,6-dibromobenzyl)sulfonyl)-3-oxo-3,4-dihydro-2H-benzo[b][1,4]thiazin-2-ylidene)methyl)phenyl)amino)acetic acid; (Z)-6-((2,6-dibromobenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(2,4-difluorobenzylidene)-2H-benzo[b][1,4]thiazin-3(4H)-one; (Z)-6-((2,6-dibromobenzyl)sulfonyl)-2-(2,4,6-trifluorobenzylidene)-2H-benzo[b][1,4]thiazin-3(4H)-one; (Z)-methyl 4-((6-((2,6-dibromobenzyl)sulfonyl)-3-oxo-3,4-dihydro-2H-benzo[b][1,4]thiazin-2-ylidene)methyl)benzoate; (Z)-methyl 4-((6-((2,6-dibromobenzyl)sulfonyl)-3-oxo-3,4-dihydro-2H-benzo[b][1,4]thiazin-2-ylidene)methyl)-3-nitrobenzoate; (Z)-4-((6-((2,6-dibromobenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dibromobenzyl)sulfonyl)-2H-benzo[b][1,4]thiazin-3(4H)-one; (Z)-2-(4-(benzyloxy)-3-nitrobenzylidene)-6-((2,6-dibromobenzyl)sulfonyl)-2H-benzo[b][1,4]thiazin-3(4H)-one; (Z)-6-((2,6-dibromobenzyl)sulfonyl)-2-(4-hydroxy-3-nitrobenzylidene)-2H-benzo[b][1,4]thiazin-3(4H)-one; (Z)-4-((6-((2,6-difluorobenzyl)sulfonyl)-3-oxo-3,4-dihydro-2H-benzo[b][1,4]thiazin-2-ylidene)methyl)-2-nitrophenyl acetate; (Z)-4-((6-((2,6-difluorobenzyl)sulfonyl)-3-oxo-3,4-dihydro-2H-benzo[b][1,4]thiazin-2-ylidene)methyl)phenyl acetate; (Z)-2-benzylidene-6-((2,6-difluorobenzyl)sulfonyl)-2H-benzo[b][1,4]thiazin-3(4H)-one; (Z)-6-((2,6-difluorobenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-(4-methylpiperazin-1-yl)benzylidene)-2H-benzo[b][1,4]thiazin-3(4H)-one; (Z)-6-((2,6-difluorobenzyl)sulfonyl)-2-(4-nitrobenzylidene)-2H-benzo[b][1,4]thiazin-3(4H)-one; (Z)-2-(4-aminobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-fluorobenzylidene)-2H-benzo[b][1,4]thiazin-3(4H)-one; (Z)-2-(4-chlorobenzylidene)-6-((2,6-difluorobenzyl)sulfonyl)-2H-benzo[b][1,4]thiazin-3(4H)-one; (Z)-2-(4-bromobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-methoxybenzylidene)-2H-benzo[b][1,4]thiazin-3(4H)-one; (Z)-6-((2,6-difluorobenzyl)sulfonyl)-2-(4-methylbenzylidene)-2H-benzo[b][1,4]thiazin-3(4H)-one; (Z)-6-((2,6-difluorobenzyl)sulfonyl)-2-(2,4,6-trimethoxybenzylidene)-2H-benzo[b][1,4]thiazin-3(4H)-one; (Z)-6-((2,6-difluorobenzyl)sulfonyl)-2-(2,4-difluorobenzylidene)-2H-benzo[b][1,4]thiazin-3(4H)-one; (Z)-6-((2,6-difluorobenzyl)sulfonyl)-2-(2,4,6-trifluorobenzylidene)-2H-benzo[b][1,4]thiazin-3(4H)-one; (Z)-methyl 2-((4-((6-((2,6-difluorobenzyl)sulfonyl)-3-oxo-3,4-dihydro-2H-benzo[b][1,4]thiazin-2-ylidene)methyl)phenyl)amino)acetate; (Z)-2-((4-((6-((2,6-difluorobenzyl)sulfonyl)-3-oxo-3,4-dihydro-2H-benzo[b][1,4]thiazin-2-ylidene)methyl)phenyl)amino)acetic acid; (Z)-6-((2,6-difluorobenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(2,4-difluorobenzylidene)-2H-benzo[b][1,4]thiazin-3(4H)-one; (Z)-6-((2,6-difluorobenzyl)sulfonyl)-2-(2,4,6-trifluorobenzylidene)-2H-benzo[b][1,4]thiazin-3(4H)-one; (Z)-methyl 4-((6-((2,6-difluorobenzyl)sulfonyl)-3-oxo-3,4-dihydro-2H-benzo[b][1,4]thiazin-2-ylidene)methyl)benzoate; (Z)-methyl 4-((6-((2,6-difluorobenzyl)sulfonyl)-3-oxo-3,4-dihydro-2H-benzo[b][1,4]thiazin-2-ylidene)methyl)-3-nitrobenzoate; (Z)-4-((6-((2,6-difluorobenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-difluorobenzyl)sulfonyl)-2H-benzo[b][1,4]thiazin-3(4H)-one; (Z)-2-(4-(benzyloxy)-3-nitrobenzylidene)-6-((2,6-difluorobenzyl)sulfonyl)-2H-benzo[b][1,4]thiazin-3(4H)-one; (Z)-6-((2,6-difluorobenzyl)sulfonyl)-2-(4-hydroxy-3-nitrobenzylidene)-2H-benzo[b][1,4]thiazin-3(4H)-one; (Z)-4-((6-((2,6-dimethylbenzyl)sulfonyl)-3-oxo-3,4-dihydro-2H-benzo[b][1,4]thiazin-2-ylidene)methyl)-2-nitrophenyl acetate; (Z)-4-((6-((2,6-dimethylbenzyl)sulfonyl)-3-oxo-3,4-dihydro-2H-benzo[b][1,4]thiazin-2-ylidene)methyl)phenyl acetate; (Z)-2-benzylidene-6-((2,6-dimethylbenzyl)sulfonyl)-2H-benzo[b][1,4]thiazin-3(4H)-one; (Z)-6-((2,6-dimethylbenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-(4-methylpiperazin-1-yl)benzylidene)-2H-benzo[b][1,4]thiazin-3(4H)-one; (Z)-6-((2,6-dimethylbenzyl)sulfonyl)-2-(4-nitrobenzylidene)-2H-benzo[b][1,4]thiazin-3(4H)-one; (Z)-2-(4-aminobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-fluorobenzylidene)-2H-benzo[b][1,4]thiazin-3(4H)-one; (Z)-2-(4-chlorobenzylidene)-6-((2,6-dimethylbenzyl)sulfonyl)-2H-benzo[b][1,4]thiazin-3(4H)-one; (Z)-2-(4-bromobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-methoxybenzylidene)-2H-benzo[b][1,4]thiazin-3(4H)-one; (Z)-6-((2,6-dimethylbenzyl)sulfonyl)-2-(4-methylbenzylidene)-2H-benzo[b][1,4]thiazin-3(4H)-one; (Z)-6-((2,6-dimethylbenzyl)sulfonyl)-2-(2,4,6-trimethoxybenzylidene)-2H-benzo[b][1,4]thiazin-3(4H)-one; (Z)-6-((2,6-dimethylbenzyl)sulfonyl)-2-(2,4-dimethylbenzylidene)-2H-benzo[b][1,4]thiazin-3(4H)-one; (Z)-6-((2,6-dimethylbenzyl)sulfonyl)-2-(2,4,6-trifluorobenzylidene)-2H-benzo[b][1,4]thiazin-3(4H)-one; (Z)-methyl 2-((4-((6-((2,6-dimethylbenzyl)sulfonyl)-3-oxo-3,4-dihydro-2H-benzo[b][1,4]thiazin-2-ylidene)methyl)phenyl)amino)acetate; (Z)-2-((4-((6-((2,6-dimethylbenzyl)sulfonyl)-3-oxo-3,4-dihydro-2H-benzo[b][1,4]thiazin-2-ylidene)methyl)phenyl)amino)acetic acid; (Z)-6-((2,6-dimethylbenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(2,4-difluorobenzylidene)-2H-benzo[b][1,4]thiazin-3(4H)-one; (Z)-6-((2,6-dimethylbenzyl)sulfonyl)-2-(2,4,6-trifluorobenzylidene)-2H-benzo[b][1,4]thiazin-3(4H)-one; (Z)-methyl 4-((6-((2,6-dimethylbenzyl)sulfonyl)-3-oxo-3,4-dihydro-2H-benzo[b][1,4]thiazin-2-ylidene)methyl)benzoate; (Z)-methyl 4-((6-((2,6-dimethylbenzyl)sulfonyl)-3-oxo-3,4-dihydro-2H-benzo[b][1,4]thiazin-2-ylidene)methyl)-3-nitrobenzoate; (Z)-4-((6-((2,6-dimethylbenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dimethylbenzyl)sulfonyl)-2H-benzo[b][1,4]thiazin-3(4H)-one; (Z)-2-(4-(benzyloxy)-3-nitrobenzylidene)-6-((2,6-dimethylbenzyl)sulfonyl)-2H-benzo[b][1,4]thiazin-3(4H)-one; and (Z)-6-((2,6-dimethylbenzyl)sulfonyl)-2-(4-hydroxy-3-nitrobenzylidene)-2H-benzo[b][1,4]thiazin-3(4H)-one; (Z)-4-((6-((2,6-dimethoxybenzyl)sulfonyl)-3-oxo-3,4-dihydro-2H-benzo[b][1,4]thiazin-2-ylidene)methyl)-2-nitrophenyl acetate; (Z)-4-((6-((2,6-dimethoxybenzyl)sulfonyl)-3-oxo-3,4-dihydro-2H-benzo[b][1,4]thiazin-2-ylidene)methyl)phenyl acetate; (Z)-2-benzylidene-6-((2,6-dimethoxybenzyl)sulfonyl)-2H-benzo[b][1,4]thiazin-3(4H)-one; (Z)-6-((2,6-dimethoxybenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-(4-methylpiperazin-1-yl)benzylidene)-2H-benzo[b][1,4]thiazin-3(4H)-one; (Z)-6-((2,6-dimethoxybenzyl)sulfonyl)-2-(4-nitrobenzylidene)-2H-benzo[b][1,4]thiazin-3(4H)-one; (Z)-2-(4-aminobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-fluorobenzylidene)-2H-benzo[b][1,4]thiazin-3(4H)-one; (Z)-2-(4-chlorobenzylidene)-6-((2,6-dimethoxybenzyl)sulfonyl)-2H-benzo[b][1,4]thiazin-3(4H)-one; (Z)-2-(4-bromobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-methoxybenzylidene)-2H- benzo[b][1,4]thiazin-3(4H)-one; (Z)-6-((2,6-dimethoxybenzyl)sulfonyl)-2-(4-methylbenzylidene)-2H-benzo[b][1,4]thiazin-3(4H)-one; (Z)-6-((2,6-dimethoxybenzyl) sulfonyl)-2-(2,4,6-trimethoxybenzylidene)-2H-benzo[b][1,4]thiazin-3 (4H)-one; (Z)-6-((2,6-dimethoxybenzyl)sulfonyl)-2-(2,4-dimethoxybenzylidene)-2H-benzo[b][1,4]thiazin-3(4H)-one; (Z)-6-((2,6-dimethoxybenzyl)sulfonyl)-2-(2,4,6-trifluorobenzylidene)-2H-benzo[b][1,4]thiazin-3(4H)-one; (Z)-methyl 2-((4-((6-((2,6-dimethoxybenzyl)sulfonyl)-3-oxo-3,4-dihydro-2H-benzo[b][1,4]thiazin-2-ylidene)methyl)phenyl)amino)acetate; (Z)-2-((4-((6-((2,6-dimethoxybenzyl)sulfonyl)-3-oxo-3,4-dihydro-2H-benzo[b][1,4]thiazin-2-ylidene)methyl)phenyl)amino)acetic acid; (Z)-6-((2,6-dimethoxybenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(2,4-di fluorobenzylidene)-2H-benzo[b][1,4]thiazin-3(4H)-one; (Z)-6-((2,6-dimethoxybenzyl)sulfonyl)-2-(2,4,6-tri fluorobenzylidene)-2H-benzo[b][1,4]thiazin-3(4H)-one; (Z)-methyl 4-((6-((2,6-dimethoxybenzyl)sulfonyl)-3-oxo-3,4-dihydro-2H-benzo[b][1,4]thiazin-2-ylidene)methyl)benzoate; (Z)-methyl 4-((6-((2,6-dimethoxybenzyl)sulfonyl)-3-oxo-3,4-dihydro-2H-benzo[b][1,4]thiazin-2-ylidene)methyl)-3-nitrobenzoate; (Z)-4-((6-((2,6-dimethoxybenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dimethoxybenzyl)sulfonyl)-2H-benzo[b][1,4]thiazin-3(4H)-one; (Z)-2-(4-(benzyloxy)-3-nitrobenzylidene)-6-((2,6-dimethoxybenzyl)sulfonyl)-2H-benzo[b][1,4]thiazin-3(4H)-one; and (Z)-6-((2,6-dimethoxybenzyl)sulfonyl)-2-(4-hydroxy-3-nitrobenzylidene)-2H-benzo[b][1,4]thiazin-3(4H)-one.

III. METHODS FOR PREPARING COMPOUNDS OF THE INVENTION AND INTERMEDIATES USEFUL IN THE SYNTHESIS OF COMPOUNDS OF THE INVENTION

There are provided processes for preparing compounds according to Formula I, intermediates that are useful in the preparation of such compounds, and processes for preparing such intermediates.

The compounds of Formula I can be prepared by condensing an appropriately substituted aldehyde according to Formula III Formula III

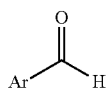

wherein Ar is as defined elsewhere herein, with a compound according to Formula IV:

Formula IV

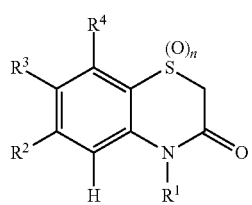

wherein $R^1$, $R^2$, $R^3$, $R^4$, and n are as defined elsewhere herein.

The aldehyde according to Formula III may be purchased from a commercial supplier such as Sigma Aldrich, or the aldehyde of Formula III may be prepared using procedures known in the art. The benzothiazinone of Formula IV can be prepared in at least two ways. For example, in one embodiment, a benzothiazinone of Formula IV can be prepared according to Scheme 1:

Scheme 1

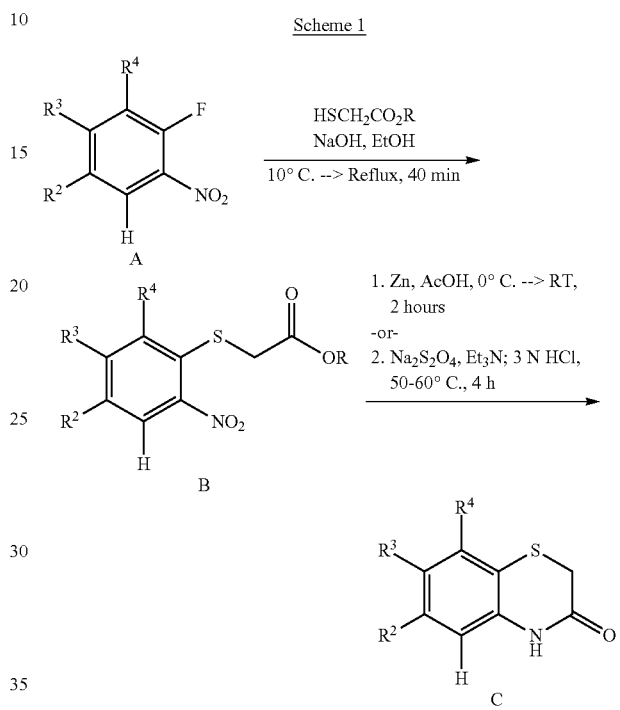

wherein, $R^2$, $R^3$, and $R^4$ are as defined previously herein.

According to Scheme 1, an appropriately substituted nitro, fluorobenzene derivative, A, is reacted with thioglycolic acid (R=H) or an ester of thioglycolic acid such as methy or ethyl thioglycolate (R=alkly) to give thioether B. The nitro group in thioether B can then be reduced. In particular embodiments, the reduction conditions employ Zn and acetic acid. In an alternative embodiment, the reduction protocol employs sodium dithionite (sodium hydrosulfite). Other nitro group reduction protocols may also be suitable. The resulting amine then undergoes in situ cyclization to give compound C, which is a compound according to Formula IV.

Optionally, the amide functionality in compound C can be alkylated or acylated via deprotonation of compound C with an appropriate base, examples of which include, but are not limited to $K_2CO_3$, NaH, potassium bis(trimethylsilyl)amide (KHMDS), sodium bis(trimethylsilyl)amide (NaHMDS), and lithium tetramethylpiperazine (LiTMP). The resulting anion can then be treated with a reactive electrophile, such as, but not limited to, an alkyl or alkenyl halide (e.g. $CH_3I$, $CH_2=CHCH_2Br$, etc.), or equivalent thereof. Alternatively, the anion can be treated with a reactive acyl species, such as, but not limited to, an acyl chloride (e.g. acetyl chloride). The resultant product is a compound of Formula IV wherein $R^1$ is other than hydrogen.

In other embodiments, the amide functionality in compound C can be arylated or heteroarylated by reacting compound C with CuI, $K_3PO_4$, an appropriately functionalized aryl or heteroaryl iodide, and trans-1,2-cyclohexanediamine (10 mol % based on the equivalents of aryl iodide) all in an appropriate solvent, examples of which include, but are not limited to, acetonitrile, toluene, dioxane, and 1,2-dimethoxyethane. Typically the reaction is warmed, and in certain embodiments, warmed to reflux. The reaction is typically carried out under an inert atmosphere. Upon completion, the reaction can be filtered through a silica gel or celite pad to remove solid impurities. The pad can be washed with additional reaction solvent to ensure that all product has been removed from the filter pad. The solvent of the resultant filtrate can then be evaporated under reduced pressure and the resultant residue purified by flash chromatography. As above, the resultant product is a compound of Formula IV wherein $R^1$ is other than hydrogen.

A compound according to Formula IV can also be prepared by functionalizing the commercially available compound 2H-1,4-benzothiazin-3(4H)-one. For example, according to Scheme 2, shown in FIG. 1, 2H-1,4-benzothiazin-3(4H)-one is reacted with chlorosulfonic acid to give 3-oxo-3,4-dihydro-2H-benzo[b][1,4]thiazine-6-sulfonyl chloride (compound "D"). Compound D can then be treated with sodium sulfite ($Na_2SO_3$) and sodium hydrogen phosphate ($Na_2HPO_4$) to give intermediate E. This intermediate can then be reacted with an appropriately substituted benzyl group to give compound F, wherein $R^{19}$, $R^{20}$, $R^{21}$, $R^{22}$, and $R^{23}$ are as defined previously herein and X is leaving group such as a halide, tosylate, mesylate, benzensulfonate, methansulfonate, or other equivalent group suitable for use in $S_N2$ type chemistry. Compound F is a compound according to Formula IV. Alternatively, compound D can be reacted with Zn metal to give a reactive Zn complex, G, which can subsequently be reacted with the above described benzyl group, to give compound F. As set forth previously, compound F is a compound of Formula IV.

Optionally, the amide functionality in compound F can be alkylated or acylated via deprotonation of compound F with an appropriate base, examples of which include, but are not limited to $K_2CO_3$, NaH, potassium bis(trimethylsilyl)amide (KHMDS), sodium bis(trimethylsilyl)amide (NaHMDS), and lithium tetramethylpiperazine (LiTMP). The resulting anion can then be treated with a reactive electrophile, such as, but not limited to, an alkyl or alkenyl halide (e.g. $CH_3I$, $CH_2$=$CHCH_2Br$, etc.), or equivalent thereof. Alternatively, the anion can be treated with a reactive acyl species, such as, but not limited to, an acyl chloride (e.g. acetyl chloride). The resultant product is a compound of Formula IV wherein $R^1$ is other than hydrogen.

In other embodiments, the amide functionality in compound F can be arylated or heteroarylated by reacting compound F with CuI, $K_3PO_4$, an appropriately functionalized aryl or heteroaryl iodide, and trans-1,2-cyclohexanediamine (10 mol % based on the equivalents of aryl iodide) all in an appropriate solvent, examples of which include, but are not limited to, acetonitrile, toluene, dioxane, and 1,2-dimethoxyethane. Typically the reaction is warmed, and in certain embodiments, warmed to reflux. The reaction is typically carried out under an inert atmosphere. Upon completion, the reaction can be filtered through a silica gel or celite pad to remove solid impurities. The pad can be washed with additional reaction solvent to ensure that all product has been removed from the filter pad. The solvent of the resultant filtrate can then be evaporated under reduced pressure and the resultant residue purified by flash chromatography. As above, the resultant product is a compound of Formula IV wherein $R^1$ is other than hydrogen.

The aldehyde of Formula III can then be condensed with the compound of Formula IV to give a compound of Formula I. In certain embodiments, the condensation reaction takes place in the presence of a suitable base and an anhydride, wherein the anhydride acts as the solvent for the reaction. In other embodiments, the reaction can be run in a solvent other than the anhydride, examples of which include, but are not limited to toluene and acetic acid. In particular embodiments, the base is triethylamine ($Et_3N$) and the anhydride is acetic anhydride ($Ac_2O$). Other suitable bases, and in particular amine bases, can be substituted for $Et_3N$. Example of other suitable bases include, but are not limited to, di-isopropylethy amine. Likewise, other suitable anhydrides can be used. Examples include, but are not limited to propionoic anhydride and butyric anhydride. The resulting mixture can be then be warmed, and in certain embodiments, heated to reflux to give a compound of Formula I. An exemplary reaction scheme is provided in Scheme 3:

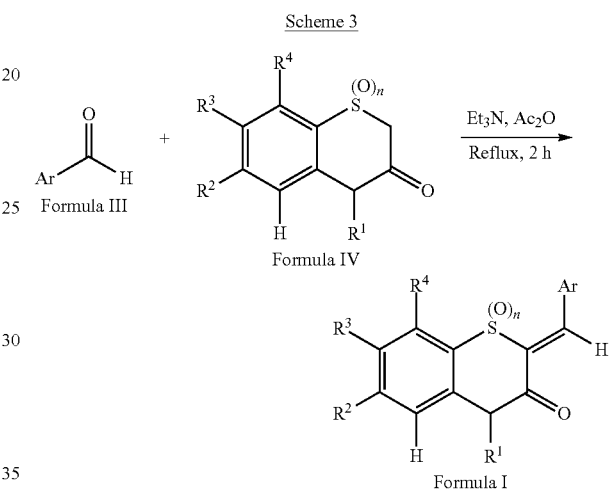

In certain embodiments, the above-described reaction may result in a compound of Formula I wherein $R^1$ is hydrogen. The nitrogen bound to $R^1$ can be further functionalized via selective arylation, heteroarylation, alkylation, or acylation according to the procedures described elsewhere herein for compounds C and F.

Compounds of the invention can be prepared and used as their benzothiazinone-1-oxides, i.e. compounds of Formula I wherein n is 1. These compounds can be prepared by oxidizing a compound of Formula I (or appropriately functionalized intermediate useful for the preparation of a compound of Formula I) with an oxidizing agent such as meta-chloroperoxybenzoic acid (MCPBA) in a solvent such as, but not limited to, dichloromethane. After appropriate basic aqueous workup, the oxidized compound of Formula I can typically be isolated in high yield and purity after recrystallization or flash chromatography.

Compounds of the invention can also be prepared and used as their benzothiazinone-1,1-dioxides, i.e. compounds of Formula I wherein n=2. These compounds can be prepared by oxidizing a compound of Formula I (or appropriately functionalized intermediate useful for the preparation of a compound of Formula I) with an oxidizing agent such as hydrogen peroxide in a solvent such as, but not limited to, acetic acid. After appropriate aqueous workup, the desired compound can typically be isolated in high yield after recrystallization or flash chromatography.

Although compounds of Formula I are generally produced as their Z isomers, the compounds of the invention can be converted to their E isomeric forms via a photo-induced isomerization (either sunlight or UV/VIS radiation) according to the procedure described in Kamila, et al., "Synthesis of (Z)-hetarylmethylene and (Z)-substituted benzylidene derivatives of 4H-benzo[1,4]thiazine-3-thiones and their subsequent conversion to benzothiopyrano-[3,2-b][1,4]benzothiazines" ARKIVOC 2006 (ii) 1-14, the entirety of which is hereby incorporated by reference.

IV. ANTIBODY CONJUGATES

Another aspect of the invention relates to antibody conjugates of compounds of Formula I, wherein said antibody conjugates have the Formula I-L-Ab. The present invention further includes salts of the antibody conjugates. In the Formula I-L-Ab, "I" is a compound of Formula I; Ab is an antibody; and -L- is a single bond or a linking group covalently linking said compound of Formula I to said antibody.

In a preferred sub-embodiment of the aforesaid conjugates of the Formula I-L-Ab, said antibody (Ab) is a monoclonal antibody or a monospecific polyclonal antibody.

In a more preferred sub-embodiment of the aforesaid conjugates of the formulae I-L-Ab, the aforesaid antibody (Ab) is a tumor-specific antibody.

Antibodies, preferably monoclonal antibodies and monospecific polyclonal antibodies, and most preferably tumor-specific antibodies, may be covalently linked to compounds of the present invention. A "tumor-specific antibody" is an antibody which specifically binds to a tumor antigen, e.g., an antigen on a tumor cell.

The covalent linker between a compound of Formula I and an antibody may, in its simplest form, comprise a single covalent bond connecting the compound of Formula I to the antibody. More commonly the compound of Formula I is attached to the antibody using a suitable bifunctional linking reagent. The term "bifunctional linking reagent" refers generally to a molecule that comprises two reactive moieties which are connected by a spacer element. The term "reactive moieties", in this context, refers to chemical functional groups capable of coupling with an antibody or a compound of Formula I by reacting with functional groups on the antibody and the compound of Formula I.

An example of a covalent bond formed as a linker between a compound of Formula I and an antibody is a disulfide bond formed by the oxidation of an antibody and a compound of Formula I wherein n is 0 and wherein a linking group is used that contains one or more cysteine amino acids. The cysteine residues can be oxidized to form disulfide links by dissolving 1 mg of the a suitable compound of Formula I and 0.5 equivalents of the desired antibody in 1.5 ml of 0.1% (v/v) 17.5 mM acetic acid, pH 8.4, followed by flushing with nitrogen and then 0.01 M $K_2Fe(CN)_6$. After incubation for one hour at room temperature, the adduct peptide is purified by HPLC.

Another example of a suitable covalent bond formed as a linker between a compound of Formula I and an antibody is an amide bond formed by reacting an amino group on a compound of the invention with a carboxylic acid group which forms part of the primary structure of the antibody (Ab) (such as, for example a glutamic or aspartic amino acid residue). Alternately, an amide bond could be formed if the reacting moieties were reversed, i.e., the compound of Formula I could contain a carboxylic acid functionality and react with an amino functionality within the Ab structure.

Alternatively, a compound of Formula I and an antibody Ab may be covalently linked using a bifunctional linking reagent.

For example, adducts can be prepared by first preparing S—(—N-hexylsuccinimido)-modified derivatives of an antibody and of a compound of Formula I, according to the method of Cheronis et al., *J. Med. Chem.* 37: 348 (1994) (the entire disclosure of which is incorporated herein by reference). N-hexylmaleimide, a precursor for the modified antibody and compound of Formula I, is prepared from N-(methoxycarbonyl)maleimide and N-hexylamine by mixing the two compounds in saturated $NaHCO_3$ at 0° C. according to the procedure of Bodanszky and Bodanszky, *The Practice of Peptide Synthesis*; Springer-Verlag, New York, pp. 29-31 (1984)(the entire disclosure of which is incorporated herein by reference). The product of the resulting reaction mixture is isolated by extraction into ethyl acetate, followed by washing with water, dried over $Na_2SO_4$, and is then concentrated in vacuo to produce N-hexylmaleimide as a light yellow oil. S—(N-Hexylsuccinimido)-modified antibody and Formula I compound are then prepared from a cysteine-containing peptide and N-hexylmaleimide by mixing one part peptide with 1.5 parts N-hexylmaleimide in N,N-dimethylformamide (3.3 mL/mM peptide) followed by addition to 30 volumes of 0.1 M ammonium bicarbonate, pH 7.5. The S-alkylation reaction carried out in this manner is complete in 30 minutes. The resulting S—(N-hexylsuccinimido)-modified peptide monomer is purified by preparative reverse-phase HPLC, followed by lyophilization as a fluffy, white powder.

Bis-succinimidohexane peptide heterodimers (wherein one peptide is the antibody and the other peptide is attached to the Formula I compound) may be prepared according to the method of Cheronis et al., supra from cysteine-substituted peptides. A mixture of one part bismaleimidohexane is made with two parts peptide monomer in N,N-dimethylformamide (3.3 mL/mM peptide) followed by addition to 0.1 ammonium bicarbonate, pH 7.5. The reaction mixture is stirred at room temperature and is usually completed within 30 minutes. The resulting bis-succinimidohexane peptide dimer is purified by preparative reverse-phase HPLC. After lyophilization the material is a fluffy, white powder.

Covalently linked adducts of the general Formula I-L-Ab of the present invention may be prepared by utilizing homo-bifunctional linking reagents (wherein the two reactive moieties are the same), such as, for example, disuccinimidyl tartrate, disuccinimidyl suberate, ethylene glycolbis-(succinimidyl succinate), 1,5-difluoro-2,4-dinitrobenzene ("DFNB"), 4,4'-diisothiocyano-2,2'-disulfonic acid stilbene ("DIDS"), and bis-maleimidohexane ("BMH").

Alternatively, hetero-bifunctional linking reagents may be employed. Such agents include, for example, N-succinimidyl-3-(2-pyridyldithio)propionate ("SPDP"), sulfosuccinimidyl-2-(p-azidosalicylamido)ethyl-1-3'-dithiopropionate ("SASD", Pierce Chemical Company, Rockford, Ill.), N-maleimidobenzoyl-N-hydroxy-succinimidyl ester ("MBS"), m-maleimidobenzoylsulfosuccinimide ester ("sulfo-MBS"), N-succinimidyl(4-iodoacetyl)aminobenzoate ("SIAB"), succinimidyl 4-(N-maleimidomethyl)-cyclohexane-1-carboxylate ("SMCC"), succinimidyl-4-(p-maleimidophenyl)butyrate ("SMPB"), sulfosuccinimidyl(4-iodoacetyl)aminobenzoate ("sulfo-SIAB"), sulfosuccinimidyl 4-(N-maleimidomethyl)cyclohexane-1-carboxylate ("sulfo-SMCC"), sulfosuccinimidyl 4-(p-maleimidophenyl)-butyrate ("sulfo-SMPB"), bromoacetyl-p-aminobenzoyl-N-hydroxy-succinimidyl ester, iodoacetyl-N-hydroxysuccinimidyl ester, and the like.

For hetero-bifunctional linking, a compound of Formula I is derivatized with, for example, the N-hydroxysuccinimidyl portion of the bifunctional reagent, and the resulting derivatized compound is purified by chromatography. Next, a suitable tumor-specific Mab is reacted with the second functional group of the bifunctional linking reagent, assuring a directed sequence of binding between components of the desired adduct.

Typical hetero-bifunctional linking agents for forming protein-protein conjugates have an amino-reactive N-hydroxysuccinimide ester (NHS-ester) as one functional group and a sulfhydryl reactive group as the other functional group. First, epsilon-amino groups of surface lysine residues of either the Mab or the Formula I compound are acylated with the NHS-ester group of the cross-linking agent. The remaining component, possessing free sulfhydryl groups, is reacted with the sulfhydryl reactive group of the cross-linking agent to form a covalently cross-linked dimer. Common thiol reactive groups include, for example, maleimides, pyridyl disulfides, and active halogens. For example, MBS contains a NHS-ester as the amino reactive group, and a maleimide moiety as the sulfhydryl reactive group.

Photoactive hetero-bifunctional linking reagents, e.g., photoreactive phenyl azides, may also be employed. One such reagent, SASD, may be linked to either a Mab or to a Formula I compound wherein with an attached peptidyl group, via its NHS-ester group. The conjugation reaction is carried out at pH 7 at room temperature for about 10 minutes. Molar ratios between about 1 and about 20 of the cross-linking agent to the compounds to be linked may be used.

Numerous bifunctional linkers, useful as linkers (-L-), exist which have been used specifically for coupling small molecules to monoclonal antibodies, and many of these are commercially available. Examples include N-succinimidyl-3-(2-pyridyldithio)-propionate (SPDP), 2-iminothiolane (2-IT), 3-(4-carboxamidophenyldithio)propionthioimidate (CDPT), N-succinimidyl-acetylthioacetate (SATA), ethyl-S-acetyl-propionthioimidate (AMPT) and N-succinimidyl-3-(4-carboxamidophenyldithio)propionate (SCDP). Procedures for preparation of immunoconjugates using these linkers is detailed in Cattel, et al, "Toxin-Targeted Design for Anticancer Therapy II: Preparation and Biological Comparison of Different Chemically Linked Gelonin-Antibody Conjugates", *J. Pharm. Sci.*, 1993, 82, 699-704, the entire disclosure of which is incorporated herein by reference.

V. Treatment of Cellular Proliferative Disorders Using Compounds of the Invention According to another embodiment of the invention, a method of treating an individual suffering from a cellular proliferative disorder, particularly cancer, is provided, comprising administering to said individual an effective amount of at least one compound according to Formula I, or a pharmaceutically acceptable salt thereof, either alone, or in combination with a pharmaceutically acceptable carrier.

According to another embodiment of the invention, a method of inducing apoptosis of cancer cells, preferably tumor cells, in an individual afflicted with cancer is provided, comprising administering to said individual an effective amount of at least one compound according to Formula I, or a pharmaceutically acceptable salt thereof, either alone, or in combination with a pharmaceutically acceptable carrier.

According to another embodiment of the invention, a method of treating an individual suffering from a cellular proliferative disorder, particularly cancer, is provided, comprising administering to said individual an effective amount of at least one conjugate of the Formula I-L-Ab, either alone, or in combination with a pharmaceutically acceptable carrier.

The invention is also directed to the use in medicine of a compound according to Formula I, or a pharmaceutically acceptable salt thereof, or a conjugate according to Formula I-L-Ab, or a pharmaceutically acceptable salt thereof The invention is also directed to the use of a compound according to Formula I, or a pharmaceutically acceptable salt thereof, or a conjugate according to Formula I-L-Ab, or a pharmaceutically acceptable salt thereof, in the preparation of a medicament for treatment of a cellular proliferative disorder, particularly cancer, or for inducing apoptosis of tumor cells in an individual affected with cancer.

Particular and preferred embodiments of this aspect of the invention are those wherein the compound of Formula I used in the method of treatment, either alone or as part of a composition, or as a component of the antibody conjugate, is a particular or preferred embodiment of the compound of Formula I in the description of the compounds and compositions of the invention as provided herein.

The compounds according to the invention may be administered to individuals (mammals, including animals and humans) afflicted with a cellular proliferative disorder such as cancer, malignant and benign tumors, blood vessel proliferative disorders, autoimmune disorders, and fibrotic disorders. In a particular embodiment of the invention, the individual treated is a human.

The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate. Non-cancer cellular proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X-linked lymphocellular proliferative disorder (Duncan disease), post-transplantation lymphocellular proliferative disorder (PTLD), macular degeneration, and retinopathies, such as diabetic retinopathies and proliferative vitreoretinopathy (PVR)

Other non-cancer cellular proliferative disorders believed treatable by compounds according to the invention include the presence of pre-cancerous lymphoproliferative cells associated with an elevated risk of progression to a cancerous disorder. Many non-cancerous lymphocellular proliferative disorders are associated with latent viral infections such as Epstein-Barr virus (EBV) and Hepatitis C. These disorders often begin as a benign pathology and progress into lymphoid neoplasia as a function of time.

VI. Salts of Compounds According to the Invention

The compounds of the present invention may take the form of salts when appropriately substituted with groups or atoms capable of forming salts. Such groups and atoms are well known to those of ordinary skill in the art of organic chemistry. The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aralipathic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound according to Formula I by reacting, for example, the appropriate acid or base with the compound according to Formula I. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

VII. Pharmaceutical Compositions

The compounds of the invention may be administered in the form of a pharmaceutical composition, in combination with a pharmaceutically acceptable carrier. The active ingredient or agent in such formulations (i.e. a compound of Formula I) may comprise from 0.1 to 99.99 weight percent of the formulation. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the cellular proliferative disorder, the aggressiveness of the cellular proliferative disorder, and the route of administration of the compound.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VIII. Routes of Administration of Compounds and Compositions of the Invention

The compounds of Formula I may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present inventions may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

IX. Isomerism in Compounds of the Invention

Geometrical Isomerism

The compounds of Formula I possess an olefinic double bond. The stereochemistry of compounds possessing an olefinic double bond is designated using the nomenclature using E and Z designations. The compounds are named according to the Cahn-Ingold-Prelog system, described in the IUPAC 1974 Recommendations, Section E: Stereochemistry, in *Nomenclature of Organic Chemistry*, John Wiley & Sons, Inc., New York, N.Y., 4<sup>th</sup> ed., 1992, pp. 127-38, the entire contents of which is incorporated herein by reference. Using this system of nomenclature, the four groups about a double bond are prioritized according to a series of rules wherein various functional groups are ranked. The isomer with the two higher ranking groups on the same side of the double bond is designated Z and the other isomer, in which the two higher ranking groups are on opposite sides of the double bond, is designated E. This is illustrated schematically, below, where the Cahn-Ingold-Prelog system priority of the double bond substituents A is greater than that of B, and the priority of A' is greater than that of B'.

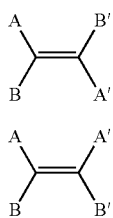

(E) isomer (Z) isomer

The compounds of Formula I prepared according to the methodology described herein are believed to be in their Z isomeric forms, but may be converted to their E isomeric forms as previously described herein. Thus, both E and Z isomeric forms of each compound described herein are contemplated and may be generically described in a compound including a "wavy" bond pendant to a double bond, such as:

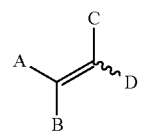

This generic structure indicates that a given compound may have either the E or Z configuration, such that the compounds

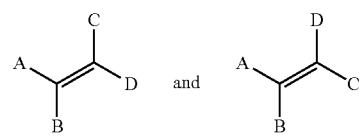

would be understood to be described by the single structure provided above. As used herein, the presence of a wavy bond pendant to a double bond is not a per se indication of an impure mixture of compounds having both E and Z configurations. Rather, as set forth elsewhere herein, the presence of a wavy bond indicates either (E), (Z), or a mixture of configurations of the double bond to the carbon atom to which the wavy bond is attached.

B. Optical Isomerism

It will be understood that when or if compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking is A>B>C>D. The lowest ranking atom, D is oriented away from the viewer.

(R) configuration (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

C. Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of Formula I.

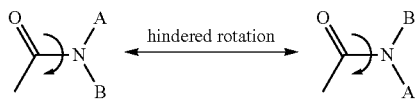

EXAMPLES

The following non-limiting examples are provided to illustrate the invention. The synthetic procedures described as "general methods" describe what it is believed will be typically effective to perform the synthesis indicated. However, the person skilled in the art will appreciate that it may be necessary to vary the procedures for any given embodiment of the invention. For example, reaction monitoring, such as by using thin layer chromatography, or HPLC may be used to determine the optimum reaction time. Products may be purified by conventional techniques that will vary, for example, according to the amount of side products produced and the physical properties of the compounds. On a laboratory scale, recrystallisation from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al, *Experimental Organic Chemistry: Standard and Microscale*, by L. M. Harwood et al. ($2^{nd}$ Ed., Blackwell Scientific Publications, 1998), and Advanced Practical Organic Chemistry, by J. Leonard, et al. ($2^{nd}$ Edition, CRC Press 1994).

Synthetic Examples

Example 1

General Preparation of Compound B According to Scheme 1

Thioglycolic acid or methyl thioglycolate (1 mole) was added to a stirred solution of sodium hydroxide (2 mole) in ethanol (30 ml) and stirred for 5 min at room temperature. Compound A (1 mole) was added to the above solution and the reaction was refluxed for 1 h. Progress of the reaction was monitored by TLC. Upon completion, the reaction mixture was allowed to cool to room temperature, poured into crushed ice, and subsequently neutralized with 10N hydrochloric acid. The resulting solid was collected via filtration, washed with water and hexane, and dried to give compound B.

Exemplary compounds produced according to this methodology, along with their relevant $^1$H NMR characteristics, and liquid chromatography mass spectrum (LCMS), are shown in Table 2.

TABLE 2

| Cpd. # | Cpd. Name | Structure | $^1$H NMR (DMSO-$d_6$, 600 MHz) | LCMS |
|---|---|---|---|---|
| 45 | 2-((4-Fluoro-2-nitrophenyl)thio)acetic acid | 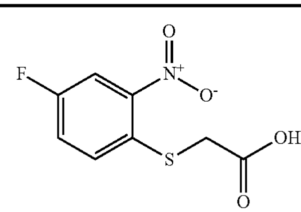 | δ 8.14 (d, 1H, Ar—H, J = 8.1 Hz), 7.73-7.66 (m, 2H, Ar—H), 4.04 (s, 2H, S—CH$_2$—CO) | (M + Na): 253.98 |
| 46 | 4-((2-Methoxy-2-oxoethyl)thio)-3-nitrobenzoic acid | 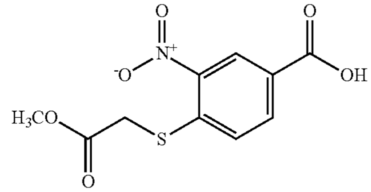 | δ 13.64 (brs, 1H, COOH), 8.64 (s, 1H, Ar—H), 8.16 (d, 1H, Ar—H, J = 6.0 Hz), 7.68 (d, 1H, Ar—H, J = 6.4 Hz) 4.24 (s, 2H, S—CH$_2$—CO), 3.69 (s, 3H, OCH$_3$) | N/D |

Example 2

General Preparation of Compound C According to Scheme 1

Method 1: Reductive Cyclization with Zn/AcOH:

Compound B (8.6 mmole) was dissolved in 90 ml of acetic acid in a round bottom flask with stirring for 5-10 minutes. The reaction was cooled to 0° C. using an ice bath. Zn dust (14.4 g) was slowly added to the stirring reaction, all the while maintaining the temperature at 0° C. Upon complete addition the reaction mixture was maintained at 0° C. for an additional 60 minutes. The reaction was subsequently warmed to room temperature and allowed to stir for an additional two hours. The reaction was subsequently filtered through a ceilite pad. The resultant filtrate was then evaporated to give compound C.

Method 2: Reductive Cyclization with $Na_2S_2O_4$:

Sodium hydrosulfite (10 mmol) was added portion wise (in 4 portions at 5 min intervals) to a stirred solution of compound B (5 mmol) in 2:1 ethanol:water (20-30 ml) and triethylamine (20 mmol). The temperature of the reaction was kept at 50° C. during the addition of the hydrosulfite. Upon complete addition, the reaction was maintained at 50° C. for 1.5 hours and then cooled to room temperature. Subsequently, 3N HCl (20 ml) was added and the reaction was warmed to 60° C. After 1 hour, the reaction mixture was poured into crushed ice (300 g) with vigorous stirring. A solid precipitate that had formed was collected via filtration. The solid was subsequently washed with 1:1 ether/hexane and dried under vacuum to provide pure C.

Exemplary compounds produced according to the procedures of Example 2, along with their relevant $^1$H NMR characteristics, and LCMS peaks, are shown in Table 3.

Example 3

Preparation of 3-oxo-3,4-dihydro-2H-benzo[1,4]thiazine-6-sulfonyl chloride (Compound D, Scheme 2)

Chlorosulfonic acid (55.93 g, 0.48 mole) was added to a 250 mL round bottom flask under nitrogen at 10° C. To this, 4H-benzo[1,4]thiazin-3-one, (20 g, 0.12 mole) was added slowly so that the reaction temperature was maintained below 20° C. during the addition. After addition, the reaction mixture was stirred at room temperature for 1.5 h and then heated to 65° C. for an additional 1 hour. The reaction was subsequently cooled and poured into ice-cold water. A solid precipitate formed and was collected via filtration. The solid was then washed with water and dried to provide 23.6 g of the title compound (75% yield). $^1$H NMR (CDCl$_3$, 300 MHz): δ 9.08 (br s, NH), 7.72-7.88 (m, 3H, Ar—H), 3.68 (s, 2H, Ar—CH$_2$); m.p.: 165-167° C.; LC-MS (M+1): 263.92

Example 4

Preparation of 6-((2,6-dichlorobenzyl)sulfonyl)-2H-benzo[b][1,4]thiazin-3(4M-one

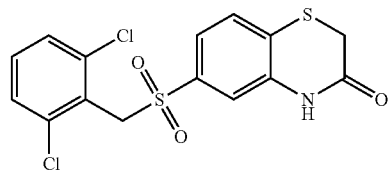

6-((2,6-dichlorobenzyl)sulfonyl)-2H-benzo[b][1,4]thiazin-3(4H)-one.

TABLE 3

| Cpd. # | Cmpd. Name | Structure | $^1$H NMR | LCMS |
|---|---|---|---|---|
| 47 | 6-fluoro-2H-benzo[b][1,4]thiazin-3(4H)-one | 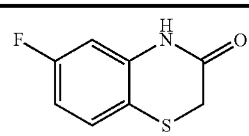 | (CDCl$_3$, 600 MHz): δ 8.70 (brs, 1H, NH), 7.31 (d, 1H, Ar—H, J = 8.3 Hz), 6.80 (s, 1H, Ar—H), 6.69 (d, 1H, Ar—H, J = 8.6 Hz), 3.47 (s, 2H, C$_2$—H) | (M + 1): 184.02 |
| 48 | 7-Bromo-2H-benzo[b][1,4]thiazin-3(4H)-one | 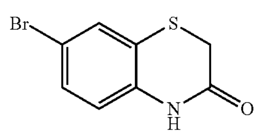 | (DMSO-d$_6$, 300 MHz): δ 10.67 (brs, 1H, NH), 7.55 (d, 1H, Ar—H, J = 1.4 Hz), 7.37-7.34 (dd, 1H, Ar—H, J = 1.5 & 6.4 Hz), 6.91 (d, 1H, Ar—H, J = 6.4 Hz), 3.49 (s, 2H, C$_2$—H) | N/D |
| 49 | 3-Oxo-3,4-dihydro-2H-benzo[b][1,4]thiazine-6-carboxylic acid | 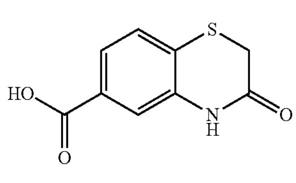 [SMILES: O=C1CSc2ccc(C(=O)O)cc2N1] | (DMSO-d$_6$, 300 MHz): δ 13.02 (brs, 1H, COOH), 10.79 (brs, 1H, NH), 7.60 (s, 1H, Ar—H), 7.55 (d, 1H, Ar—H, J = 8.4 Hz), 7.47 (d, 1H, Ar—H, J = 8.4 Hz), 3.58 (s, 2H, C$_2$—H) | N/D |
| 50 | 6-Amino-2H-benzo[b][1,4]thiazin-3(4H)-one (3d) | 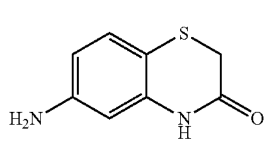 [SMILES: Nc1ccc2c(c1)NC(=O)CS2] | $^1$H NMR (DMSO-d$_6$, 300 MHz): δ 10.34 (brs, 1H, NH), 6.96 (d, 1H, Ar—H, J = 6.0 Hz), 6.29-6.26 (m, 2H, Ar—H), 5.25 (brs, 2H, NH$_2$), 3.37 (s, 2H, C$_2$—H) | N/D |

Method 1: Zn-Mediated Sulfonylation:

Zn dust (1.3 g, 17 mmol), was added to THF/water (2:1) 150 ml and stirred for 15 min. Sold compound D (5 g, 19 mmol) was added to the Zn THF/water mixture over 30 min, so that the addition exotherm could be controlled. The heterogeneous solution was then stirred for 24 h. The reaction was subsequently filtered through celite and the filtrate collected. The celite pad was subsequently washed with ethyl acetate. The organic layers were then combined and dried over anhydrous $Na_2SO_4$. The drying agent was filtered away and the filtrate was evaporated under reduced pressure to give Compound G, Scheme 2, which was used without further characterization or purification.

2,6-Dichlorobenzyl bromide (3.0 g, 39.6 mmol) in THF/water (2:1) (70 ml) was added to the above Zn complex and stirred at 70° C. for 5 h. Upon completion of the reaction, the reaction mixture was diluted with ice-cold water, quenched with 2N HCl (5 mL), and stirred for 10 min. A white solid precipitated. The precipitate was collected via filtration, washed with cold water, cold methanol (30 ml), and subsequently dried to give 3.5 g of 6-((2,6-dichlorobenzyl)sulfonyl)-2H-benzo[b][1,4]thiazin-3(4H)-one (50% yield). $^1$H NMR (DMSO-$d_6$, 300 MHz): δ 10.95 (br s, 1H, NH), 7.16-7.80 (m, 6H, Ar—H), 4.88 (s, 2H, Ar—$CH_2$), 3.46 (s, 2H, $C_2$—H); m.p.: 244-246° C.; LC-MS (M+1): 387.96.

Method 2: Sulfite-Mediated Sulfonylation:

$Na_2HPO_4$ (2.3 g, 20 mmol) and $Na_2SO_3$ (4.8 g, 38 mmol) were dissolved in 100 ml of water at 30° C. This solution was then added to Compound D (5 g, 19 mmol) resulting in the formation of a creamy suspension. The resultant suspension was heated to 60° C. and became a clear solution. The reaction was stirred at 60° C. for 16 h. Subsequently, 2,6-dichlorobenzyl bromide (4.5 g, 19 mmol) in 10 ml of acetone was added to the reaction over 15 minutes. The reaction was then stirred for 2 hours at 60° C. Upon completion of the reaction, the reaction vessel was cooled and reaction was poured into ice-cold water and stirred for 1 h. A white precipitate formed and was collected via filtration. The collected solid was washed with cold water and a cold 1:1 water/acetone mixture. The resultant solid was subsequently dried under vacuum at 60° C. overnight to give 6.8 g (93% yield) of white 6-((2,6-dichlorobenzyl)sulfonyl)-2H-benzo[b][1,4]thiazin-3(4M-one. $^1$H NMR (DMSO-$d_6$, 300 MHz): δ 10.98 (br s, 1H, NH), 7.27-7.65 (m, 6H, Ar—H), 4.95 (s, 2H, Ar—$CH_2$), 3.58 (s, 2H, $C_2$—H); m.p.: 244-246° C.; LC-MS (M+1): 387.96.

Example 5

General Procedure for the Preparation of Compounds of Formula I According to Scheme 3

A compound according to Formula IV (1 mmol), an aldehyde of Formula III (1 mmol), triethylamine (4 mmol), and acetic anhydride (10 ml) were refluxed under nitrogen atmosphere for 2 h. The reaction mixture was cooled to room temperature. Solvent was removed under reduced pressure and the resulting residue was purified by column chromatography to give a compound of Formula I. In certain instances, a solid precipitate formed upon completion and/or cooling the reaction. In either case, the precipitate was collected via filtration. Subsequently, the filtered solid was washed with an appropriate solvent and dried under vacuum to give a compound of Formula I.

Example 6

Additional Data for Compounds of the Invention

The compounds of the invention were prepared using the general procedures described above. Table 4, below, identifies compounds of the invention by number as well as the starting benzothiazinone and aldehyde used to prepare the compound. Table 4 further includes the $^1$H NMR and LCMS peak of the identified compound of the invention. $^1$H NMR spectra were recorded in either $CDCl_3$ or in DMSO-$d_6$, as set forth in the table.

TABLE 4

| Cpd. # | Starting Benzothiazinone | Starting Aldehye | m.p. (° C.) | $^1$H NMR (δ ppm) | LC-MS (M + 1) |
|---|---|---|---|---|---|
| 1 | Cl-substituted benzo[1,4]thiazin-3-one | 3-NO$_2$, 4-OC(O)CH$_3$ benzaldehyde | 268-270 | (DMSO-$d_6$; 300 MHz): 11.30 (brs, 1H, NH), 8.42 (d, 1H, Ar—H, J = 1.5 Hz), 8.10-8.07 (dd, 1H, Ar—H, J = 1.5 & 6.4 Hz), 7.88 (s, 1H, =CH), 7.62 (d, 1H, Ar—H, J = 6.4 Hz), 7.55 (d, 1H, Ar—H, J = 1.6 Hz), 7.30-7.27 (dd, 1H, Ar—H, J = 1.7 & 6.5 Hz), 7.08 (d, 1H, Ar—H, J = 6.5 Hz), 2.37 (s, 3H, COCH$_3$) | 391.02 |
| 2 | H$_3$CO-substituted benzo[1,4]thiazin-3-one | 3-NO$_2$, 4-OC(O)CH$_3$ benzaldehyde | 238-240 | (DMSO-$d_6$; 300 MHz): 11.06 (brs, 1H, NH), 8.41 (s, 1H, Ar—H), 8.09 (d, 1H, Ar—H, J = 6.4 Hz), 7.86 (s, 1H, =CH), 7.61 (d, 1H, Ar—H, J = 6.3 Hz), 7.03 (d, 1H, Ar—H, J = 6.7 Hz), 6.99 (s, 1H, Ar—H), 6.83 (d, 1H, Ar—H, J = 6.4 Hz), 3.72 (s, 3H, OCH$_3$), 2.37 (s, 3H, COCH$_3$) | 387.07 |

TABLE 4-continued

| Cpd. # | Starting Benzothiazinone | Starting Aldehye | m.p. (° C.) | ¹H NMR (δ ppm) | LC-MS (M + 1) |
|---|---|---|---|---|---|
| 3 | 7-Bromo-2H-benzo[b][1,4]thiazin-3(4H)-one | 4-acetoxy-3-nitrobenzaldehyde | 270-272 | (DMSO-$d_6$; 300 MHz): 11.34 (brs, 1H, NH), 8.46 (d, 1H, Ar—H, J = 1.1 Hz), 8.14-8.11 (dd, 1H, Ar—H, J = 1.2 & 6.4 Hz), 7.92 (s, 1H, =CH), 7.70 (d, 1H, Ar—H, J = 1.2 Hz), 7.66 (d, 1H, Ar—H, J = 6.4 Hz), 7.46-7.43 (dd, 1H, Ar—H, J = 1.3 & 6.4 Hz), 7.06 (d, 1H, Ar—H, J = 6.4 Hz), 2.41 (s, 3H, COCH$_3$) | 436.28 |
| 4 | 7-Methyl-2H-benzo[b][1,4]thiazin-3(4H)-one | 4-acetoxy-3-nitrobenzaldehyde | 236-238 | (DMSO-$d_6$; 300 MHz): 11.00 (brs, 1H, NH), 8.31 (d, 1H, Ar—H, J = 1.5 Hz), 7.97-7.95 (dd, 1H, Ar—H, J = 1.5 & 6.4 Hz), 7.73 (s, 1H, =CH), 7.48 (d, 1H, Ar—H, J = 6.3 Hz), 7.06 (s, 1H, Ar—H), 6.91 (d, 1H, Ar—H, J = 6.2 Hz), 6.86 (d, 1H, Ar—H, J = 6.1 Hz), 2.24 (s, 3H, COCH$_3$), 2.10 (s, 3H, Ar—CH$_3$) | 371.35 |
| 5 | 3-oxo-3,4-dihydro-2H-benzo[b][1,4]thiazine-7-carboxylic acid | 4-acetoxy-3-nitrobenzaldehyde | >300 | (DMSO-$d_6$; 300 MHz): 11.01 (brs, 1H, NH), 8.22 (d, 1H, Ar—H, J = 1.5 Hz), 7.90-7.88 (dd, 1H, Ar—H, J = 1.5 & 6.4 Hz), 7.65 (s, 1H, =CH), 7.48 (s, 1H, Ar—H), 7.39 (d, 1H, Ar—H, J = 6.3 Hz), 7.35 (d, 1H, Ar—H, J = 5.7 Hz), 7.06 (d, 1H, Ar—H, J = 6.0 Hz), 2.15 (s, 3H, COCH$_3$) | 401.38 |
| 6 | 6-Fluoro-2H-benzo[b][1,4]thiazin-3(4H)-one | 4-acetoxy-3-nitrobenzaldehyde | 238-240 | (DMSO-$d_6$; 300 MHz): 11.22 (brs, 1H, NH), 8.41 (d, 1H, Ar—H, J = 1.5 Hz), 8.09-8.06 (dd, 1H, Ar—H, J = 1.6 & 6.4 Hz), 7.88 (s, 1H, =CH), 7.62 (d, 1H, Ar—H, J = 6.4 Hz), 7.38 (d, 1H, Ar—H, J = 6.6 Hz), 7.13 (d, 2H, Ar—H, J = 8.0 Hz), 2.37 (s, 3H, COCH$_3$) | 375.05 |
| 7 | 6-Fluoro-2H-benzo[b][1,4]thiazin-2-one | 4-acetoxy-3-nitrobenzaldehyde | 236-238 | (DMSO-$d_6$; 300 MHz): 11.25 (brs, 1H, NH), 8.39 (s, 1H, Ar—H), 8.06 (d, 1H, Ar—H, J = 6.2 Hz), 7.83 (s, 1H, =CH), 7.58 (d, 1H, Ar—H, J = 6.3 Hz), 7.38 (t, 1H, Ar—H, J = 5.0 & 5.2 Hz), 6.91-6.87 (m, 2H, Ar—H), 2.37 (s, 3H, COCH$_3$) | 375.09 |

TABLE 4-continued

| Cpd. # | Starting Benzothiazinone | Starting Aldehyde | m.p. (°C.) | ¹H NMR (δ ppm) | LC-MS (M + 1) |
|---|---|---|---|---|---|
| 8 | 6-((2,6-dichlorobenzyl)sulfonyl)-2H-benzo[b][1,4]thiazin-3(4H)-one (Example 4) | 4-acetoxy-3-nitrobenzaldehyde | 286-288 | (DMSO-d$_6$; 300 MHz): 11.42 (brs, 1H, NH), 8.43 (d, 1H, Ar—H, J = 2.4 Hz), 8.11-8.08 (dd, 1H, Ar—H, J = 2.1 & 8.5 Hz), 7.91 (s, 1H, =CH), 7.62 (d, 1H, Ar—H, J = 1.0 Hz), 7.53 (d, 1H, Ar—H, J = 1.2 Hz), 7.50 (s, 1H, Ar—H), 7.48 (d, 1H, Ar—H, J = 1.8 Hz), 7.42 (d, 1H, Ar—H, J = 2.1 Hz), 7.38 (t, 1H, Ar—H, J = 2.0 & 2.1 Hz), 7.35 (d, 1H, Ar—H, J = 1.8 Hz), 4.89 (s, 2H, Ar—CH$_2$), 2.37 (s, 3H, COCH$_3$) | 580.40 |
| 9 | 6-((2,6-dichlorobenzyl)sulfonyl)-2H-benzo[b][1,4]thiazin-3(4H)-one (Example 4) | 4-acetoxybenzaldehyde | 228-230 | NMR not recorded | 535.98 |
| 10 | 6-((2,6-dichlorobenzyl)sulfonyl)-2H-benzo[b][1,4]thiazin-3(4H)-one (Example 4) | Benzaldehyde | 210-211 | (DMSO-d$_6$; 300 MHz): 11.28 (brs, 1H, NH), 7.86 (s, 1H, =CH), 7.69 (d, 2H, Ar—H, J = 7.8 Hz), 7.61 (d, 1H, Ar—H, J = 8.4 Hz), 7.54-7.52 (m, 3H, Ar—H), 7.47 (s, 1H, Ar—H), 7.45 (s, 1H, Ar—H), 7.43 (d, 2H, Ar—H, J = 7.8 Hz), 7.36 (d, 1H, Ar—H, J = 8.4 Hz), 4.88 (s, 2H, Ar—CH$_2$) | 477.08 |
| 11 | 6-((2,6-dichlorobenzyl)sulfonyl)-2H-benzo[b][1,4]thiazin-3(4H)-one (Example 4) | 4-methoxy-3-nitrobenzaldehyde | >320 | (DMSO-d$_6$; 300 MHz): 11.31 (brs, 1H, NH), 8.24 (s, 1H, Ar—H), 8.00 (d, 1H, Ar—H, J = 8.4 Hz), 7.84 (s, 1H, =CH), 7.63 (d, 1H, Ar—H, J = 8.4 Hz), 7.54-7.51 (m, 3H, Ar—H), 7.47 (s, 1H, Ar—H), 7.43 (d, 1H, Ar—H, J = 7.2 Hz), 7.37 (d, 1H, Ar—H, J = 8.4 Hz), 4.89 (s, 2H, Ar—CH$_2$), 4.00 (s, 3H, OCH$_3$) | 552.43 |
| 12 | 6-((2,6-dichlorobenzyl)sulfonyl)-2H-benzo[b][1,4]thiazin-3(4H)-one (Example 4) | 3-amino-4-methoxybenzaldehyde | 248-250 | NMR not recorded | 522.01 |

TABLE 4-continued

| Cpd. # | Starting Benzothiazinone | Starting Aldehye | m.p. (° C.) | ¹H NMR (δ ppm) | LC-MS (M + 1) |
|---|---|---|---|---|---|
| 13 | 6-((2,6-dichlorobenzyl)sulfonyl)-2H-benzo[b][1,4]thiazin-3(4H)-one (Example 4) | 4-(4-methylpiperazin-1-yl)benzaldehyde | 140-142 | (DMSO-d$_6$; 300 MHz): 9.89 (brs, 1H, NH), 8.25 (s, 1H, Ar—H), 7.90 (d, 1H, Ar—H, J = 7.8 Hz), 7.76 (s, 1H, =CH), 7.45 (d, 2H, Ar—H, J = 8.4 Hz), 7.39 (d, 1H, Ar—H, J = 7.8 Hz), 7.34 (s, 1H, Ar—H), 7.27 (d, 1H, Ar—H, J = 8.4 Hz), 7.09 (d, 1H, Ar—H, J = 7.8 Hz), 6.94 (d, 2H, Ar—H, J = 7.2 Hz), 4.83 (s, 2H, Ar—CH$_2$), 3.55-3.53 (m, 4H, Pip-H), 2.42-2.39 (m, 4H, Pip-H), 2.19 (s, 3H, N—CH$_3$) | 575.08 |
| 14 | 6-((2,6-dichlorobenzyl)sulfonyl)-2H-benzo[b][1,4]thiazin-3(4H)-one (Example 4) | 4-nitrobenzaldehyde | >320 | NMR not recorded | 522.28 |
| 15 | 6-((2,6-dichlorobenzyl)sulfonyl)-2H-benzo[b][1,4]thiazin-3(4H)-one (Example 4) | 4-aminobenzaldehyde | >320 | NMR not recorded. | 492.98 |
| 16 | 6-((2,6-dichlorobenzyl)sulfonyl)-2H-benzo[b][1,4]thiazin-3(4H)-one (Example 4) | 4-fluorobenzaldehyde | 308 | NMR not recorded | 495.97 |
| 17 | 6-((2,6-dichlorobenzyl)sulfonyl)-2H-benzo[b][1,4]thiazin-3(4H)-one (Example 4) | 4-chlorobenzaldehyde | >320 | NMR not recorded | 511.94 |
| 18 | 6-((2,6-dichlorobenzyl)sulfonyl)-2H-benzo[b][1,4]thiazin-3(4H)-one (Example 4) | 4-bromobenzaldehyde | >310 | NMR not recorded | 556.89 |
| 19 | 6-((2,6-dichlorobenzyl)sulfonyl)-2H-benzo[b][1,4]thiazin-3(4H)-one (Example 4) | 4-methoxybenzaldehyde | | NMR not recorded | 507.33 |
| 20 | 6-((2,6-dichlorobenzyl)sulfonyl)-2H-benzo[b][1,4]thiazin-3(4H)-one (Example 4) | 4-methylbenzaldehyde | | NMR not recorded | 491.52 |
| 21 | 6-((2,6-dichlorobenzyl)sulfonyl)-2H-benzo[b][1,4]thiazin-3(4H)-one (Example 4) | 2,4,6-trimethoxybenzaldehyde | | NMR not recorded | 567.13 |
| 22 | 6-((2,6-dichlorobenzyl)sulfonyl)-2H-benzo[b][1,4]thiazin-3(4H)-one (Example 4) | 2,4-dichlorobenzaldehyde | >310 | NMR not recorded | 546.30 |
| 23 | (number intentionally skipped) | — | | — | — |
| 24 | 6-((2,6-dichlorobenzyl)sulfonyl)-2H-benzo[b][1,4]thiazin-3(4H)-one (Example 4) | methyl (4-formylphenyl)glycinate | | NMR not recorded | 564.36 |

TABLE 4-continued

| Cpd. # | Starting Benzothiazinone | Starting Aldehyde | m.p. (° C.) | ¹H NMR (δ ppm) | LC-MS (M + 1) |
|---|---|---|---|---|---|
| 25 | 6-((2,6-dichlorobenzyl)sulfonyl)-2H-benzo[b][1,4]thiazin-3(4H)-one (Example 4) | *(structure: 4-((carboxymethyl)amino)benzaldehyde)* | | NMR not recorded | 550.80 |
| 26 | 6-((2,6-dichlorobenzyl)sulfonyl)-2H-benzo[b][1,4]thiazin-3(4H)-one (Example 4) | *(structure: 1-acetyl-1H-indole-3-carbaldehyde)* | >300 | NMR not recorded | 558.03 |
| 27 | 6-((2,6-dichlorobenzyl)sulfonyl)-2H-benzo[b][1,4]thiazin-3(4H)-one (Example 4) | *(structure: 1H-pyrrole-3-carbaldehyde)* | | NMR not recorded | 466.24 |
| 28 | 6-((2,6-dichlorobenzyl)sulfonyl)-2H-benzo[b][1,4]thiazin-3(4H)-one (Example 4) | 4-hydroxy-2,6-dimethoxybenzaldehyde | | NMR not recorded | 553.85 |
| 29 | 6-((2,6-dichlorobenzyl)sulfonyl)-2H-benzo[b][1,4]thiazin-3(4H)-one (Example 4) | 4-chloro-3-nitrobenzaldehyde | >310 | NMR not recorded | 556.78 |
| 30 | 6-((2,6-dichlorobenzyl)sulfonyl)-2H-benzo[b][1,4]thiazin-3(4H)-one (Example 4) | 2,4-difluorobenzaldehyde | 310-312 | NMR not recorded | 513.69 |
| 31 | 6-((2,6-dichlorobenzyl)sulfonyl)-2H-benzo[b][1,4]thiazin-3(4H)-one (Example 4) | 2,4,6-trifluorobenzaldehyde | 254-256 | NMR not recorded | 531.53 |
| 32 | 6-((2,6-dichlorobenzyl)sulfonyl)-2H-benzo[b][1,4]thiazin-3(4H)-one (Example 4) | *(structure: methyl 4-formylbenzoate)* | >300 | NMR not recorded | 535.98 |
| 33 | 6-((2,6-dichlorobenzyl)sulfonyl)-2H-benzo[b][1,4]thiazin-3(4H)-one (Example 4) | *(structure: thiophene-2-carbaldehyde)* | 310-312 | NMR not recorded | 483.93 |
| 34 | 6-((2,6-dichlorobenzyl)sulfonyl)-2H-benzo[b][1,4]thiazin-3(4H)-one (Example 4) | *(structure: 1H-indole-3-carbaldehyde)* | | NMR not recorded | 515.43 |

TABLE 4-continued

| Cpd. # | Starting Benzothiazinone | Starting Aldehyde | m.p. (° C.) | ¹H NMR (δ ppm) | LC-MS (M + 1) |
|---|---|---|---|---|---|
| 35 | 6-((2,6-dichlorobenzyl)sulfonyl)-2H-benzo[b][1,4]thiazin-3(4H)-one (Example 4) | | 260-264 | NMR not recorded | 580.98 |
| 36 | 6-((2,6-dichlorobenzyl)sulfonyl)-2H-benzo[b][1,4]thiazin-3(4H)-one (Example 4) | | >300 | NMR not recorded | 525.96 |
| 37 | 6-((2,6-dichlorobenzyl)sulfonyl)-2H-benzo[b][1,4]thiazin-3(4H)-one (Example 4) | | >300 | NMR not recorded | 564.02 |
| 38 | 6-((2,6-dichlorobenzyl)sulfonyl)-2H-benzo[b][1,4]thiazin-3(4H)-one (Example 4) | | 292-294 | NMR not recorded | 692.44 |
| 39 | 6-((2,6-dichlorobenzyl)sulfonyl)-2H-benzo[b][1,4]thiazin-3(4H)-one (Example 4) | | 250-258 | NMR not recorded | 545.23 |
| 40 | | | 238-240 | (CDCl₃; 600 MHz): 8.50 (s, 1H, Ar—H), 7.94 (s, 2H, =CH & Ar—H), 7.53 (d, 1H, Ar—H, J = 8.4 Hz), 7.38 (d, 1H, Ar—H, J = 7.4 Hz), 6.93 (s, 1H, Ar—H), 6.90 (d, 1H, Ar—H, J = 7.3 Hz), 3.84 (s, 3H, OCH₃), 2.67 (s, 3H, COCH₃), 2.45 (s, 3H, COCH₃) | 429.13 |

TABLE 4-continued

| Cpd. # | Starting Benzothiazinone | Starting Aldehye | m.p. (° C.) | $^1$H NMR (δ ppm) | LC-MS (M + 1) |
|---|---|---|---|---|---|
| 41 | 6-((2,6-dichlorobenzyl)sulfonyl)-2H-benzo[b][1,4]thiazin-3(4H)-one (Example 4) | 3-nitro-4-(benzyloxy)benzaldehyde | 306-308 | (DMSO-d$_6$; 600 MHz): 11.31 (brs, 1H, NH), 8.27 (s, 1H, Ar—H), 8.00 (d, 1H, Ar—H, J = 8.8 Hz), 7.86 (s, 2H, =CH), 7.65 (d, 1H, Ar—H, J = 8.3 Hz), 7.62 (d, 1H, Ar—H, J = 8.8 Hz), 7.55 (d, 2H, Ar—H, J = 8.0 Hz), 7.51-7.50 (m, 3H, Ar—H), 7.46-7.44 (m, 3H, Ar—H), 7.39 (d, 2H, Ar—H, J = 7.8 Hz), 5.43 (s, 2H, Ar—CH$_2$), 4.91 (s, 2H, Ar—CH$_2$) | 628.61 |
| 42 | 6-((2,6-dichlorobenzyl)sulfonyl)-2H-benzo[b][1,4]thiazin-3(4H)-one (Example 4) | 4-hydroxy-3-nitrobenzaldehyde | 312-314 | (DMSO-d$_6$; 600 MHz): 11.63 (brs, 1H, OH), 11.27 (brs, 1H, NH), 8.26 (s, 1H, Ar—H), 7.90 (d, 1H, Ar—H, J = 8.3 Hz), 7.82 (s, 1H, =CH), 7.64 (d, 1H, Ar—H, J = 8.2 Hz), 7.55 (d, 2H, Ar—H, J = 7.9 Hz), 7.49 (s, 1H, Ar—H), 7.45 (t, 1H, Ar—H, J = 7.9 & 8.0 Hz), 7.38 (d, 1H, Ar—H, J = 8.0 Hz), 7.28 (d, 1H, Ar—H, J = 8.5 Hz), 4.90 (s, 2H, Ar—CH$_2$) | 538.05 |
| 43 | 7-fluoro-2H-benzo[b][1,4]thiazin-3(4H)-one | 3-nitro-4-(benzyloxy)benzaldehyde | 256-258 | NMR not recorded | 423.45 |
| 44 | 7-fluoro-2H-benzo[b][1,4]thiazin-3(4H)-one | 4-hydroxy-3-nitrobenzaldehyde | 262-264 | (DMSO-d$_6$; 600 MHz): 11.63 (brs, 1H, OH), 11.13 (brs, 1H, NH), 8.24 (d, 1H, Ar—H, J = 2.0 Hz), 7.89-7.87 (dd, 1H, Ar—H, J = 2.2 & 8.7 Hz), 7.76 (s, 1H, =CH), 7.42-7.40 (dd, 1H, Ar—H, J = 5.8 & 8.5 Hz), 7.27 (d, 1H, Ar—H, J = 8.8 Hz), 6.93-6.89 (m, 2H, Ar—H) | 333.23 |

Example 7

Leukemia and Prostate Cancer Cell Cytotoxicity Assays

The effect of the compounds of the invention on tumor cells was determined by the assay described by Latham et al., *Oncogene* 12:827-837 (1996). Tumor cells K562 (chronic myelogenous leukemia; leukemia cell line +ve for Bcr-Abl) or DU145 (prostate cancer) were plated in 12-well dishes at a cell density of 2.5×10$^4$ cells well. The plated cells were treated 24 hours later with a compound of the invention dissolved in DMSO at multiple concentrations ranging from 0.01 μM to 100 μM. The plates were examined 96 hours later under an inverted microscope, Olympus CK-2 using a 10× objective, and compound activity was noted by physical observation. When necessary, the total number of viable cells was determined by trypsinizing the wells and counting the number of viable cells, as determined by trypan blue exclusion, using a hemacytometer. The results of these assays are provided below in Table 5. Where "Lower" and "Upper" value are provided in Table 5, the IC$_{50}$ was determined to be within that range. When only a "Lower" value is provided and no "Upper" value is listed, the IC$_{50}$ was that value, or less than or greater than that value, as set forth in the Table.

TABLE 5

| | K562 IC$_{50}$ (μm) | | DU145 IC$_{50}$ (μm) | |
|---|---|---|---|---|
| Cpd. # | Lower (μm) | Upper (μm) | Lower (μm) | Upper (μm) |
| 1 | 10 | 25 | 1 | 10 |
| 2 | 1 | 10 | 1 | 10 |
| 3 | 1 | 10 | 10 | 25 |
| 4 | 1 | 10 | 1 | 10 |
| 5 | 50 | 100 | >100 | N/A |
| 6 | 1 | 10 | N/A | 1.0 |

TABLE 5-continued

| Cpd. # | K562 IC$_{50}$ (μm) | | DU145 IC$_{50}$ (μm) | |
|---|---|---|---|---|
| | Lower (μm) | Upper (μm) | Lower (μm) | Upper (μm) |
| 7 | 1 | 10 | 1 | 10 |
| 8 | 0.075 | N/A | 0.1 | N/A |
| 9 | <1 | N/A | <1 | N/A |
| 10 | 1 | 10 | <1 | N/A |
| 11 | 0.25 | 0.5 | 0.25 | 0.5 |
| 12 | 0.1 | 0.25 | 0.25 | 0.5 |
| 13 | 0.5 | 1 | 1 | 10 |
| 14 | 1 | 10 | 1 | 10 |
| 15 | 0.03 | N/A | 0.04 | N/A |
| 16 | 1 | 10 | 1 | 10 |
| 17 | 1 | 10 | 1 | 10 |
| 18 | 1 | 10 | 1 | 10 |
| 22 | 1 | 10 | 1 | 10 |
| 29 | 1 | 10 | 0.5 | 1.0 |
| 30 | 1 | 10 | 1 | 10 |
| 31 | 1 | 10 | 1 | 10 |
| 32 | 1 | 10 | 0.5 | 1.0 |
| 33 | 0.5 | 1.0 | 0.5 | 1.0 |
| 26 | 0.5 | 1.0 | 0.5 | 1.0 |
| 35 | 1 | 10 | >10 | N/A |
| 36 | >2.5 | N/A | 2 | N/A |
| 37 | 1 | 10 | 1 | 10 |
| 38 | 0.1 | N/A | 0.09 | N/A |
| 39 | 1 | 10 | 1 | 10 |
| 40 | 1.5 | N/A | 2 | N/A |
| 41 | 0.75 | N/A | 1.5 | N/A |
| 42 | 0.1 | N/A | 0.15 | N/A |
| 43 | >10 | N/A | >10 | N/A |
| 44 | 0.25 | N/A | 0.75 | N/A |

Example 8

Cancer Cell Cytotoxicity Assays: (Z)-6-((2,6-Dichlo-robenzyl)sulfonyl)-2-(4-hydroxy-3-nitroben-zylidene)-2H-benzo[b][1,4]thiazin-3(4H)-one The cytotoxicity of Compound 42, (Z)-6-((2,6-dichlorobenzyl)sulfonyl)-2-(4-hydroxy-3-nitrobenzylidene)-2H-benzo[b][1,4]thiazin-3(4H)-one, was determined according the assay method of Example 7 on the prostate (androgen dependent or independent), breast and pancreatic cancer cell lines listed in Table 6A, below, and the additional cell lines listed in Table 6B, below. The human mesenchymal stem cell line HMSC.hTERT and normal human fibroblast cell line HFL was included in the test. The results indicate that while Compound 42 was toxic to the cancer cell lines, it did not cause cell death in the normal human stem cell line, or in the normal human fibroblast cell line, demonstrating the selectivity of the compound for cancer cells.

TABLE 6A

| CELL LINE | TUMOR TYPE | GI$_{50}$(μM) |
|---|---|---|
| DU-145 | Prostate Cancer (Androgen Independent) | 0.16 |
| LnCap | Prostate Cancer (Androgen Dependent) | 0.25 |
| MDA.MB-231 | Breast Cancer | 0.12 |
| MDA.MB-468 | Breast Cancer | 0.2 |
| BT-474 | Breast Cancer | 0.2 |
| MCF-7 | Breast Cancer | 1.0 |
| MiaPaca 2 | Pancreatic Cancer | 0.09 |
| HMSC.hTERT | Human Mesenchymal Stem cells | >10 |

TABLE 6B

| CELL LINE | TMUOR TYPE | GI$_{50}$(μM) |
|---|---|---|
| PC3 | Prostate Cancer | 0.16 |
| 22Rv1 | Prostate Cancer | 0.50 |
| VCAP | Prostate Cancer | 0.18 |
| RPWE-1 | Prostate Cancer | 0.10 |
| MCF10A | Normal Breast Cancer | 2.50 |
| A549 | Non-small cell lung cancer | 0.16 |
| H23 | Non-small cell lung cancer | 0.065 |
| HCT-116 | Colon cancer | 0.15 |
| K562 | Chronic myelogenous leukemia | 0.16 |
| Z138C | Mantle cell lymphoma | 0.07 |
| U266B1 | Multiple Myeloma | 0.10 |
| GRANTA | Mantle cell lymphoma | 0.08 |
| HFL | Normal Fibroblast | >10 |

Example 9

Casein Kinase 2α Inhibition by (Z)-6-((2,6-Dichlo-robenzyl)sulfonyl)-2-(4-hydroxy-3-nitroben-zylidene)-2H-benzo[b][1,4]thiazin-3(4H)-one The ability of Compound 42 to inhibit the activity of casein kinase 2 (CK2) was determined as follows using the catalytic CK2 subunits CK2α and CK2α2. Two and one half nanograms of CK2α (human full length protein; Invitrogen PV3248), 2.5 ng of a CK2α form containing amino acids 3-339) or 10 ng of CK2α2 (human full length protein; Invitrogen PV3624) was diluted into kinase buffer (20 mM Tris pH 7.5, 10 mM MgCl$_2$, 0.01% NP-40, 1 mM EGTA, 2 mM DTT) and incubated with varying concentrations of Compound 42 at room temperature for 30 minutes. Kinase reactions were initiated by the addition of 1 μg of CK2 substrate α-synuclein or 40 μM CK2 synthetic peptide substrate (AnaSpec, San Jose, Calif.), 20 μM cold ATP, and 20 μCi γ-$^{32}$P-ATP. The reactions were incubated at 30° C. for 20 minutes, terminated by the addition of 2× Laemmle sample buffer, boiled for 2 minutes, resolved by 12% acrylamide SDS-PAGE, and subjected to autoradiography. The IC$_{50}$ for Compound 42 inhibition of CK2α was 361.9 nM. The IC$_{50}$ for Compound 42 inhibition of CK2α2 was 83.1 nM.

Example 10

CDK9 Inhibition by (Z)-6-((2,6-Dichlorobenzyl) sulfonyl)-2-(4-hydroxy-3-nitrobenzylidene)-2H-benzo[b][1,4]thiazin-3(4H)-one The ability of Compound 42 to inhibit the activity of the kinase CDK9 was determined as follows. Twenty-five nanograms of CDK9 (human full length protein; Invitrogen PV4335) was diluted into kinase buffer (20 mM Tris pH 7.5, 10 mM MgCl2, 0.01% NP-40, 1 mM EGTA, 2 mM DTT) and incubated with varying concentrations of Compound 42 at room temperature for 30 minutes. The kinase reactions were initiated by the addition of 20 μM of CDK9/Cyclin K specific synthetic peptide substrate (PDKtide, P10-58, SignalChem), 20 μM cold ATP, and 20 μCi γ-32P-ATP. The reactions were incubated at 30° C. for 20 minutes and terminated by the addition of 0.5M o-Phosphoric acid. 10 μl of the reaction mixture was spotted on a P-30 Filtermat (PerkinElmer) and developed using autoradiography or phosphorimaging. The IC$_{50}$ for Compound 42 inhibition of CDK9 was determined as 93.68 nM.

Example 11

PIM1 Inhibition by (Z)-6-((2,6-Dichlorobenzyl)sulfonyl)-2-(4-hydroxy-3-nitrobenzylidene)-2H-benzo[b][1,4]thiazin-3(4H)-one The ability of Compound 42 to inhibit the activity of the kinase proto-ocogene pim-was determined as follows. Ten nanograms of PIM1 (human full length protein; Invitrogen PV3503) was diluted into kinase buffer (20 mM Tris pH 7.5, 10 mM MgCl$_2$, 0.01% NP-40, 1 mM EGTA, 2 mM DTT) and incubated with varying concentrations of Compound 42 at room temperature for 30 minutes. The kinase reactions were initiated by the addition of 20 µM of PIM1 specific synthetic peptide substrate (K9 Peptide; p70S6 Kinase Substrate; AnaSpec, San Jose, Calif.), 20 µM cold ATP, and 20 µCi γ-$^{32}$P-ATP. The reactions were incubated at 30° C. for 20 minutes and terminated by the addition of 0.5M o-Phosphoric acid. 10 µl of the reaction mixture was spotted on a P-30 Filtermat (PerkinElmer) and developed using autoradiography or phosphorimaging. The IC$_{50}$ for Compound 42 inhibition of PIM1 was determined as 226.1 nM.

All references cited herein are incorporated by reference. The present invention may be embodied in other specific forms without departing from the spirit or essential attributes thereof and, accordingly, reference should be made to the appended claims, rather than to the foregoing specification, as indicating the scope of the invention.

What is claimed is:

1. A compound of Formula I or a salt thereof:

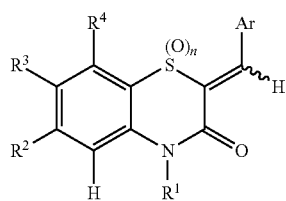

Formula I wherein
n is 0, 1, or 2;
R$^1$ is selected from the group consisting of —H, —(C$_1$-C$_6$)alkyl, —(C$_2$-C$_6$)alkenyl, —(C$_2$-C$_6$)alkynyl, optionally substituted aryl, optionally substituted heteroaryl, optionally substituted aryl-(C$_1$-C$_6$)alkyl, optionally substituted heteroaryl—(C$_1$-C$_6$)alkyl, —C(=O)(C$_1$-C$_6$)alkyl, —C(=O)(C$_2$-C$_6$)alkenyl, —C(=O)-optionally substituted aryl, —C(=O)(CH$_2$)$_m$-optionally substituted aryl, and —C(=O)(CH$_2$)$_p$-optionally substituted heteroaryl;
R$^2$, R$^3$, and R$^4$ are independently selected from the group consisting of —H, halogen, —CN, —OH, —OR$^{13}$, —(C$_1$-C$_6$)alkoxy, —NO$_2$, —(C$_1$-C$_6$)alkyl, —(C$_1$-C$_6$)perfluoroalkyl, —(C$_1$-C$_6$)perfluoroalkoxy, —C(=O)R$^{15}$, —C(=O)OR$^{15}$, —OC(=O)R$^{12}$, —OC(=O)OR$^{12}$, —C(=O)NR$^{17}$R$^{18}$, —SH, —S(C$_1$-C$_6$)alkyl, —SR$^{13}$, —S(=O)R$^{13}$, —S(=O)$_2$R$^{13}$, —OS(=O)$_2$R$^{13}$, —S(=O)$_q$R$^{15}$, —OS(=O)$_q$R$^{15}$, —S(=O)$_2$NR$^{17}$R$^{18}$, —S(=O)NR$^{17}$R$^{18}$, optionally substituted aryl, optionally substituted aryl—(C$_1$-C$_6$)alkyl, optionally substituted heteroaryl, optionally substituted heteroaryl-(C$_1$-C$_6$)alkyl, optionally substituted (C$_2$-C$_9$)heterocyclyl-(C$_1$-C$_6$)alkyl, —NH(CH$_2$)$_m$C(=O)OR$^{14}$, —C(=NR$^{14}$)NR$^{14}$$_2$, —C(=N—OR$^{14}$)NR$^{14}$$_2$, —P(=O)(OR$^{14}$)$_2$, and —OP(=O)(OR$^{14}$)$_2$;
Ar is optionally substituted (C$_{10}$-C$_{14}$)aryl, or

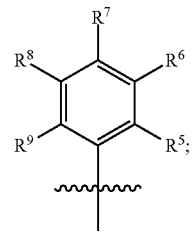

wherein
R$^5$, R$^6$, R$^7$, R$^8$, and R$^9$ are independently selected from the group consisting of —H, —OH, —OR$^{13}$, —NO$_2$, halogen, —CN, —NR$^{10}$R$^{11}$, —(CH$_2$)$_m$NR$^{10}$R$^{11}$, —(C$_1$-C$_6$)alkyl, —(CH$_2$)$_m$O(C$_1$-C$_6$)alkyl, —(C$_1$-C$_6$)alkoxy, —(C$_1$-C$_6$)perfluoroalkyl, —(C$_1$-C$_6$)perfluoroalkoxy, —SH, —S(C$_1$-C$_6$)alkyl, —SR$^{13}$, —S(=O)R$^{15}$, —S(=O)$_2$R$^{15}$, —C(=O)R$^{15}$, —C(=O)OR$^{15}$, —C(=O)NR$^{17}$R$^{18}$, —OC(=O)R$^{16}$, —OC(=O)OR$^{12}$, —OC(=O)NR$^{17}$R$^{18}$ heterocyclyl, optionally substituted heteroaryl, —NH(CH$_2$)$_m$C(=O)OR$^{14}$, —OS(=O)$_2$R$^{16}$, —C(=NR$^{14}$)NR$^{14}$$_2$, —C(=N—OR$^{14}$)NR$^{14}$$_2$, —P(=O)(OR$^{14}$)$_2$, and —OP(=O)(OR$^{14}$)$_2$;
each R$^{10}$ and R$^{11}$ is independently selected from the group consisting of —H, —(C$_1$-C$_6$)alkyl, —(C$_1$-C$_6$)alkoxy, —C(=O)R$^{12}$, —C(=O)NR$^{17}$R$^{18}$, —C(=O)OR$^{12}$, —C(=NR$^{14}$)NR$^{17}$R$^{18}$, R$^{13}$, optionally substituted aryl, optionally substituted heteroaryl, and —C(=NR$^{14}$)R$^{15}$; or R$^{10}$ and R$^{11}$, together with the nitrogen to which they are bound, form an optionally substituted (C$_2$-C$_5$)heterocycle;
each R$^{12}$ is independently selected from the group consisting of —(C$_1$-C$_6$)alkyl, and optionally substituted aryl;
each R$^{13}$ is independently selected from the group consisting of optionally substituted aryl and —(CH$_2$)$_m$R$^{16}$;
each R$^{14}$ is independently selected from the group consisting of —H and —(C$_1$-C$_6$)alkyl; or two occurrences of R$^{14}$ bound to the same nitrogen form a (C$_2$-C$_6$)heterocycle, together with the nitrogen atom to which they are bound;
each R$^{15}$ is independently selected from the group consisting of —H, —(C$_1$-C$_6$)alkyl, optionally substituted aryl, and NR$^{14}$$_2$;
each R$^{16}$ is independently selected from the group consisting of —(C$_1$-C$_6$)alkyl, —NR$^{14}$$_2$, and Ar$^1$;
each R$^{17}$ and R$^{18}$ is independently selected from the group consisting of —H, —(C$_1$-C$_6$)alkyl, —(C$_1$-C$_6$)alkoxy, R$^{13}$, optionally substituted aryl, and optionally substituted heteroaryl; or R$^{17}$ and R$^{18}$, together with the nitrogen to which they are bound, form an optionally substituted (C$_2$-C$_5$)heterocycle;
m is independently at each occurrence 1, 2, 3, 4, or 5;
p is independently at each occurrence 0, 1, 2, or 3;
q is independently at each occurrence 0, 1, or 2;
each optionally substituted aryl, optionally substituted (C$_{10}$-C$_{14}$)aryl, optionally substituted heteroaryl, optionally substituted aryl-(C$_1$-C$_6$)alkyl, optionally substituted heteroaryl -(C$_1$-C$_6$)alkyl, optionally substituted (C$_2$-C$_9$)heterocyclyl, optionally substituted (C$_2$-C$_9$)heterocyclyl-(C$_1$-C$_6$)alkyl, and optionally substituted (C$_2$-C$_5$)heterocycle is optionally substituted with one or more substituents independently selected from the group consisting of halogen, —CN, —NR$^{14}_2$, —(CH$_2$)$_m$NR$^{14}_2$, —O(CH$_2$)$_m$NR$^{14}_2$, —NR$^{14}$C(=O)(C$_1$-C$_6$)alkyl, —NR$^{14}$C(=O)O(C$_1$-C$_6$)alkyl, —NR$^{14}$C(=O)NR$^{14}_2$, —NR$^{14}$C(=NR$^{14}$)NR$^{14}_2$, —NH(CH$_2$)$_m$C(=O)OR$^{14}$, —OH, —NO$_2$, —(C$_1$-C$_6$)alkyl, —(CH$_2$)$_m$O(C$_1$-C$_6$)alkyl, —(C$_1$-C$_6$)alkoxy, —(C$_2$-C$_6$)alkenyl, —(C$_2$-C$_6$)alkynyl, —SR$^{14}$, —S(=O)R$^{15}$, —S(=O)$_2$R$^{15}$, —NR$^{14}$S(=O)$_2$R$^{15}$, —(C$_1$-C$_6$)perfluoroalkyl, —(C$_1$-C$_6$)perfluoroalkoxy, —C(=O)R$^{14}$, —C(=O)OR$^{14}$, —C(=O)NR$^{14}_2$, —OC(=O)R$^{14}$, —OC(=O)NR$^{14}_2$, —OC(=O)O(C$_1$-C$_6$)alkyl, —P(=O)(OR$^{14}$)$_2$, —OP(=O)(OR$^{14}$)$_2$, heterocyclyl, and heteroaryl;

Ar$^1$ is a radical according to Formula II:

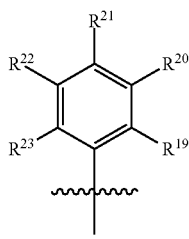

Formula II wherein R$^{19}$, R$^{20}$, R$^{21}$, R$^{22}$, and R$^{23}$ are independently selected from the group consisting of —H, —OH, —NO$_2$, halogen, —CN, —NR$^{10}$R$^{11}$, —(CH$_2$)$_m$NR$^{10}$R$^{11}$, —O(CH$_2$)$_m$NR$^{10}$R$^{11}$, —(C$_1$-C$_6$)alkyl, —(CH$_2$)$_m$O(C$_1$-C$_6$)alkyl, —(C$_1$-C$_6$)alkoxy, —(C$_1$-C$_6$)perfluoroalkyl, —(C$_1$-C$_6$)perfluoroalkoxy, —SH, —SR$^{12}$, —S(=O)R$^{15}$, —S(=O)$_2$R$^{15}$, —C(=O)R$^{15}$, —C(=O)OR$^{15}$, —C(=O)NR$^{17}$R$^{18}$, —OC(=O)R$^{16}$, —OC(=O)OR$^{12}$, —OC(=O)NR$^{17}$R$^{18}$, heterocyclyl, optionally substituted heteroaryl, —NH(CH$_2$)$_m$C(=O)OR$^{14}$, —OS(=O)$_2$R$^{16}$, —C(=NR$^{14}$)NR$^{14}_2$, —C(=N—OR$^{14}$)NR$^{14}_2$, —P(=O)(OR$^{14}$)$_2$, and —OP(=O)(OR$^{14}$)$_2$;

provided that:
i) at least one of R$^2$, R$^3$, or R$^4$ is other than hydrogen; and
ii) when none of R$^2$, R$^3$, and R$^4$ are —OR$^{13}$, —SR$^{13}$, —S(=O)R$^{13}$, or —S(=O)$_2$R$^{13}$, and Ar is

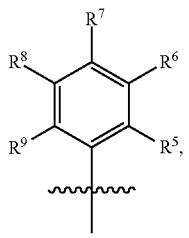

then at least one of R$^6$ and R$^8$ is —NO$_2$ and at least R$^7$ is other than hydrogen or halogen.

2. A compound according to claim 1, or a salt thereof, wherein n is 0.

3. A compound according to claim 2, or a salt thereof, wherein Ar is

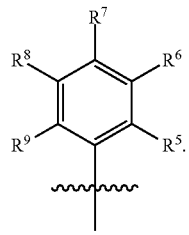

4. A compound according to claim 3, or a salt thereof, wherein at least one of R$^2$, R$^3$, or R$^4$ is —OR$^{13}$, —SR$^{13}$, —S(=O)R$^{13}$, or —S(=O)$_2$R$^{13}$.

5. A compound according to claim 4, or a salt thereof, wherein at least one of R$^2$, R$^3$, or R$^4$ is —S(=O)$_2$R$^{13}$.

6. A compound according to claim 5, or a salt thereof, wherein R$^{13}$ is —(CH$_2$)$_m$R$^{16}$.

7. A compound according to claim 5, or a salt thereof, wherein R$^2$ is —S(=O)$_2$R$^{13}$ and R$^{13}$ is —(CH$_2$)$_m$R$^{16}$.

8. A compound according to claim 7, or a salt thereof, wherein R$^{16}$ is Ar$^1$.

9. A compound according to claim 8, or a salt thereof, wherein Ar$^1$ is 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-difluorophenyl, 2,4-difluorophenyl, 2,5-difluorophenyl, 2,6-difluorophenyl, 3,4-difluorophenyl, 3,5-difluorophenyl, 2,3-diiodophenyl, 2,4-diiodophenyl, 2,5-diiodophenyl, 2,6-diiodophenyl, 3,4-diiodophenyl, 3,5-diiodophenyl, 2-chloro-3-bromophenyl, 2-chloro-4-bromophenyl, 2-chloro-5-bromophenyl, 2-chloro-6-bromophenyl, 3-chloro-4-bromophenyl, 3-chloro-5-bromophenyl, 4-chloro-5-bromophenyl, 2-bromo-3-chlorophenyl, 2-bromo-4-chlorophenyl, 2-bromo-5-chlorophenyl, 3-bromo-4-chlorophenyl, 2-chloro-3-fluorophenyl, 2-chloro-4-fluorophenyl, 2-chloro-5-fluorophenyl, 2-chloro-6-fluorophenyl, 3-chloro-4-fluorophenyl, 3-chloro-5-fluorophenyl, 4-chloro-5-fluorophenyl, 2-fluoro-3-chlorophenyl, 2-fluoro-4-chlorophenyl, 2-fluoro-5-chlorophenyl, 3-fluoro-4-chlorophenyl, 2-chloro-3-iodophenyl, 2-chloro-4-iodophenyl, 2-chloro-5-iodophenyl, 2-chloro-6-iodophenyl, 3-chloro-4-iodophenyl, 3-chloro-5-iodophenyl, 4-chloro-5-iodophenyl, 2-iodo-3-chlorophenyl, 2-iodo-4-chlorophenyl, 2-iodo-5-chlorophenyl, 3-iodo-4-chlorophenyl, 2-bromo-3-fluorophenyl, 2-bromo-4-fluorophenyl, 2-bromo-5-fluorophenyl, 2-bromo-6-fluorophenyl, 3-bromo-4-fluorophenyl, 3-bromo-5-fluorophenyl, 4-bromo-5-fluorophenyl, 2-fluoro-3-bromophenyl, 2-fluoro-4-bromophenyl, 2-fluoro-5-bromophenyl, 3-fluoro-4-bromophenyl, 2-bromo-3-iodophenyl, 2-bromo-4-iodophenyl, 2-bromo-5-iodophenyl, 2-bromo-6-iodophenyl, 3-bromo-4-iodophenyl, 3-bromo-5-iodophenyl, 4-bromo-5-iodophenyl, 2-iodo-3-bromophenyl, 2-iodo-4-bromophenyl, 2-iodo-5-bromophenyl, 3-iodo-4-bromophenyl, 2-fluoro-3-iodophenyl, 2-fluoro-4-iodophenyl, 2-fluoro-5-iodophenyl, 2-fluoro-6-iodophenyl, 3-fluoro-4-iodophenyl, 3-fluoro-5-iodophenyl, 4-fluoro-5-iodophenyl, 2-iodo-3-fluorophenyl, 2-iodo-4-fluorophenyl, 2-iodo-5-fluorophenyl, or 3-iodo-4-fluorophenyl.

10. A compound according to claim 9, or a salt thereof, wherein Ar$^1$ is 2,6-dichlorophenyl.

11. A compound according to claim 10, or a salt thereof, wherein Ar is

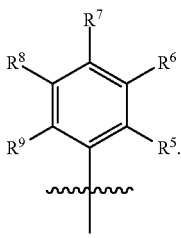

12. A compound according to claim 11, or a salt thereof, wherein said compound is selected from the group consisting of (Z)-4-((6-((2,6-dichlorobenzyl)sulfonyl)-3-oxo-3,4-dihydro-2H-benzo[b][1,4]thiazin-2-ylidene)methyl)-2-nitrophenyl acetate; (Z)-4-((6-((2,6-dichlorobenzyl)sulfonyl)-3-oxo-3,4-dihydro-2H-benzo[b][1,4]thiazin-2-ylidene)methyl) phenyl acetate; (Z)-2-benzylidene-6-((2,6-dichlorobenzyl)sulfonyl)-2H-benzo[b][1,4]thiazin-3(4H)-one; (Z)-6-((2,6-dichlorobenzyl)sulfonyl)-2-(4-methoxy-3-nitrobenzylidene)-2H benzo[b][1,4]thiazin-3(4H)-one; (Z)-2-(3-amino-4-methoxybenzylidene)-6-((2,6-dichlorobenzyl)sulfonyl)-2H-benzo[b][1,4]thiazin-3(4H)-one; (Z)-6-((2,6-dichlorobenzyl)sulfonyl)-2-(4-(4-methylpiperazin-1-yl)benzylidene)-2H-benzo [b][1,4]thiazin -3(4H)-one; (Z)-6-((2,6-dichlorobenzyl)sulfonyl)-2-(4-nitrobenzylidene)-2H -benzo[b][1,4]thiazin-3(4H)-one; (Z)-2-(4-aminobenzylidene)-6-((2,6-dichlorobenzyl)sulfonyl) -2H-benzo[b][1,4]thiazin-3(4H)-one; (Z)-6-((2,6-dichlorobenzyl)sulfonyl)-2-(4-fluorobenzylidene)-2H-benzo[b][1,4]thiazin-3(4H)-one; (Z)-2-(4-chlorobenzylidene)-6-((2,6-dichlorobenzyl)sulfonyl)-2H-benzo[b][1,4]thiazin-3(4H)-one; (Z)-2-(4-bromobenzylidene)-6-((2,6-dichlorobenzyl)sulfonyl)-2H-benzo[b][1,4]thiazin-3(4H)-one; (Z)-6-((2,6-dichlorobenzyl)sulfonyl)-2-(4-methoxybenzylidene)-2H-benzo[b][1,4]thiazin-3(4H)-one; (Z)-6-((2,6-dichlorobenzyl)sulfonyl)-2-(4-methylbenzylidene)-2H-benzo[b][1,4]thiazin-3(4H)-one; (Z)-6-((2,6-dichlorobenzyl)sulfonyl)-2-(2,4,6-trimethoxybenzylidene)-2H-benzo[b][1,4]thiazin -3(4H)-one; (Z)-6-((2,6-dichlorobenzyl)sulfonyl)-2-(2,4-dichlorobenzylidene)-2H -benzo[b][1,4]thiazin-3(4H)-one; (Z)-6-((2,6-dichlorobenzyl)sulfonyl)-2-(2,4,6-trifluorobenzylidene)-2H-benzo[b][1,4]thiazin-3(4H)-one; (Z)-methyl 2-((4-((6-((2,6-dichlorobenzyl)sulfonyl)-3-oxo-3,4-dihydro-2H-benzo[b][1,4]thiazin-2-ylidene)methyl)phenyl)amino)acetate; (Z)-2-((4-((6-((2,6-dichlorobenzyl)sulfonyl)-3-oxo-3,4-dihydro-2H-benzo[b][1,4]thiazin-2-ylidene)methyl)phenyl)amino)acetic acid; (Z)-6-((2,6-dichlorobenzyl)sulfonyl)-2-(4-hydroxy-2,6-dimethoxybenzylidene)-2H-benzo[b][1,4]thiazin -3(4H)-one; (Z)-2-(4-chloro-3-nitrobenzylidene)-6-((2,6-dichlorobenzyl)sulfonyl)-2H -benzo[b][1,4]thiazin-3(4H)-one; (Z)-6-((2,6-dichlorobenzyl)sulfonyl)-2-(2,4-difluorobenzylidene)-2H-benzo[b][1,4]thiazin-3(4H)-one; (Z)-6-((2,6-dichlorobenzyl)sulfonyl) -2-(2,4,6-trifluorobenzylidene)-2H-benzo[b][1,4]thiazin-3(4H)-one; (Z)-methyl 4-((6-((2,6-dichlorobenzyl)sulfonyl)-3-oxo-3,4-dihydro-2H-benzo[b][1,4]thiazin-2-ylidene)methyl)benzoate; (Z)-methyl 4-((6-((2,6-dichlorobenzyl)sulfonyl)-3-oxo-3,4-dihydro -2H-benzo[b][1,4]thiazin-2-ylidene)methyl)-3-nitrobenzoate; (Z)-4-((6-((2,6-dichlorobenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dichlorobenzyl)sulfonyl)-2H-benzo[b][1,4]thiazin-3(4H)-one; (Z)-2-(4-(benzyloxy)-3-nitrobenzylidene)-6-((2,6-dichlorobenzyl)sulfonyl)-2H-benzo[b][1,4]thiazin-3(4H)-one; and (Z) -6-((2,6-dichlorobenzyl)sulfonyl)-2-(4-hydroxy-3-nitrobenzylidene)-2H-benzo[b][1,4]thiazin -3(4H)-one.

13. The compound according to claim 12 which is (Z)-6-((2,6-dichlorobenzyl)sulfonyl)-2-(4-hydroxy-3-nitrobenzylidene)-2H-benzo [b][1,4]thiazin-3(4H)-one, or salt thereof.

14. A compound according to claim 3, or a salt thereof, wherein at least one of $R^6$ and $R^8$ is —$NO_2$ and at least $R^7$ is other than hydrogen or halogen.

15. A compound according to claim 14, or a salt thereof, wherein said compound is selected from the group consisting of (Z)-4-((6-chloro-3-oxo-3,4-dihydro-2H -benzo[b][1,4]thiazin-2-ylidene)methyl)-2-nitrophenyl acetate; (Z)-4-((7-methoxy-3-oxo-3,4-dihydro-2H-benzo[b][1,4]thiazin-2-ylidene)methyl)-2-nitrophenyl acetate; (Z)-4-((7-bromo-3-oxo-3,4-dihydro-2H-benzo[b][1,4]thiazin-2-ylidene) methyl)-2-nitrophenyl acetate; (Z)-4-((7-methyl-3-oxo-3,4-dihydro-2H-benzo[b][1,4]thiazin-2-ylidene)methyl)-2-nitrophenyl acetate; (Z)-2-(4-acetoxy-3-nitrobenzylidene)-3-oxo-3,4-dihydro-2H-benzo[b][1,4]thiazine-7-carboxylic acid; (Z)-4-((7-fluoro-3-oxo-3,4-dihydro-2H-benzo[b][1,4]thiazin-2-ylidene)methyl)-2-nitrophenyl acetate; (Z)-4-((6-fluoro-3-oxo-3,4-dihydro-2H-benzo[b][1,4]thiazin-2-ylidene)methyl)-2-nitrophenyl acetate; (Z)-4-((4-acetyl-7-methoxy-3-oxo-3,4-dihydro-2H -benzo[b][1,4]thiazin-2-ylidene)methyl)-2-nitrophenyl acetate; (Z)-2-(4-(benzyloxy)-3-nitrobenzylidene)-7-fluoro-2H-benzo[b][1,4]thiazin-3(4H)-one; and (Z)-7-fluoro-2-(4-hydroxy -3-nitrobenzylidene)-2H-benzo[b][1,4]thiazin-3(4H)-one.

16. A compound according to claim 9, or a salt thereof, selected from the group consisting of (Z)-4-((6-((2,6-dibromobenzyl)sulfonyl)-3-oxo-3,4-dihydro-2H -benzo[b][1,4]thiazin-2-ylidene)methyl)-2-nitrophenyl acetate; (Z)-4-((6-((2,6-dibromobenzyl)sulfonyl)-3-oxo-3,4-dihydro-2H-benzo [b][1,4]thiazin-2-ylidene)methyl)phenyl acetate; (Z)-2-benzylidene-6-((2,6-dibromobenzyl)sulfonyl)-2H-benzo [b][1,4]thiazin-3(4H)-one; (Z)-6-((2,6-dibromobenzyl)sulfonyl)-2-(4-methoxy-3-nitrobenzylidene)-2H -benzo[b][1,4]thiazin-3(4H)-one; (Z)-2-(3-amino-4-methoxybenzylidene)-6-((2,6-dibromobenzyl)sulfonyl)-2H-benzo [b][1,4]thiazin-3(4H)-one; (Z)-6-((2,6-dibromobenzyl)sulfonyl)-2-(4-(4-methylpiperazin-1-yl)benzylidene)-2H-benzo [b][1,4]thiazin -3(4H)-one; (Z)-6-((2,6-dibromobenzyl)sulfonyl)-2-(4-nitrobenzylidene)-2H -benzo [b][1,4]thiazin-3(4H)-one; (Z)-2-(4-aminobenzylidene)-6-((2,6-dibromobenzyl)sulfonyl)-2H-benzo [b][1,4]thiazin-3(4H)-one; (Z)-6-((2,6-dibromobenzyl)sulfonyl)-2-(4-fluorobenzylidene)-2H-benzo [b][1,4]thiazin-3(4H)-one; (Z)-2-(4-chlorobenzylidene)-6-((2,6-dibromobenzyl)sulfonyl)-2H-benzo [b][1,4]thiazin-3(4H)-one; (Z)-2-(4-bromobenzylidene)-6-((2,6-dibromobenzyl)sulfonyl)-2H-benzo [b][1,4]thiazin-3(4H)-one; (Z)-6-((2,6-dibromobenzyl)sulfonyl)-2-(4-methoxybenzylidene)-2H-benzo [b][1,4]thiazin-3(4H)-one; (Z)-6-((2,6-dibromobenzyl)sulfonyl)-2-(4-methylbenzylidene)-2H-benzo [b][1,4]thiazin-3(4H)-one; (Z)-6-((2,6-dibromobenzyl)sulfonyl)-2-(2,4,6-trimethoxybenzylidene)-2H-benzo [b][1,4]thiazin-3(4H)-one; (Z)-6-((2,6-dibromobenzyl)sulfonyl)-2-(2,4-dibromobenzylidene)-2H -benzo [b][1,4]thiazin-3(4H)-one; (Z)-6-((2,6-dibromobenzyl)sulfonyl)-2-(2,4,6-trifluorobenzylidene)-2H-benzo[b][1,4]thiazin-3(4H)-one; (Z)-methyl 2-((4-((6-((2,6-dibromobenzyl)sulfonyl)-3-oxo-3,4-dihydro-2H-benzo [b][1,4]thiazin-2-ylidene)methyl)phenyl)amino)acetate; (Z)-2-((4-((6-((2,6-dibromobenzyl)sulfonyl)-3-oxo-3,4-dihydro-2H-benzo [b][1,4]thiazin-2-ylidene)methyl)phenyl)amino) acetic acid; (Z)-6-((2,6-dibromobenzyl)sulfonyl)-2-(4-hydroxy-2,6-dimethoxybenzylidene)-2H-benzo [b][1,4]thiazin-3(4H)-one; (Z)-2-(4-chloro-3-nitrobenzylidene)-6-((2,6-dibromobenzyl)sulfonyl)-2H -benzo [b][1,4]thiazin-3

(4H)-one; (Z)-6-((2,6-dibromobenzyl)sulfonyl)-2-(2,4-difluorobenzylidene)-2H-benzo [b][1,4]thiazin-3(4H)-one; (Z)-6-((2,6-dibromobenzyl)sulfonyl)-2-(2,4,6-trifluorobenzylidene)-2H-benzo [b][1,4]thiazin-3(4H)-one; (Z)-methyl 4-((6-((2,6-dibromobenzyl)sulfonyl)-3-oxo-3,4-dihydro-2H-benzo [b][1,4]thiazin-2-ylidene)methyl)benzoate; (Z)-methyl 4-((6-((2,6-dibromobenzyl)sulfonyl)-3-oxo-3,4-dihydro-2H-benzo[b][1,4]thiazin-2-ylidene)methyl)-3-nitrobenzoate; (Z)-4-((6-((2,6-dibromobenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dibromobenzyl)sulfonyl)-2H-benzo[b][1,4]thiazin-3(4H)-one; (Z)-2-(4-(benzyloxy)-3-nitrobenzylidene)-6-((2,6-dibromobenzyl)sulfonyl)-2H-benzo [b][1,4]thiazin-3(4H)-one; (Z)-6-((2,6-dibromobenzyl)sulfonyl)-2-(4-hydroxy-3-nitrobenzylidene)-2H-benzo [b][1,4]thiazin-3(4H)-one; (Z)-4-((6-((2,6-difluorobenzyl)sulfonyl)-3-oxo-3,4-dihydro-2H-benzo[b][1,4]thiazin-2-ylidene) methyl)-2-nitrophenyl acetate; (Z)-4-((6-((2,6-difluorobenzyl)sulfonyl)-3-oxo-3,4-dihydro-2H-benzo[b][1,4]thiazin-2-ylidene)methyl)phenyl acetate; (Z)-2-benzylidene-6-((2,6-difluorobenzyl)sulfonyl)-2H-benzo[b][1,4]thiazin-3(4H)-one; (Z)-6-((2,6-difluorobenzyl)sulfonyl)-2-(4-methoxy-3-nitrobenzylidene)-2H-benzo [b][1,4]thiazin-3(4H)-one; (Z)-2-(3-amino-4-methoxybenzylidene)-6-((2,6-difluorobenzyl)sulfonyl)-2H -benzo[b][1,4]thiazin-3(4H)-one; (Z)-6-((2,6-difluorobenzyl)sulfonyl)-2-(4-(4-methylpiperazin-1-yl)benzylidene)-2H-benzo[b][1,4]thiazin-3(4H)-one; (Z)-6-((2,6-difluorobenzyl)sulfonyl)-2-(4-nitrobenzylidene)-2H-benzo[b][1,4]thiazin-3(4H)-one; (Z)-2-(4-aminobenzylidene)-6-((2,6-difluorobenzyl)sulfonyl)-2H-benzo [b][1,4]thiazin-3(4H)-one; (Z)-6-((2,6-difluorobenzyl)sulfonyl)-2-(4-fluorobenzylidene)-2H-benzo [b][1,4]thiazin-3(4H)-one; (Z)-2-(4-chlorobenzylidene)-6-((2,6-difluorobenzyl)sulfonyl)-2H-benzo[b][1,4]thiazin-3(4H)-one; (Z)-2-(4-bromobenzylidene)-6-((2,6-difluorobenzyl)sulfonyl)-2H-benzo [b][1,4]thiazin-3(4H)-one; (Z)-6-((2,6-difluorobenzyl)sulfonyl)-2-(4-methoxybenzylidene)-2H-benzo[b][1,4]thiazin-3(4H)-one; (Z)-6-((2,6-difluorobenzyl)sulfonyl)-2-(4-methylbenzylidene)-2H-benzo [b][1,4]thiazin-3(4H)-one; (Z)-6-((2,6-difluorobenzyl)sulfonyl)-2-(2,4,6-trimethoxybenzylidene)-2H -benzo[b][1,4]thiazin-3(4H)-one; (Z)-6-((2,6-difluorobenzyl)sulfonyl)-2-(2,4-difluorobenzylidene)-2H-benzo[b][1,4]thiazin-3(4H)-one; (Z)-6-((2,6-difluorobenzyl)sulfonyl)-2-(2,4,6-trifluorobenzylidene)-2H-benzo[b][1,4]thiazin-3(4H)-one; (Z)-methyl 2-((4-((6-((2,6-difluorobenzyl)sulfonyl)-3-oxo-3,4-dihydro-2H-benzo[b][1,4]thiazin-2-ylidene)methyl)phenyl)amino)acetate; (Z)-2-((4-((6-((2,6-difluorobenzyl)sulfonyl)-3-oxo-3,4-dihydro-2H-benzo[b][1,4]thiazin-2-ylidene)methyl)phenyl)amino)acetic acid; (Z)-6-((2,6-difluorobenzyl)sulfonyl)-2-(4-hydroxy-2,6-dimethoxybenzylidene)-2H-benzo [b][1,4]thiazin-3(4H)-one; (Z)-2-(4-chloro-3-nitrobenzylidene)-6-((2,6-difluorobenzyl)sulfonyl)-2H -benzo[b][1,4]thiazin-3(4H)-one; (Z)-6-((2,6-difluorobenzyl)sulfonyl)-2-(2,4-difluorobenzylidene)-2H-benzo[b][1,4]thiazin-3(4H)-one; (Z)-6-((2,6-difluorobenzyl)sulfonyl)-2-(2,4,6-trifluorobenzylidene)-2H-benzo[b][1,4]thiazin-3 (4H)-one; (Z)-methyl 4-((6-((2,6-difluorobenzyl)sulfonyl)-3-oxo-3,4-dihydro-2H-benzo [b][1,4]thiazin-2-ylidene)methyl)benzoate; (Z)-methyl 4-((6-((2,6-difluorobenzyl)sulfonyl)-3-oxo-3,4-dihydro-2H-benzo[b][1,4]thiazin-2-ylidene)methyl)-3-nitrobenzoate; (Z)-4-((6-((2,6-difluorobenzyl)sulfonyl)-3-oxo-3,4-dihydro-2H -benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-difluorobenzyl)sulfonyl)-2H-benzo[b][1,4]thiazin-3(4H) -one; (Z)-2-(4-(benzyloxy)-3-nitrobenzylidene)-6-((2,6-difluorobenzyl)sulfonyl)-2H -benzo[b][1,4]thiazin-3(4H)-one; (Z)-6-((2,6-difluorobenzyl)sulfonyl)-2-(4-hydroxy-3-nitrobenzylidene)-2H-benzo[b][1,4]thiazin-3(4H)-one; (Z)-4-((6-((2,6-dimethylbenzyl)sulfonyl)-3-oxo-3,4-dihydro-2H-benzo[b][1,4]thiazin-2-ylidene)methyl)-2-nitrophenyl acetate; (Z)-4-((6-((2,6-dimethylbenzyl)sulfonyl)-3-oxo-3,4-dihydro-2H-benzo[b][1,4]thiazin-2-ylidene)methyl)phenyl acetate; (Z)-2-benzylidene-6-((2,6-dimethylbenzyl)sulfonyl)-2H -benzo[b][1,4]thiazin-3(4H)-one; (Z)-6-((2,6-dimethylbenzyl)sulfonyl)-2-(4-methoxy-3-nitrobenzylidene)-2H-benzo[b][1,4]thiazin-3(4H)-one; (Z)-2-(3-amino-4-methoxybenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-(4-methylpiperazin-1-yl)benzylidene)-2H-benzo[b][1,4] thiazin-3(4H)-one; (Z)-6-((2,6-dimethylbenzyl)sulfonyl)-2-(4-nitrobenzylidene)-2H -benzo[b][1,4]thiazin-3(4H)-one; (Z)-2-(4-aminobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-fluorobenzylidene)-2H-benzo[b][1,4]thiazin-3(4H)-one; (Z)-2-(4-chlorobenzylidene)-6-((2,6-dimethylbenzyl)sulfonyl)-2H-benzo[b][1,4]thiazin-3 (4H)-one; (Z)-2-(4-bromobenzylidene)-6-((2,6-dimethylbenzyl)sulfonyl)-2H-benzo[b][1,4]thiazin-3(4H)-one; (Z)-6-((2,6-dimethylbenzyl)sulfonyl)-2-(4-methoxybenzylidene)-2H-benzo[b][1,4]thiazin-3(4H)-one; (Z)-6-((2,6-dimethylbenzyl)sulfonyl)-2-(4-methylbenzylidene)-2H-benzo[b][1,4]thiazin-3(4H)-one; (Z)-6-((2,6-dimethylbenzyl)sulfonyl)-2-(2,4,6-trimethoxybenzylidene)-2H-benzo[b][1,4]thiazin-3(4H)-one; (Z)-6-((2,6-dimethylbenzyl)sulfonyl)-2-(2,4-dimethylbenzylidene)-2H -benzo[b][1,4]thiazin-3(4H)-one; (Z)-6-((2,6-dimethylbenzyl)sulfonyl)-2-(2,4,6-trifluorobenzylidene)-2H-benzo[b][1,4]thiazin-3(4H)-one; (Z)-methyl 2-((4-((6-((2,6-dimethylbenzyl)sulfonyl)-3-oxo-3,4-dihydro-2H-benzo[b][1,4]thiazin-2-ylidene)methyl)phenyl)amino)acetate; (Z)-2-((4-((6-((2,6-dimethylbenzyl)sulfonyl)-3-oxo-3,4-dihydro-2H-benzo[b][1,4]thiazin-2-ylidene)methyl)phenyl)amino)acetic acid; (Z)-6-((2,6-dimethylbenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dimethylbenzyl)sulfonyl)-2H-benzo [b][1,4]thiazin-3(4H)-one; (Z)-6-((2,6-dimethylbenzyl)sulfonyl)-2-(2,4-difluorobenzylidene)-2H-benzo[b][1,4]thiazin-3(4H)-one; (Z)-6-((2,6-dimethylbenzyl)sulfonyl)-2-(2,4,6-trifluorobenzylidene)-2H-benzo[b][1,4]thiazin-3(4H)-one; (Z)-methyl 4-((6-((2,6-dimethylbenzyl)sulfonyl)-3-oxo-3,4-dihydro-2H-benzo[b][1,4]thiazin-2-ylidene)methyl)benzoate; (Z)-methyl 4-((6-((2,6-dimethylbenzyl)sulfonyl)-3-oxo-3,4-dihydro-2H-benzo[b][1,4]thiazin-2-ylidene)methyl)-3-nitrobenzoate; (Z)-4-((6-((2,6-dimethylbenzyl)sulfonyl)-3-oxo-3,4-dihydro-2H-benzo[b][1,4]thiazin-2-ylidene) methyl)-2-nitrophenyl 4-methylbenzenesulfonate; (Z)-2-(4-(2H-tetrazol-5-yl)benzylidene)-6-((2,6-dimethylbenzyl)sulfonyl)-2H-benzo[b][1,4]thiazin-3(4H)-one; (Z)-2-(4-(benzyloxy)-3-nitrobenzylidene)-6-((2,6-dimethylbenzyl)sulfonyl)-2H-benzo[b][1,4]thiazin-3(4H)-one; and (Z)-6-((2,6-dimethylbenzyl)sulfonyl)-2-(4-hydroxy-3-nitrobenzylidene)-2H -benzo[b][1,4]thiazin-3(4H)-one; (Z)-4-((6-((2,6-dimethoxybenzyl)sulfonyl)-3-oxo-3,4-dihydro-2H-benzo[b][1,4]thiazin-2-ylidene)methyl)-2-nitrophenyl acetate; (Z)-4-((6-((2,6-dimethoxybenzyl)sulfonyl)-3-oxo-3,4-dihydro-2H-benzo[b][1,4]thiazin-2-ylidene)methyl) phenyl acetate; (Z)-2-benzylidene-6-((2,6-dimethoxybenzyl)sulfonyl)-2H-benzo[b][1,4]thiazin-3(4H) -one; (Z)-6-((2,6-dimethoxybenzyl)sulfonyl)-2-(4-methoxy-3-nitrobenzylidene)-2H -benzo[b][1,4]thiazin-3(4H)-one; (Z)-2-(3-amino-4-methoxybenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-(4-methylpiperazin-1-yl)benzylidene)-2H-benzo[b][1,4]

thiazin-3(4H)-one; (Z)-6-((2,6-dimethoxybenzyl)sulfonyl)-2-(4-nitrobenzylidene)-2H-benzo[b][1,4]thiazin-3(4H)-one; (Z)-2-(4-aminobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-fluorobenzylidene)-2H-benzo[b][1,4]thiazin-3(4H)-one; (Z)-2-(4-chlorobenzylidene)-6-((2,6-dimethoxybenzyl)sulfonyl)-2H-benzo[b][1,4]thiazin-3(4H)-one; (Z)-2-(4-bromobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(4-methoxybenzylidene)-2H-benzo[b][1,4]thiazin-3(4H)-one; (Z)-6-((2,6-dimethoxybenzyl)sulfonyl)-2-(4-methylbenzylidene)-2H-benzo[b][1,4]thiazin-3(4H)-one; (Z)-6-((2,6-dimethoxybenzyl)sulfonyl)-2-(2,4,6-trimethoxybenzylidene)-2H-benzo[b][1,4]thiazin-3(4H)-one; (Z)-6-((2,6-dimethoxybenzyl)sulfonyl)-2-(2,4-dimethoxybenzylidene)-2H-benzo[b][1,4]thiazin-3(4H)-one; (Z)-6-((2,6-dimethoxybenzyl)sulfonyl)-2-(2,4,6-trifluorobenzylidene)-2H-benzo[b][1,4]thiazin-3(4H)-one; (Z)-methyl 2-((4-((6-((2,6-dimethoxybenzyl)sulfonyl)-3-oxo-3,4-dihydro-2H-benzo[b][1,4]thiazin-2-ylidene)methyl)phenyl)amino)acetate; (Z)-2-((4-((6-((2,6-dimethoxybenzyl)sulfonyl)-3-oxo-3,4-dihydro-2H-benzo[b][1,4]thiazin-2-ylidene)methyl)phenyl)amino)acetic acid; (Z)-6-((2,6-dimethoxybenzyl)sulfonyl)-2-(4-hydroxy-2,6-dimethoxybenzylidene)-2H-benzo[b][1,4]thiazin-3(4H)-one; (Z)-2-(4-chloro-3-nitrobenzylidene)-6-((2,6-dimethoxybenzyl)sulfonyl)-2H-benzo[b][1,4]thiazin-3(4H)-one; (Z)-6-((2,6-dimethoxybenzyl)sulfonyl)-2-(2,4-difluorobenzylidene)-2H-benzo[b][1,4]thiazin-3(4H)-one; (Z)-6-((2,6-dimethoxybenzyl)sulfonyl)-2-(2,4,6-trifluorobenzylidene)-2H-benzo[b][1,4]thiazin-3(4H)-one; (Z)-methyl 4-((6-((2,6-dimethoxybenzyl)sulfonyl)-3-oxo-3,4-dihydro-2H-benzo[b][1,4]thiazin-2-ylidene)methyl)benzoate; (Z)-methyl 4-((6-((2,6-dimethoxybenzyl)sulfonyl)-3-oxo-3,4-dihydro-2H-benzo[b][1,4]thiazin-2-ylidene)methyl)-3-nitrobenzoate; (Z)-4-((6-((2,6-dimethoxybenzyl)sulfonyl)-3-oxo-3,4-dihydro-2H-benzo[b][1,4]thiazin-2-ylidene)methyl)-2-nitrophenyl 4-methylbenzenesulfonate; (Z)-2-(4-(2H-tetrazol-5-yl)benzylidene)-6-((2,6-dimethoxybenzyl)sulfonyl)-2H-benzo[b][1,4]thiazin-3(4H)-one; (Z)-2-(4-(benzyloxy)-3-nitrobenzylidene)-6-((2,6-dimethoxybenzyl)sulfonyl)-2H-benzo[b][1,4]thiazin-3(4H)-one; and (Z)-6-((2,6-dimethoxybenzyl)sulfonyl)-2-(4-hydroxy-3-nitrobenzylidene)-2H-benzo[b][1,4]thiazin-3(4H)-one.

17. A process for preparing a compound of Formula I according to claim 1, said process comprising:
condensing an aldehyde of Formula III

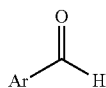

Formula III with a compound according to Formula IV:

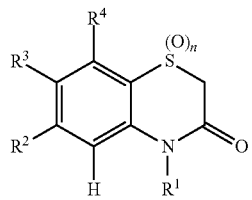

Formula IV in a reaction mixture, wherein Ar, $R^1$, $R^2$, $R^3$, $R^4$, and n, are as defined in claim 1; and isolating from the reaction mixture the compound of Formula I according to claim 1, or a salt thereof.

18. The process according to claim 17, wherein said condensation takes place in the presence of one or more of an anhydride and a base.

19. The process according to claim 18, wherein said anhydride is acetic anhydride and said base is triethylamine.

20. The process according to claim 19, wherein said reaction mixture is heated to reflux.

21. The process according to claim 17, wherein said compound according to Formula IV is prepared by:
a) functionalizing 2H-1,4-Benzothiazin-3(4H)-one with chlorosulfonic acid to give 3-oxo-3,4-dihydro-2H-benzo[b][1,4]thiazine-6-sulfonyl chloride, or a derivative thereof;
b) reacting said 3-oxo-3,4-dihydro-2H-benzo[b][1,4]thiazine-6-sulfonyl chloride with sodium sulfite to give a reactive intermediate; and
c) reacting said reactive intermediate with a compound of Formula V:

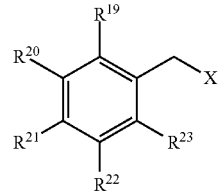

Formula V to give a compound of Formula IV, wherein $R^{19}$, $R^{20}$, $R^{21}$, $R^{22}$, and $R^{23}$ are as defined in claim 1, and X is a leaving group.

22. The process according to claim 17, wherein said compound according to Formula IV is prepared by:
a) functionalizing 2H-1,4-Benzothiazin-3(4H)-one, or a derivative thereof, with chlorosulfonic acid to give 3-oxo-3,4-dihydro-2H-benzo[b][1,4]thiazine-6-sulfonyl chloride;
b) reacting said 3-oxo-3,4-dihydro-2H-benzo[b][1,4]thiazine-6-sulfonyl chloride with Zn to form a reactive Zn complex; and
c) reacting said reactive Zn complex with a compound of Formula V:

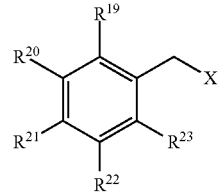

Formula V to give a compound of Formula IV, wherein $R^{19}$, $R^{20}$, $R^{21}$, $R^{22}$, and $R^{23}$ are as defined in claim 1, and X is a leaving group.

23. The process according to claim 17, wherein said compound according to Formula IV is prepared by:
a) reacting compound A:

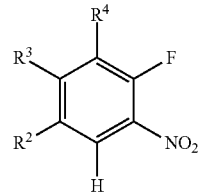

A with $HSCH_2CO_2R$, wherein R is H or $(C_1-C_6)$alkyl and $R^2$, $R^3$, and $R^4$ are as defined in claim 1, to form compound B:

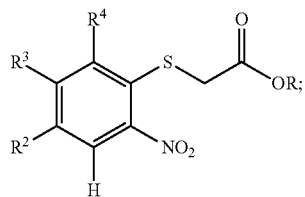

and b) reducing the nitro group of compound B to give said compound according to Formula IV.

24. The process according to claim 23, wherein reducing the nitro group of compound B comprises treating compound B with Zn and acetic acid.

25. The process according to claim 23, wherein reducing the nitro group of compound B comprises treating compound B with $Na_2S_2O_4$.

26. A pharmaceutical composition comprising a pharmaceutically acceptable carrier and a compound of Formula I, or a pharmaceutically acceptable salt thereof, according to claim 1.

27. A method of treating an individual suffering from a cellular proliferative disorder, comprising administering to the individual an effective amount of at least one compound of Formula I, or a pharmaceutically acceptable salt thereof, according to claim 1, wherein the cellular proliferative disorder is selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign pro static hyperplasia, X linked lymphocellular proliferative disorder, post transplantation lymphocellular proliferative disorder, macular degeneration, retinopathies, proliferative vitreoretinopathy, and noncancerous lymphocellular proliferative disorders.

28. A method of treating an individual suffering from a cancer, comprising administering to the individual an effective amount of at least one compound of Formula I, or a pharmaceutically acceptable salt thereof, according to claim 1, wherein the cancer is selected from the group consisting of ovarian cancer; cervical cancer; breast cancer; prostate cancer; testicular cancer, lung cancer, renal cancer; colorectal cancer; skin cancer; brain cancer; pancreatic cancer; stomach cancer; liver cancer; uterine cancer; cancer of the vulva; cancer of the vagina; cardiac cancer; lymphoma; myelodysplastic syndrome; and leukemia.

29. The method of claim 28 wherein the compound is (Z)-6-((2,6-dichlorobenzyl)sulfonyl)-2-(4-hydroxy-3-nitrobenzylidene)-2H-benzo [b][1,4]thiazin-3(4H)one, or pharmaceutically acceptable salt thereof.

30. The method according to claim 29 wherein the activity of one or more kinases selected from the group consisting of casein kinase 2, cyclin-dependent kinase 9 and PIM1 is inhibited in cancer cells of the individual.

31. A method of inducing apoptosis of cancer cells in an individual afflicted with cancer, comprising administering to the individual an effective amount of at least one compound of Formula I, or a pharmaceutically acceptable salt thereof, according to claim 1.

32. The method of claim 31 wherein the compound is (Z)-6-((2,6-dichlorobenzyl)sulfonyl)-2-(4-hydroxy-3-nitrobenzylidene)-2H-benzo [b][1,4]thiazin-3(4H)-one, or pharmaceutically acceptable salt thereof.

33. The method according to claim 32 wherein the activity of one or more kinases selected from the group consisting of casein kinase 2, cyclin-dependent kinase 9 and PIM1 is inhibited in cancer cells of the individual.

34. The method of claim 31, wherein the cancer cells are tumor cells.

35. The method according to claim 34, wherein the tumor cells are selected from the group consisting of ovarian, cervical, breast, prostate, testicular, lung, renal, colorectal, skin and brain tumor cells.

36. The method according to claim 28, wherein the leukemia is selected from the group consisting of acute myeloid leukemia, chronic myeloid leukemia, acute lymphoid leukemia, and chronic lymphoid leukemia.

* * * * *